United States Patent [19]
Landini et al.

[11] Patent Number: 6,074,817
[45] Date of Patent: *Jun. 13, 2000

[54] RECOMBINANT MONO AND POLY ANTIGENS TO DETECT CYTOMEGALOVIRUS-SPECIFIC IGM IN HUMAN SERA BY ENZYME IMMUNOASSAY

[75] Inventors: Maria P. Landini; Alessandro Ripalti, both of Bologna, Italy; Gregory T. Maine, Gurnee; Richard T. Flanders, Grayslake, both of Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/765,856

[22] PCT Filed: May 15, 1995

[86] PCT No.: PCT/IT95/00073

§ 371 Date: Dec. 27, 1996

§ 102(e) Date: Dec. 27, 1996

[87] PCT Pub. No.: WO96/01321

PCT Pub. Date: Jan. 18, 1996

[30]   Foreign Application Priority Data

Jul. 1, 1994  [IT]  Italy .................... T094A0543

[51] Int. Cl.$^7$ .......................... C12Q 1/70; G01N 33/569

[52] U.S. Cl. ......................... 435/5; 435/69.3; 435/71.2; 435/252.33; 435/254.23; 435/320.1; 436/518; 436/531; 436/534; 436/513; 436/548; 530/350

[58] Field of Search ................................ 435/5, 7.6, 7.92, 435/69.3, 71.1, 71.2, 252.33, 254.23, 320.1; 530/350; 436/518, 531, 534, 513, 548

[56]   References Cited

U.S. PATENT DOCUMENTS

| | | | |
|---|---|---|---|
| 5,124,255 | 6/1992 | Bolling et al. | 435/69.3 |
| 5,244,630 | 9/1993 | Khalil et al. | 422/52 |
| 5,268,273 | 12/1993 | Buckholz | 435/69.1 |

FOREIGN PATENT DOCUMENTS

0262531 B1  4/1988  European Pat. Off. .

OTHER PUBLICATIONS

Progress in Medical Virology, (1993), vol. 40, pp. 157–177, M. P. Landini, "New Approaches and Perspectives in Cytomegalovirus Diagnosis".

Biotechniques, vol. 8, No. 5, (1990), pp. 488–491, T. Bolling, "An *Escherichia coli* Expression Vector for High–Level Production of Heterologous Proteins in Fusion with CMP–KDO Synthetase".

Journal of Clinical Laboratory Analysis, vol. 6, pp. 216–218, (1992), T. Lazzarotto et al., "Enzyme–Linked Immunoadsorbent Assay for the Detection of Cytomegalovirus–IgM: Comparison Between Eight Commercial Kits, Immunofluorescence, and Immunoblotting".

Journal of Clinical Laboratory Analysis, vol. 3, pp. 169–173, (1989), M.C. Re et al., "IgM to Human Cytomegalovirus: Comparison of Two Enzyme Immunoassays and IgM Reactivity to Viral Polypeptides Detected by Immunoblotting".

Journal of Virology, vol. 61, No. 5, (May 1987), pp. 1358–1367, G. Jahn et al., "Map Position and Nucleotide Sequence of the Gene for the Large Structural Phosphoprotein of Human Cytomegalovirus".

Archives of Virology, (1989), vol. 108, pp. 259–270, J. Basson et al., "Pattern of Anti–Cytomegalovirus IgM Antibodies Determined by Immunoblotting".

Journal of Virological Methods, vol. 46, (1994), pp. 39–50, A. Ripalti et al., "Prokaryotic Expression of a Large Fragment of the Most Antigenic Cytomegalovirus DNA–Binding Protein (ppUL44) and its Reactivity with Human Antibodies".

Journal of Medical Virology, vol. 25, pp. 179–188, (1988), W. Van der Bij et al., "Rapid Immunodiagnosis of Active Cytomegalovirus Infection by Monoclonal Antibody Staining of Blood Leucocytes".

Journal of Clinical Microbiology, vol. 27, No. 5, (May 1989), pp. 971–976, S. Ellinger et al., "Cleavage of Procaryotically Expressed Human Immunodeficiency Virus Fusion Proteins by Factor $X_a$ and Application in Western Blot (Immunoblot) Assays".

Journal of Clinical Microbiology, vol. 27, No. 10, (Oct. 1989), pp. 2324–2327, M. P. Landini et al., "Antibody Response to Recombinant Lambda gt11 Fusion Proteins in Cytomegalovirus Infection".

(List continued on next page.)

*Primary Examiner*—Donna Wortman
*Attorney, Agent, or Firm*—David L. Weinstein

[57]   ABSTRACT

A mixture of recombinant mono- and poly-epitope proteic materials able to fully replace the viral antigens when used in an enzyme immunoassay (EIA) is disclosed; the mixture includes a poly-epitope fusion protein having a first region formed by an amino acid sequence (H10) corresponding to that of the last 233 amino acids of the COOH terminus of the viral protein p52 or to a part thereof, a second region formed by an amino acid sequence (F3) corresponding to that of the last 43 amino acids of the COOH terminus of viral protein pp150 or to a part thereof, and a third region formed by an amino acid sequence (A1C2) corresponding to that taken from aa 595 to aa 614, proceeding in direction 5'→3', of the same viral protein pp150; and, in combination, a second fusion protein including a sequence of amino acids corresponding to that taken, proceeding in direction 5'→3', from aa 297 to aa 510 of the viral major matrix protein pp65 encoded by the viral gene UL83 and a third fusion protein including a sequence of amino acids corresponding to that taken, proceeding in direction 5'→3', from aa 117 to aa 373 of the viral assembly protein pp38 encoded by the viral gene UL80a. These three fusion proteins may be used combined together for the preparation of an ELISA test kit for detection of Cytomegalovirus-specific IgM in human sera.

22 Claims, 29 Drawing Sheets

OTHER PUBLICATIONS

Journal of Clinical Microbiology, vol. 26, No. 4, (Apr. 1988), pp. 654–661, S.L. Neilsen et al., "Kinetics of Specific Immunoglobulins M, E, A, and G in Congenital Primary , and Secondary Cytomegalovirus Infection Studied by Antibody–Capture Enzyme–Linked Immunosorbent Assay".

Journal of General Virology, (1987), vol. 68, pp. 1327–1337, G. Jahn et al., "The Two major Structural Phosphoproteins (pp65 and pp150) of Human Cytomegalovirus and Their Antigenic Properties".

Journal of Clinical Microbiology, vol. 32, No. 2, (Feb. 1994), pp. 358–363, A. Ripalti et al., "Construction of Polyepitope Fusion Agents of Human Cytomegalovirus ppUL32: Reactivity with Human Antibodies".

Journal of Clinical Microbiology, vol. 32, No. 4, (Apr. 1994), pp. 981–986, R. Vornhagen et al., "Early Serodiagnosis of Acute Human Cytomegalovirus Infection by Enzyme–Linked Immunosorbent Assay Using Recombinant Antigens".

Journal of Clinical Microbiology, vol. 19, No. 6, (Jun. 1984), pp. 917–919, C. A. Gleaves et al., "Rapid Detection of Cytomegalovirus in MRC–5 Cells Inoculated with Urine Specimens by Using Low–Speed Centrifugation and Monoclonal Antibody to an Early Antigen".

Archives of Virology, (1994), vol. 135, pp. 13–28, T. Lazzarotto et al., "Human Cytomegalovirus Replication Correlates with Differentiation in a Hematopoietic Progenitor Cell Line and Can Be Modulated by HIV–1".

Journal of Clinical Microbiology, vol. 29, No. 9, (Sep. 1991), pp. 1868–1872, M. P. Landini et al., "Human Cytomegalovirus Structural Proteins: Immune Reaction Against pp150 Synthetic Peptides".

Journal of Clinical Microbiology, vol. 30, No. 1, (Jan. 1992), pp. 201–206, B. Plachter et al., "Detection of Cytomegalovirus Antibodies by an Enzyme–Linked Immunosorbent Assay Using Recombinant Polypeptides of the Large Phosphorylated Tegument Protein pp150".

Journal of Clinical Microbiology, vol. 31, No. 3, (Mar. 1993), pp. 629–635, J. M. Robinson et al., "Analysis of the Humoral Response to the Flagellin Protein of *Borrelia burgdorferi:* Cloning of Regions Capable of Differentiating Lyme Disease from Syphilis".

Journal of General Virology, (1991), vol. 72 , pp. 1409–1413, J. Novak et al., "Mapping of Serologically Relevant Regions of Human Cytomegalovirus Phosphoprotein pp150 Using Synthetic Peptides".

Journal of General Virology, (1988), vol. 69, pp. 1195–1204, B.–C. Scholl et al., "Prokaryotic Expression of Immunogenic Polypeptides of the Large Phosphoprotein (pp150) of Human Cytomegalovirus".

Journal of General Virology, (1989), vol. 70, pp. 1247–1251, A. Ripalti et al., "Identification and Preliminary Use of Recombinant Lambda gt11 Fusion Proteins in Human Cytomegalovirus Diagnosis".

Journal of Biological Chemistry, vol. 261, No. 34 (1986), pp. 15831–15836, R. C. Goldman et al., "Primary Structure of CTP:CMP–3–Deoxy–D–manno–Octulosonate Cytidylyltransferase (CMP–KDO Synthetase) from *Escherichia coli*".

Gene, vol. 68 (1988), pp. 101–107, W. Mandecki et al., "Fok I Method of Gene Synthesis".

Journal of Clinical Microbiology, vol. 28, No. 6 (Jun. 1990), pp. 1375–1379, M. P. Landini et al., "Large–Scale Screening of Human Sera with Cytomegalovirus Recombinant Antigens".

The Journal of Infectious Diseases, vol. 157, No. 2 (Feb. 1988), pp. 319–325, D. Gold et al., "Immunoblot Analysis of the Humoral Immune Response in Primary Cytomegalovirus Infection".

The Journal of Infectious Diseases, vol. 160, No. 1 (Jul. 1989), pp. 159–160, M. G. Revello et al., Correlation Between Immunofluorescent Detection of Human Cytomegalovirus Immediate Early Antigens in Polymorphonuclear Leukocytes and Viremia.

Journal of Medical Virology, vol. 17 , pp. 303–311, (1985), M.P. Landini et al., "Human Immune Response to Cytomegalovirus Structural Peptides Studied by Immunoblotting".

Journal of Virology, vol. 68, No. 3 (Mar. 1994), pp. 1886–1902, S. Karlin et al., "Molecular Evolution of Herpesviruses: Genomic and Protein Sequence Comparisons".

Clinical Microbiology Reviews, vol. 5, No. 2 (Apr. 1992), pp. 204–210, W. L. Drew, "Nonpulmonary Manifestations of Cytomegalovirus Infection in Immunocompromised Patients".

Proc. Natl. Acad. Sci. USA, vol. 83, pp. 72–76, (Jan. 1986), R. A. Colbert et al., "Glucocorticoid–mediated Induction of Glucocortin: A Rapid Primary Response Common to Major Target Tissues".

TABLE 1

Comparison between IgG detection by ELISA with whole CMV or by recombinant ELISA with individual fusion proteins

| ELISA (IgG) with whole CMV | | ELISA (IgG) with the following fusion proteins: | | | | | | | | | |
|---|---|---|---|---|---|---|---|---|---|---|---|
| | | F3 | | A1C2 | | A1C2/F3 | | H10 | | A1C2/F3/H10 | |
| N | Mean Titre (Range) | N. Positives | Mean Titre (Range) | N. Positives | Mean Titre (Range) | N. Positives | Mean Titre (Range) | N. Positives | Mean Titre (Range) | N. Positives | Mean Titre (Range) |
| 28 | 291 (242-330) | 19 | 75 (17-180) | 10 | 41 (17-43) | 20 | 172 (40-490) | 19 | 214 (168-501) | 27 | 176 (140-641) |
| 40 | 576 (434-705) | 40 | 434 (53-2079) | 22 | 110 (12-440) | 40 | 825 (230-2209) | 39 | 611 (206-1038) | 40 | 880 (120-2160) |
| 40 | 1161 (690-2138) | 38 | 796 (50-2461) | 22 | 114 (25-275) | 38 | 805 (50-2351) | 40 | 758 (300-2120) | 40 | 940 (120-2405) |
| 108 TOTAL | | 98 (90.7%) | — | 54 (50%) | — | 97 (89.8%) | — | 98 (90.7%) | — | 107 (99.1%) | — |
| 14 | 0.18 (0.2-5) | 0 | — | 0 | — | 0 | — | 0 | — | 0 | — |

Fig. 6

TABLE 2

Comparison between IgM detection by ELISA with whole CMV or by recombinant ELISA with individual fusion proteins

| ELISA (IgM) with whole CMV | | | ELISA (IgM) with the following fusion proteins: | | | | | | | | | | |
|---|---|---|---|---|---|---|---|---|---|---|---|---|---|
| | | | F3 | | A1C2 | | A1C2/F3 | | H10 | | A1C2/F3/H10 | | |
| N. | Mean Titre (Range) | | N. Positives | Mean Titre (Range) | N. Positives | Mean Titre (Range) | N. Positives | Mean Titre (Range) | N. Positives | Mean Titre (Range) | N. Positives | Mean Titre (Range) | |
| 20 | 294 (242-389) | | 10 | 521 (232-1171) | 10 | 317 (85-612) | 14 | 797 (210-1417) | 19 | 578 (432-724) | 20 | 517 (386-815) | |
| 24 | 516 (210-2297) | | 18 | 1090 (210-2297) | 16 | 467 (143-1141) | 22 | 1278 (370-2561) | 23 | 887 (209-2270) | 24 | 767 (298-1973) | |
| 20 | 1341 (881-2000) | | 16 | 1163 (451-2339) | 14 | 1021 (202-2260) | 16 | 1707 (521-2249) | 20 | 1065 (579-2471) | 20 | 1121 (421-2243) | |
| 64 | TOTAL positives | | 44 (68,75%) | — | 40 (62,5%) | — | 52 (81,25%) | — | 62 (96,87%) | — | 64 (100%) | — | |
| 5 | 27 (1-56) | | 0 | — | 0 | — | 0 | — | 0 | — | 0 | — | |

Fig. 7 pMB34

SacI Sense Primer n. 1783
PstI Antisense Primer n. 3144
ppUL32 (pp150)
PCR Amplification
SacI/PstI Digestion Gel Purify
204 bp Fragment SacI-A1C2F3-PstI pROSH10

SacI Sense Primer n. 604
BamHI Antisense Primer n. 1299
ppUL44 (pp52)
PCR Amplification
SacI/BamHI Digestion
Gel Purify
696 bp Fragment PstI Sense Primer n. 604
BamHI Antisense Primer n. 1299
ppUL44 (pp52)
PCR Amplification
PstI/BamHI Digestion
Gel Purify
696 bp Fragment SacI-H10-BamHI PstI-H10-BamHI

Fig. 13A

HCMV cDNA

↓ Sense Primer n. 807
Antisense Primer n. 1572
ppUL83 (pp65)
Outer-Nest PCR Amplification Outer-Nest PCR Reaction ↓ SacI Sense Primer n. 889
BamHI Antisense Primer n. 1530
ppUL83 (pp65)
Inner-Nest PCR Amplification
SacI/BamHI Digestion
Gel Purify 642 bp Fragment SacI-pp65(297-510aa)-BamHI pMB38

↓ SacI Sense Primer n. 349
BamHI Antisense Primer n. 1119
ppUL80a (pp38)
PCR Amplification
SacI/BamHI Digestion
Gel Purify 771 bp Fragment SacI-pp38(117-373aa)-BamHI

Fig. 13B

```
         SalI
     MluI    MluI
      ▼   ▼   ▼
CCCGCGCTACGCGTCGACGCGTCTGCCC
ProAlaArgTyrAlaSerThrArgLeuPro
```

Fig. 14B

```
5' CGCGAGCT 3'
3'     TCGAGCGC 5'
```

Fig. 14C

```
CCCGCGCGCTACGCGACGTCGCGTCTGCCC
ProAlaArgTyrAlaThrSerArgLeuPro
```

Fig. 14D pCMV-4

StuI Sense Primer n. 1783
ppUL32 (pp150)
MluI Antisense Primer n. 1299
ppUL44 (pp52)
PCR Amplification
StuI/MluI Digestion
Gel Purify
906 bp Fragment StuII-A1C2F3-H10-MluI pCMV-9

StuI Sense Primer n. 889
MluI Antisense Primer n. 1530
ppUL83 (pp65)
PCR Amplification
StuI/MluI Digestion
Gel Purify
642 bp Fragment StuI-pp65(297-510aa)-MluI pCMV-26

StuI Sense Primer n. 349
MluI Antisense Primer n. 1119
ppUL80a (pp38)
PCR Amplification
StuI/MluI Digestion
Gel Purify
771 bp Fragment StuI-pp38(117-373aa)-MluI

Fig. 16A

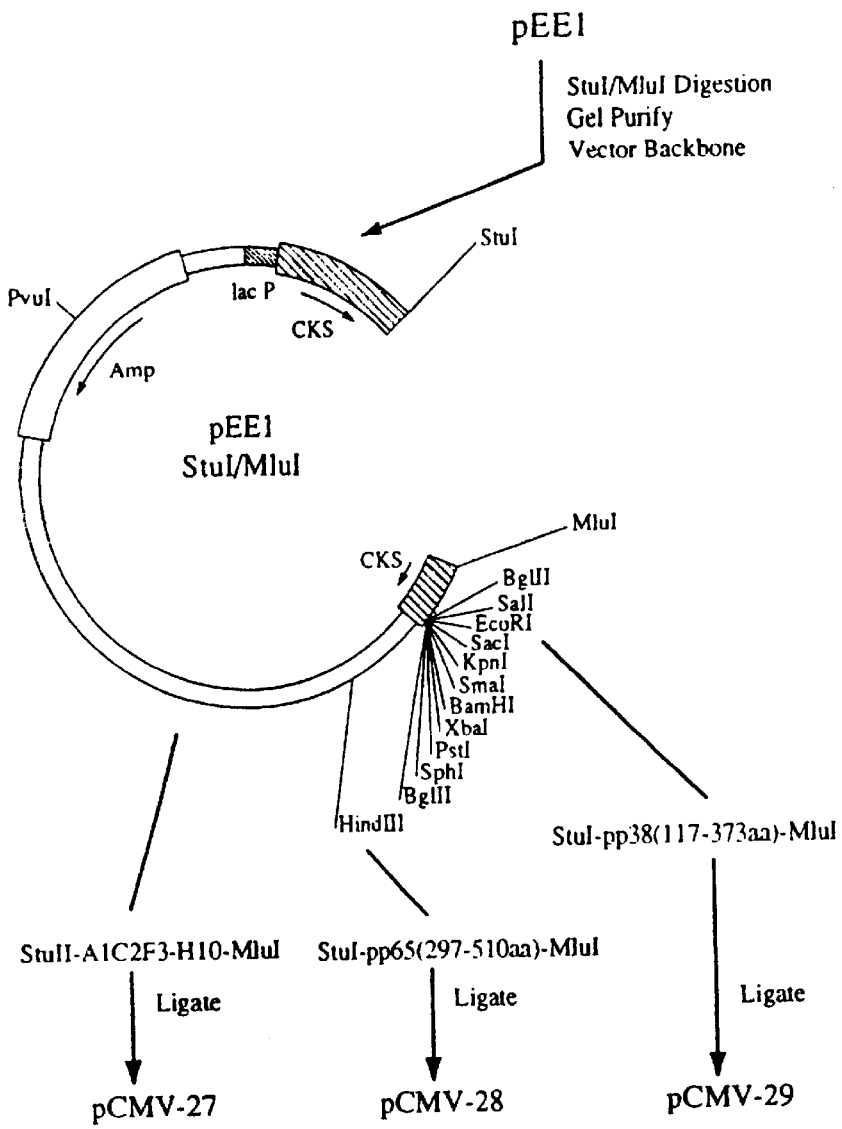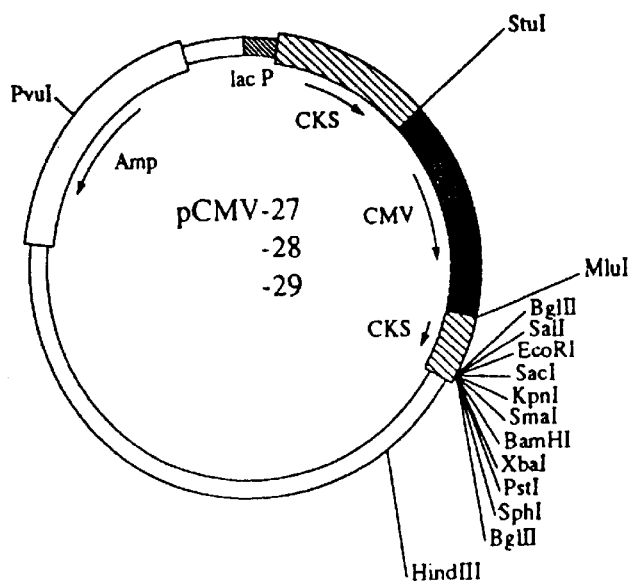
Fig. 16B

TABLE 3

| Viral Protein | Approx. MW x10³ kD | Fusion Protein | | Protein Data | | Assay Cut-off | |
|---|---|---|---|---|---|---|---|
| | | automated test | manual test | Nucleotides | Amino Acids | Manual test OD x 10³ | Autom. test |
| ppUL32+ppUL44 | 58 | | rpCMV-4 | 1783-1842+3016-3144(ppUL32) + 604-1299(ppUL44) | 595-616 + 1006-1048(ppUL32) + 202-434(ppUL44) | | |
| ppUL80a | 54 | | rpCMV-26 | 349-1119 | 117-373 | 180 | |
| ppUL32 | 36 | | rpCMV-1A | 1783-1842+3016-3144 | 595-614 + 1006-1048 | 180 | |
| ppUL44 | 51 | | rpCMV-3B | 604-1299 | 202-434 | 130 | |
| ppUL83 | 51 | | rpCMV-9 | 889-1530 | 297-510 | 170 | |
| ppUL32+ppUL44 | 60 | rpCMV-27 | | 1783-1842+3016-3144(ppUL32) + 604-1299(ppUL44) | 595-616 + 1006-1048(ppUL32) + 202-434(ppUL44) | 110 | 0.6 |
| ppUL83 | 53 | rpCMV-28 | | 889-1530 | 297-510 | | 0.6 |
| ppUL80a | 55 | rpCMV-29 | | 349-1119 | 117-373 | | 0.6 |

Fig. 18

Table 4: Automated HCMV IgM immunoassay results obtained by testing 7 HCMV IgM-negative sera using microparticles coated separately and then run sequentially and in combination

| Sample | Sample Index Value with Coated Microparticles | | | | Sample Result (Pos or Neg) | |
|---|---|---|---|---|---|---|
| | 27 | 28 | 29 | 27+28+29 | Sequential | Combination |
| BT10578 | 0.076 | 0.071 | 0.106 | 0.075 | Neg | Neg |
| BS18323 | 0.099 | 0.044 | 0.090 | 0.104 | Neg | Neg |
| BT12170 | 0.202 | 0.070 | 0.140 | 0.167 | Neg | Neg |
| BT12155 | 0.044 | 0.059 | 0.123 | 0.065 | Neg | Neg |
| BT12173 | 0.204 | 0.111 | 0.316 | 0.255 | Neg | Neg |
| BT12162 | 0.436 | 0.251 | 0.200 | 0.476 | Neg | Neg |
| BT12267 | 0.198 | 0.141 | 0.496 | 0.296 | Neg | Neg |

Fig. 19

Table 5: Automated HCMV IgM immunoassay results obtained by testing 11 HCMV IgM-positive sera using microparticles coated separately and then run sequentially and in combination

| Sample | Viral WB | Sample Index Value with Coated Microparticles | | | | Sample Result (Pos or Neg) | |
|---|---|---|---|---|---|---|---|
| | | 27 | 28 | 29 | 27+28+29 | Sequential | Combination |
| 495 | 150,65,55,38 | 3.860 | 0.894 | 4.049 | 4.550 | Pos | Pos |
| 530 | 150,65,55,38 | 1.437 | 1.416 | 2.395 | 1.647 | Pos | Pos |
| 705 | 150,65,55,38 | 1.752 | 0.120 | 0.560 | 2.091 | Pos | Pos |
| 525 | 150 | 0.784 | 0.214 | 0.438 | 0.833 | Pos | Pos |
| 587 | 150,38 | 0.824 | 1.144 | 4.780 | 2.011 | Pos | Pos |
| 316 | 150,38 | 0.629 | 0.047 | 0.724 | 0.653 | Pos | Pos |
| 498 | 150,38 | 0.616 | 0.084 | 1.502 | 0.787 | Pos | Pos |
| 317 | 150,65 | 0.036 | 1.041 | 0.109 | 0.973 | Pos | Pos |
| 472 | 150,65 | 0.960 | 1.988 | 0.572 | 0.632 | Pos | Pos |
| 457 | 150,65 | 2.768 | 0.744 | 0.717 | 3.127 | Pos | Pos |
| 301 | 150,65 | 2.888 | 0.157 | 0.658 | 2.214 | Pos | Pos |

Fig. 20

Table 6: Recombinant EIA results obtained by testing 150 IgM-positive sera

| N. of sera | HCMV serology* | | N. of sera positive for: | | | | | |
|---|---|---|---|---|---|---|---|---|
| | IgG | IgM | 1A | 3B | 4 | 9 | 26 | 4+9+26 | all fusion proteins |
| 50 | + | high | 42 | 49 | 49 | 44 | 39 | 50 | 50 |
| 50 | + | medium | 31 | 47 | 44 | 42 | 37 | 50 | 50 |
| 50 | + | low | 29 | 40 | 42 | 31 | 32 | 47 | 48 |
| tot. 150 | | | 102 | 136 | 135 | 117 | 108 | 147 (98%) | 148 (98.7%) |

* Sera were divided in three groups on the basis of EIA-IgM values. All the sera were IgM-confirmed by Western blotting. They were all IgG positive as shown by EIA.

Fig. 21

Table 7: Comparison between conventional and recombinant EIA in pregnant women. Determination of IgM titres to individual fusion proteins

| Groups of subjects | N. | N. of positive samples detected by | | | | | | | IgM titres (OD×10³) detected by | | | |
|---|---|---|---|---|---|---|---|---|---|---|---|---|
| | | Rec- EIA with fusion proteins: | | | | | | Conv-EIA | Rec-EIA with fusion proteins: | | | |
| | | 1A | 3B | 4 | 9 | 26 | 4+9+26 | all | | 3B | 4 | 9 | 26 |
| HCMV-infected pregnant women who did not transmit the infection* | 25 | 1 | 15 | 19 | 9 | 10 | 20 | 20 | 12 | 461 (+/-211) | 838 (+/-324) p=0.012 | 164 (+/-59) | 487 (+/-220) p=0.023 |
| HCMV-infected pregnant women who transmitted the infection* | 8 | 1 | 6 | 8 | 3 | 6 | 8 | 8 | 6 | 724 (+/-344) | 1450 (+/-379) | 191 (+/-52) | 1064 (+/-490) |
| HCMV-uninfected pregnant women* | 18 | 0 | 0 | 0 | 0 | 0 | 0 | 0 | 0 | nd | nd | nd | nd |

\* Samples were obtained at 22-24 weeks of gestation

Fig. 22

Table 8: Comparison between conventional and recombinant EIA in newborns

| Groups of subjects | N. | N. of positive samples detected by | | | | | | | |
|---|---|---|---|---|---|---|---|---|---|
| | | Rec - EIA with fusion proteins: | | | | | | | Conventional EIA |
| | | 1A | 3B | 4 | 9 | 26 | 4+9+26 | all | |
| Congenitally infected newborns* | 6 | 0 | 1 | 1 | 2 | 2 | 2 | 2 | 0 |
| Newborn excreting HCMV during the first year of life** | 19 | 0 | 4 | 7 | 1 | 7 | 10 | 10 | 2 |
| HCMV uninfected newborns** | 10 | 0 | 0 | 0 | 0 | 0 | 0 | 0 | 0 |

\* Sera were obtained 1-7 days after birth
\*\* Sera were obtained between 1 and 12 months after birth.

Fig. 23

Table 9: Cumulative IgM reactions to the five fusion proteins obtained in 253 IgM-positive sera from different groups of subjects

| Recombinant proteins | Number of IgM+sera (n 148) | positive samples among: | | | | Infected transplant recipients (n65) GROUPS § | | | | | | Tot n. (%) |
|---|---|---|---|---|---|---|---|---|---|---|---|---|
| | | Infected pregnant women* (n20) | Infected pregnant women** (n8) | Infected newborns° (n2) | Infected newborns°° (n10) | I | II | III | IV | V | VI | |
| | | | | | | 2 | 15 | 17 | 11 | 15 | 5 | |
| 1A | 102 | 1 | 1 | 0 | 0 | 1 | 5 | 7 | 4 | 7 | 0 | 128 (50.6) |
| 3B | 136 | 15 | 6 | 1 | 4 | 1 | 7 | 13 | 9 | 10 | 2 | 204 (80.6) |
| 4 | 135 | 19 | 8 | 1 | 7 | 1 | 12 | 17 | 11 | 14 | 3 | 228 (90.1) |
| 9 | 117 | 9 | 3 | 0 | 1 | 2 | 8 | 7 | 8 | 7 | 2 | 164 (64.8) |
| 26 | 108 | 10 | 6 | 2 | 7 | 1 | 11 | 15 | 6 | 10 | 3 | 179 (70.7) |
| 4+9 | 144 | 20 | 8 | 1 | 7 | 2 | 14 | 17 | 11 | 14 | 3 | 241 (95.2) |
| 4+9+26 | 142 | 19 | 8 | 2 | 10 | 1 | 13 | 17 | 11 | 15 | 5 | 243 (96.0) |
| 4+9+26 | 147 | 20 | 8 | 2 | 10 | 2 | 15 | 17 | 11 | 15 | 5 | 252 (99.6) |

\* HCMV infected pregnant women who did not transmit the infection
\*\* HCMV-infected pregnant women who transmitted the infection
§ Groups are referred to Table 5
° Sera were obtained during the first week of life
°° Sera were obtained from 1 to 12 months after birth

Fig. 24

Table 10: Comparison between conventional and recombinant EIA (fusion protein 4, 9 and 26) and Western blotting in 200 sera randomly selected from renal transplant recipients and pregnant women.

| | | Recombinant EIA | | Western Blotting | |
|---|---|---|---|---|---|
| | | positive | negative | positive | negative |
| Conventional EIA | positive | 86 | 2 | 86 | 2 |
| | negative | 50 | 62 | 51 | 61 |
| | totals | 136 | 64 | 137 | 63 |

Conventional EIA positive: 88
Conventional EIA negative: 112
totals: 200

Fig. 25

SEQUENCE LISTING

```
(1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 908 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..900
```

(xi) SEQUENCE DESCRIPTION: SEQ ID NO:1:

```
GAA TTC ACA GCC AAT AAC CGC GTC AGT TTC CAC GGC GTA AAA AAC ATG      48
Glu Phe Thr Ala Asn Asn Arg Val Ser Phe His Gly Val Lys Asn Met
1               5                   10                  15

CGT ATC AAC GTG CAG CTG AAG AAC TTC TAC CAG ACG CTG CTC AAT TGC      96
Arg Ile Asn Val Gln Leu Lys Asn Phe Tyr Gln Thr Leu Leu Asn Cys
                20                  25                  30

GCC GTC ACC AAA CTA CCG TGC ACG CTG CGT ATA GTT ACG GAG CAC GAC     144
Ala Val Thr Lys Leu Pro Cys Thr Leu Arg Ile Val Thr Glu His Asp
            35                  40                  45

ACG CTG TTG TAC GTG GCC AGC CGC AAC GGT CTG TTC GCC GTG GAG AAC     192
Thr Leu Leu Tyr Val Ala Ser Arg Asn Gly Leu Phe Ala Val Glu Asn
        50                  55                  60

TTT CTC ACC GAG GAA CCT TTC CAG CGT GGC GAT CCC TTC GAC AAA AAT     240
Phe Leu Thr Glu Glu Pro Phe Gln Arg Gly Asp Pro Phe Asp Lys Asn
65                  70                  75                  80

TAC GTC GGG AAC AGC GGC AAG TCG CGT GGC GGC GGC GGT GGT GGC GGC     288
Tyr Val Gly Asn Ser Gly Lys Ser Arg Gly Gly Gly Gly Gly Gly Gly
                85                  90                  95

AGC CTC TCT TCG CTG GCC AAT GCC GGC GGT CTG CAC GAC GAC GGC CCG     336
Ser Leu Ser Ser Leu Ala Asn Ala Gly Gly Leu His Asp Asp Gly Pro
                100                 105                 110

GGT CTG GAT AAC GAT CTC ATG AAC GAG CCC ATG GGT CTC GGC GGT CTG     384
Gly Leu Asp Asn Asp Leu Met Asn Glu Pro Met Gly Leu Gly Gly Leu
            115                 120                 125

GGA GGA GGT GGC GGC GGT GGC GGC AAG AAG CAC GAC CGC GGT GGC GGC     432
Gly Gly Gly Gly Gly Gly Gly Gly Lys Lys His Asp Arg Gly Gly Gly
        130                 135                 140

GGT GGT TCC GGT ACG CGG AAA ATG AGC AGC GGT GGC GGC GGC GGT GAT     480
Gly Gly Ser Gly Thr Arg Lys Met Ser Ser Gly Gly Gly Gly Gly Asp
145                 150                 155                 160

CAC GAT CAC GGT CTT TCC TCC AAG GAA AAA TAC GAG CAG CAC AAG ATC     528
His Asp His Gly Leu Ser Ser Lys Glu Lys Tyr Glu Gln His Lys Ile
                165                 170                 175

ACC AGT TAC CTG ACG TCC AAA GGT GGA TCG GGC GGC GGC GGA GGA GGA     576
Thr Ser Tyr Leu Thr Ser Lys Gly Gly Ser Gly Gly Gly Gly Gly Gly
                180                 185                 190

GGA GGC GGC GGT TTG GAT CGC AAC TCC GGC AAT TAC TTC AAC GAC GCG     624
Gly Gly Gly Gly Leu Asp Arg Asn Ser Gly Asn Tyr Phe Asn Asp Ala
            195                 200                 205

AAA GAG GAG AGC GAC AGC GAG GAT TCT GTA ACG TTC GAG TTC GTC CCT     672
Lys Glu Glu Ser Asp Ser Glu Asp Ser Val Thr Phe Glu Phe Val Pro
210                 215                 220

AAC ACC AAG AAG CAA AAG TGC GGC ACG CCG ACG CCT GTC AAT CCT TCC     720
Asn Thr Lys Lys Gln Lys Cys Gly Thr Pro Thr Pro Val Asn Pro Ser
225                 230                 235                 240

ACG GCC CCC GCT CCG GCC CCG ACA CCT ACC TTC GCG AAG CTT CAG GAA     768
Thr Ala Pro Ala Pro Ala Pro Thr Pro Thr Phe Ala Lys Leu Gln Glu
                245                 250                 255

TTC GGA TCG TCG CCC CAG AAG AGC GGT ACG GGG CCG CAA CCG GGT TCT     816
Phe Gly Ser Ser Pro Gln Lys Ser Gly Thr Gly Pro Gln Pro Gly Ser
                260                 265                 270

GCC GGC ATG GGG GGC GCC AAA ACG CCG TCG GAC GCC GTG CAG AAC ATC     864
Ala Gly Met Gly Gly Ala Lys Thr Pro Ser Asp Ala Val Gln Asn Ile
            275                 280                 285

CTC CAA AAG ATC GAG AAG ATT AAG AAC ACG GAG GAA TAGAATTC            908
Leu Gln Lys Ile Glu Lys Ile Lys Asn Thr Glu Glu
        290                 295                 300
```

(2) INFORMATION FOR SEQ ID NO:2:

(i) SEQUENCE CHARACTERISTICS:
        (A) LENGTH: 300 amino acids
        (B) TYPE: amino acid
        (D) TOPOLOGY: linear (ii) MOLECULE TYPE: Protein (xi) SEQUENCE DESCRIPTION: SEQ ID NO:2:

```
Glu Phe Thr Ala Asn Asn Arg Val Ser Phe His Gly Val Lys Asn Met
1               5                   10                  15

Arg Ile Asn Val Gln Leu Lys Asn Phe Tyr Gln Thr Leu Leu Asn Cys
            20                  25                  30

Ala Val Thr Lys Leu Pro Cys Thr Leu Arg Ile Val Thr Glu His Asp
        35                  40                  45

Thr Leu Leu Tyr Val Ala Ser Arg Asn Gly Leu Phe Ala Val Glu Asn
    50                  55                  60

Phe Leu Thr Glu Glu Pro Phe Gln Arg Gly Asp Pro Phe Asp Lys Asn
65                  70                  75                  80

Tyr Val Gly Asn Ser Gly Lys Ser Arg Gly Gly Gly Gly Gly Gly Gly
                85                  90                  95

Ser Leu Ser Ser Leu Ala Asn Ala Gly Gly Leu His Asp Asp Gly Pro
                100                 105                 110

Gly Leu Asp Asn Asp Leu Met Asn Glu Pro Met Gly Leu Gly Gly Leu
            115                 120                 125

Gly Gly Gly Gly Gly Gly Gly Lys Lys His Asp Arg Gly Gly Gly
        130                 135                 140

Gly Gly Ser Gly Thr Arg Lys Met Ser Ser Gly Gly Gly Gly Gly Asp
145                 150                 155                 160

His Asp His Gly Leu Ser Ser Lys Glu Lys Tyr Glu Gln His Lys Ile
                165                 170                 175

Thr Ser Tyr Leu Thr Ser Lys Gly Gly Ser Gly Gly Gly Gly Gly Gly
                180                 185                 190

Gly Gly Gly Gly Leu Asp Arg Asn Ser Gly Asn Tyr Phe Asn Asp Ala
            195                 200                 205

Lys Glu Glu Ser Asp Ser Glu Asp Ser Val Thr Phe Glu Phe Val Pro
210                 215                 220

Asn Thr Lys Lys Gln Lys Cys Gly Thr Pro Thr Pro Val Asn Pro Ser
225                 230                 235                 240

Thr Ala Pro Ala Pro Ala Pro Thr Pro Thr Phe Ala Lys Leu Gln Glu
            245                 250                 255

Phe Gly Ser Ser Pro Gln Lys Ser Gly Thr Gly Pro Gln Pro Gly Ser
                260                 265                 270

Ala Gly Met Gly Gly Ala Lys Thr Pro Ser Asp Ala Val Gln Asn Ile
            275                 280                 285

Leu Gln Lys Ile Glu Lys Ile Lys Asn Thr Glu Glu
    290                 295                 300
```

(2) INFORMATION FOR SEQ ID NO:3:

(i) SEQUENCE CHARACTERISTICS:
        (A) LENGTH: 906 base pairs
        (B) TYPE: nucleic acid
        (C) STRANDEDNESS: double
        (D) TOPOLOGY: linear (ii) MOLECULE TYPE: DNA (genomic)

```
    (iii) HYPOTHETICAL: NO (iv) ANTI-SENSE: NO (v) FRAGMENT TYPE: internal (vi) ORIGINAL SOURCE:
         (A) ORGANISM: Human Cytomegalovirus (HCMV)

(vii) IMMEDIATE SOURCE:
         (B) CLONE: pCMV-27

(ix) FEATURE:
         (A) NAME/KEY: CDS
         (B) LOCATION:1..906
         (D) OTHER INFORMATION:/function= "HCMV antigen"
             /product= "fusion protein a1c2f3h10"

(xi) SEQUENCE DESCRIPTION: SEQ ID NO:3:

ACG CCG ACG CCT GTC AAT CCT TCC ACG GCC CCC GCT CCG GCC CCG ACA        48
Thr Pro Thr Pro Val Asn Pro Ser Thr Ala Pro Ala Pro Ala Pro Thr
1               5                   10                  15

CCT ACC TTC GCG AAG CTT CAG GAA TTC GGA TCG TCG CCC CAG AAG AGC        96
Pro Thr Phe Ala Lys Leu Gln Glu Phe Gly Ser Ser Pro Gln Lys Ser
                20                  25                  30

GGT ACG GGG CCG CAA CCG GGT TCT GCC GGC ATG GGG GGC GCC AAA ACG       144
Gly Thr Gly Pro Gln Pro Gly Ser Ala Gly Met Gly Gly Ala Lys Thr
            35                  40                  45

CCG TCG GAC GCC GTG CAG AAC ATC CTC CAA AAG ATC GAG AAG ATT AAG       192
Pro Ser Asp Ala Val Gln Asn Ile Leu Gln Lys Ile Glu Lys Ile Lys
        50                  55                  60

AAC ACG GAG GAA CTT CAG GAA TTC ACA GCC AAT AAC CGC GTC AGT TTC       240
Asn Thr Glu Glu Leu Gln Glu Phe Thr Ala Asn Asn Arg Val Ser Phe
65                  70                  75                  80

CAC GGC GTA AAA AAC ATG CGT ATC AAC GTG CAG CTG AAG AAC TTC TAC       288
His Gly Val Lys Asn Met Arg Ile Asn Val Gln Leu Lys Asn Phe Tyr
                85                  90                  95

CAG ACG CTG CTC AAT TGC GCC GTC ACC AAA CTA CCG TGC ACG CTG CGT       336
Gln Thr Leu Leu Asn Cys Ala Val Thr Lys Leu Pro Cys Thr Leu Arg
            100                 105                 110

ATA GTT ACG GAG CAC GAC ACG CTG TTG TAC GTG GCC AGC CGC AAC GGT       384
Ile Val Thr Glu His Asp Thr Leu Leu Tyr Val Ala Ser Arg Asn Gly
        115                 120                 125

CTG TTC GCC GTG GAG AAC TTT CTC ACC GAG GAA CCT TTC CAG CGT GGC       432
Leu Phe Ala Val Glu Asn Phe Leu Thr Glu Glu Pro Phe Gln Arg Gly
130                 135                 140

GAT CCC TTC GAC AAA AAT TAC GTC GGG AAC AGC GGC AAG TCG CGT GGC       480
Asp Pro Phe Asp Lys Asn Tyr Val Gly Asn Ser Gly Lys Ser Arg Gly
145                 150                 155                 160

GGC GGT GGT GGC GGC AGC CTC TCT TCG CTG GCC AAT GCC GGC GGT           528
Gly Gly Gly Gly Gly Gly Ser Leu Ser Ser Leu Ala Asn Ala Gly Gly
                165                 170                 175

CTG CAC GAC GAC GGC CCG GGT CTG GAT AAC GAT CTC ATG AAC GAG CCC       576
Leu His Asp Asp Gly Pro Gly Leu Asp Asn Asp Leu Met Asn Glu Pro
            180                 185                 190

ATG GGT CTC GGC GGT CTG GGA GGA GGT GGC GGC GGT GGC GGC AAG AAG       624
Met Gly Leu Gly Gly Leu Gly Gly Gly Gly Gly Gly Gly Gly Lys Lys
        195                 200                 205

CAC GAC CGC GGT GGC GGC GGT GGT TCC GGT ACG CGG AAA ATG AGC AGC       672
His Asp Arg Gly Gly Gly Gly Ser Gly Thr Arg Lys Met Ser Ser
210                 215                 220

GGT GGC GGC GGC GGT GAT CAC GAT CAC GGT CTT TCC TCC AAG GAA AAA       720
Gly Gly Gly Gly Gly Asp His Asp His Gly Leu Ser Ser Lys Glu Lys
```

```
                225                 230                 235                 240
TAC GAG CAG CAC AAG ATC ACC AGT TAC CTG ACG TCC AAA GGT GGA TCG    768
Tyr Glu Gln His Lys Ile Thr Ser Tyr Leu Thr Ser Lys Gly Gly Ser
                    245                 250                 255

GGC GGC GGC GGA GGA GGA GGA GGC GGC GGT TTG GAT CGC AAC TCC GGC    816
Gly Gly Gly Gly Gly Gly Gly Gly Gly Gly Leu Asp Arg Asn Ser Gly
                260                 265                 270

AAT TAC TTC AAC GAC GCG AAA GAG GAG AGC GAC AGC GAG GAT TCT GTA    864
Asn Tyr Phe Asn Asp Ala Lys Glu Glu Ser Asp Ser Glu Asp Ser Val
                    275                 280                 285

ACG TTC GAG TTC GTC CCT AAC ACC AAG AAG CAA AAG TGC GGC            906
Thr Phe Glu Phe Val Pro Asn Thr Lys Lys Gln Lys Cys Gly
                290                 295                 300

(2) INFORMATION FOR SEQ ID NO:4:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO:4:

Thr Pro Thr Pro Val Asn Pro Ser Thr Ala Pro Ala Pro Ala Pro Thr
1               5                   10                  15

Pro Thr Phe Ala Lys Leu Gln Glu Phe Gly Ser Ser Pro Gln Lys Ser
                20                  25                  30

Gly Thr Gly Pro Gln Pro Gly Ser Ala Gly Met Gly Gly Ala Lys Thr
            35                  40                  45

Pro Ser Asp Ala Val Gln Asn Ile Leu Gln Lys Ile Glu Lys Ile Lys
        50                  55                  60

Asn Thr Glu Glu Leu Gln Glu Phe Thr Ala Asn Asn Arg Val Ser Phe
65                  70                  75                  80

His Gly Val Lys Asn Met Arg Ile Asn Val Gln Leu Lys Asn Phe Tyr
                85                  90                  95

Gln Thr Leu Leu Asn Cys Ala Val Thr Lys Leu Pro Cys Thr Leu Arg
                100                 105                 110

Ile Val Thr Glu His Asp Thr Leu Leu Tyr Val Ala Ser Arg Asn Gly
            115                 120                 125

Leu Phe Ala Val Glu Asn Phe Leu Thr Glu Pro Phe Gln Arg Gly
        130                 135                 140

Asp Pro Phe Asp Lys Asn Tyr Val Gly Asn Ser Gly Lys Ser Arg Gly
145                 150                 155                 160

Gly Gly Gly Gly Gly Ser Leu Ser Ser Leu Ala Asn Ala Gly Gly
                165                 170                 175

Leu His Asp Asp Gly Pro Gly Leu Asp Asn Asp Leu Met Asn Glu Pro
            180                 185                 190

Met Gly Leu Gly Gly Leu Gly Gly Gly Gly Gly Gly Gly Lys Lys
        195                 200                 205

His Asp Arg Gly Gly Gly Gly Ser Gly Thr Arg Lys Met Ser Ser
        210                 215                 220

Gly Gly Gly Gly Gly Asp His Asp His Gly Leu Ser Ser Lys Glu Lys
225                 230                 235                 240

Tyr Glu Gln His Lys Ile Thr Ser Tyr Leu Thr Ser Lys Gly Gly Ser
                245                 250                 255

Gly Gly Gly Gly Gly Gly Gly Gly Gly Gly Leu Asp Arg Asn Ser Gly
```

```
                260                 265                 270
Asn Tyr Phe Asn Asp Ala Lys Glu Glu Ser Asp Ser Glu Asp Ser Val
            275                 280                 285
Thr Phe Glu Phe Val Pro Asn Thr Lys Lys Gln Lys Cys Gly
        290                 295                 300
```

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: Peptide (xi) SEQUENCE DESCRIPTION: SEQ ID NO:5:

```
Lys Leu Gln Glu Phe
 1               5
```

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:6:

```
GAATTCACAG CCAATAACCG CGTCAGTTTC                                30
```

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:7:

```
AGGCGTCGGC GTGCCGCACT TTTGCTTCTT GGTGTT                         36
```

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:8:

```
CAAAAGTGCG GCACGCCGAC GCCTGTCAAT CCTTCC                         36
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

```
GAATTCCTAT TCCTCCGTGT TCTTAATCTT                                30
```

(2) INFORMATION FOR SEQ ID NO:10:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:10:

GGATAACAAT TGGGCATCCA GTAAGGAGGT                                                30

(2) INFORMATION FOR SEQ ID NO:11:

(i) SEQUENCE CHARACTERISTICS:
            (A) LENGTH: 106 base pairs
            (B) TYPE: nucleic acid
            (C) STRANDEDNESS: single
            (D) TOPOLOGY: linear (xi) SEQUENCE DESCRIPTION: SEQ ID NO:11:

AGGATGCGGA TCCCCGATCT CGACCCGTCG ACGAATTCGA GCTCGGTACC CGGGGATCCT               60

CTAGACTGCA GGCATGCTAA GTAAGTAGAT CGGGAATTCA CATCCG                             106

(2) INFORMATION FOR SEQ ID NO:12:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:12:

CCCGCGCGCT ACGCGTCGAC GCGTCTGCCC                                                30

(2) INFORMATION FOR SEQ ID NO:13:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:13:

CCCGCGCGCT ACGCGACGTC GCGTCTGCCC                                                30

(2) INFORMATION FOR SEQ ID NO:14:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:14:

Pro Ala Arg Tyr Ala Ser Thr Arg Leu Pro
1               5                   10

(2) INFORMATION FOR SEQ ID NO:15:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:15:

```
Pro Ala Arg Tyr Ala Thr Ser Arg Leu Pro
1               5               10
```

RECOMBINANT MONO AND POLY ANTIGENS TO DETECT CYTOMEGALOVIRUS-SPECIFIC IGM IN HUMAN SERA BY ENZYME IMMUNOASSAY

TECHNICAL FIELD

The present invention relates to recombinant proteic materials useful as mono- and poly-epitope artificial antigens able to detect HCMV-specific immunoglobulines in Human sera, especially IgM, in place of purified virions. In particular, the invention relates to the joint use of three different fusion proteins obtained by recombinant methods, a first one including high immunogenic epitopes both from the non structural, DNA-binding viral protein of 52 kD (pp52) and from the structural phosphoprotein of 150 kD (pp150), a second one including an immunogenic epitope from the major matrix protein of the Human Cytomegalovirus (HCMV), namely the viral protein of 65 kD (pp65) encoded by the viral gene UL83, and a third one including an immunogenic epitope from the assembly protein of 38 kD (pp38) encoded by the viral gene UL80a. The invention further relates to a diagnostic kit and to diagnostic reagents derived therefrom and to plasmids expressing said recombinant antigens.

BACKGROUND ART

Human Cytomegalovirus (HCMV) is a ubiquitous herpesvirus in man. It is rarely pathogenic in healthy adults but is associated with several diseases in immunocompromised individuals (such as HIV-infected people and transplant recipients). Furthermore, HCMV is the most common cause of congenital infection in humans. Intrauterine primary infections are second only to Down's syndrome as a known cause of mental retardation. Less severe complications are the result of secondary infections. As infections are either asymptomatic or accompanied by symptoms that are not specific of HCMV (such as fever and leukopenia), laboratory techniques are the sole means of diagnosing acute HCMV infection. Diagnosis of HCMV infection can be obtained by direct demonstration of the virus or virus components in pathological materials or indirectly through serology 111. Diagnosis of primary HCMV infection is exclusively accomplished by serological methods, i.e. demonstration of the appearance of antibodies to HCMV in a previously seronegative subject. HCMV-specific IgM is a sensitive and specific indicator of primary HCMV infection in immunocompetent subjects while it is very often produced during active viral reactivation in transplant recipients [2–4]. However its detection varies widely and a very poor agreement has been found among the results obtained with different commercial kits [5].

From EP 262531 there are known immunogenic portions of HCVM structural phosphoprotein of 150 kD, encoded by the gene localized in the Hind III-Y/N fragment of the viral genome; according to said European patent, such immunogenic portions of pp150 are encoded, in particular, by an EcoRI-PstI fragment of approximately 1.5 kb, localized inside the region of EcoRi-Y fragment from HCMV genome of AD169 strain. Subsequent and more exhaustive studies have however shown the afore deductions to be incorrect, in that (FIG. 1), protein pp150 is shown to be encoded by UL32, much longer than 1.5 kb and, anyway, quite outside any such EcoRI-PstI fragment, as may be defined within the EcoRI-Y fragment of the AD169 strain. Furthermore, the EcoRI-Y fragment is wholly outside (in particular, to the side, towards the $NH_2$-terminus) of Hind III-Y/N fragment.

According to the Applicants, therefore, there is a correlation between the immunogenic properties shown by the proteic material referred to in the afore European patent (which, however, providing an incorrect identification of the polypeptide, causes it to remain substantially undetermined) and the inclusion into the peptide of epitope A1C2, encoded by UL32 nucleotides 1783 to 1842, running 5'→3', i.e., of the region corresponding to amino acids 595 to 614 of ppUL32, whose identification is posterior (Novak J. P. et al. 1991. Mapping of serologically relevant regions of human cytomegalovirus phosphoprotein pp150 using synthetic peptides. J. Gen. Virol. 72; 1409–1413).

Antigenic materials composed of single well characterized viral proteins, or portions of them, produced via molecular biology or peptide chemistry have proven to be promising tools in improving serological diagnosis [6–14]. The analysis of the humoral immune response elicited during natural infection has repeatedly shown that the basic phosphoprotein of 150 kD encoded by UL32 (ppUL32) [15] and localized in the viral tegument is highly immunogenic and is recognized by sera from nearly 100% of the HCMV-seropositive subjects tested [6, 16]. In this molecule at least two epitopes have been identified and shown to react efficiently with human immunoglobulins. In particular, the analysis of several ppUL32 fusion proteins showed that a region localized in the sequence between aa 1006 and aa 1048, inclusive, read in 5'→3' direction, of the molecule (aa 1006–1048) reacts with more than 80% of IgM-positive sera [9,11]. When chemically synthesized, another region localized between aa 595 and 614 gave a positive reaction with almost 100% of IgG-positive sera [17]. When expressed as recombinant protein this region has proven to react very efficiently also with HCMV-specific IgM [12]. The two coding regions were recently fused together and shown to produce a double epitope fusion protein which can replace the entire pp150 molecule in its IgM-binding ability [12].

Another HCMV protein which reacts very well with IgM is the non structural DNA-binding phosphoprotein of 52 kD [18] encoded by viral gene UL44 (ppUL44) [7, 11]. The COOH part of the molecule shows efficient IgM binding and does not contain relevant amino acid sequences cross-reacting with the homologous protein of other members of the Herpesviridae family (that are mainly present in the $NH_2$ half) [19]. The COOH half of this protein was expressed and tested with human sera. The DNA sequence expressing this region has been in fact inserted into plasmid p-ROS (which carries a truncated sequence of LacZ) at site SmaI and cloned into *E.coli*, thus obtaining a fusion protein H10, which has yielded good results [21].

Besides ppUL32 and ppUL44, two other HCMV proteins are well known: the major matrix phosphoprotein of 65 kD encoded by viral gene UL83 (ppUL83) and the assembly phosphoprotein of 38 kD encoded by the viral gene UL80a (ppUL80a). The first is known to induce a strong IgM response and antibodies reacting exclusively to this protein were described during primary infection [7]. Likewise, the IgM to this second protein are very often the first marker to be detected in HCMV seropositive transplanted patients undergoing a viral reactivation [Kraat et al. 1995, manuscript submitted]. Moreover, some of the Applicants observed a strong IgM reactivity to this protein in congenitally infected newborns (Lazzarotto and Landini, unpublished observation).

However, the above studies have not been successful, so far, in producing such recombinant proteic material, as are actually capable of replacing the virus or virus components (purified virions) in the diagnostic kits currently in use.

DISCLOSURE OF THE INVENTION

A primary object of the present invention is to provide a recombinant proteic material, in particular, a fusion protein, capable of binding by immunoreaction with antibodies produced against human Cytomegalovirus, in particular, both IgM and IgG, capable of being used as an antigen for detecting such antibodies in the relevant serologic tests, with substantially the same efficacy as the virus and/or of infected cell lyses.

A further object of the present invention is to furnish diagnostic reagents and kits derived from said proteic material.

A further object of the present invention is to provide a plasmid, capable of being inserted into a prokaryotes and/or eukaryotes host organism so as to express said recombinant proteic material as a fusion protein.

It is also an object of the present invention to provide recombinant antigens, in particular fusion proteins, to detect Cytomegalovirus-specific IgM in human sera by enzyme immunoassay.

A further object of the present invention is to furnish diagnostic reagents and kits derived from said proteic materials.

Finally, a further object of the present invention is to provide plasmids, capable of being inserted into a prokaryotes and/or eukaryotes host organism so as to express said recombinant proteic material as a fusion protein, in particular fused with CKS protein.

According to the present invention, there is provided a recombinant proteic material, capable of binding with antibodies against human Cytomegalovirus (HCMV), characterized in that it consists of a fusion protein comprising a first region, carrying at least part of the sequence between aa 202 and aa 434, inclusive, read in 5'→3' direction, of protein pp52, a second region, carrying at least a part of the sequence between aa 1006 and aa 1048, inclusive, read in 5'→3' direction, of pp150, and a third region, carrying at least a part of the sequence between aa 595 and 614 inclusive, in 5'→3' direction, of pp150; said regions capable of being variably arranged with respect to one another within the fusion protein.

Said regions preferably comprise said sequences of pp52 and pp150 in full, and, according to a preferred, non-limiting, embodiment, a fusion protein according to the invention comprises in a sequential manner, running 5'→3': said first region, immediately downstream wherefrom there is placed said third region, and then said second region, downstream from said third region, a bridge sequence being inserted between said third and second regions.

Said bridge sequence consists, running 5'→3', of the following series of aminoacids: lys leu gin glu phe (SEQ ID NO: 5).

The present invention further provides for a reagent for diagnosing HCMV infection by serological methods, characterized in that it comprises a fusion protein as defined hereinabove.

In particular, the diagnostic reagent comprises a fusion protein, whereof at least part of the aminoacids is encoded by the nucleotide sequence shown in the sequence listing as SEQ ID NO: 1, read from nucleotide 001 to nucleotide 900.

The present invention also relates to diagnostic reagents for direct detection of HCMV through serology, comprising at least one monospecific polyclonal serum or monoclonal antibodies (MaB), directed against said fusion protein.

Finally, the present invention relates to a plasmid, capable of being inserted into a prokaryotes or eukaryotes host organism, characterized in that it comprises, combined together, a first DNA sequence encoding at least part of the sequence between aa 202 to aa 434, inclusive, read in 5'→3' direction, of protein pp52 of HCMV, a second DNA sequence encoding at least part of the sequence between aa 1006 and aa 1048, inclusive, read in 5'→3' direction, of protein pp150, and a third DNA sequence encoding the aminoacid sequence, running 5'→3', between aa 595 and aa 614, included, of protein pp150.

In particular, said plasmid comprises either the nucleotide sequences shown in the sequence listing as SEQ ID NO: 1, from nucleotide 002 to nucleotide 907, or that shown as SEQ ID NO: 3.

Moreover, according to an improved aspect of the present invention, there is provided a mixture of recombinant antigens to detect Cytomegalovirus-specific IgM in human sera by enzyme immunoassay, the mixture being characterized in that it includes, in combination:

(i)—a first fusion protein comprising: a first region, carrying an amino acid sequence (H10) corresponding to at least part of the sequence between aa 202 and aa 434, inclusive, read in 5'→3' direction, of viral protein pp52; a second region, carrying an amino acid sequence (F3) corresponding to at least part of the sequence between aa 1006 to aa 1048, inclusive, read in 5'→3' direction, of viral protein pp150; and a third region, carrying an amino acid sequence (A1C2) corresponding to at least part of the sequence between aa 595 and aa 614 inclusive, read in 5'→3' direction, of the same viral protein pp150; said regions capable of being variably arranged with respect to one another within the first fusion protein;

(ii)—a second fusion protein comprising an immunogen region consisting in a sequence of amino acids corresponding to at least part of the sequence between aa 297 to aa 510, inclusive, read in 5'→3' direction, of the major matrix protein pp65 encoded by the viral gene UL83; and (iii)—a third fusion protein comprising an immunogen region consisting in a sequence of amino acids corresponding to at least part of the sequence between aa 117 to aa 373, read in 5'→3' direction, of the viral assembly protein pp38 encoded by the viral gene UL80a.

In particular, said regions include said aminoacid sequences of pp52, pp150, pp65 and pp38 in full, fused together with protein CKS or at least a part thereof.

The invention relates, furthermore, to a plasmid, capable of being inserted into a prokaryotes or eukaryotes host organism, characterized in that it comprises a DNA sequence encoding at least part of the sequence between aa 297 to aa 510, read in 5'→3' direction, of the HCMV major matrix protein pp65 encoded by the viral gene UL83, said sequence being linked at the 3'end of a second sequence corresponding to the sequence from aminoacid 1 to aminoacid 240 inclusive encoding for protein CKS.

The invention relates also to a further plasmid, capable of being inserted into a prokaryotes or eukaryotes host organism, characterized in that it comprises a DNA sequence encoding at least part of the sequence between aa 117 to aa 373, read in 5'→3' direction, of the HCMV assembly protein pp38 encoded by the viral gene UL80a, said sequence being linked at the 3'end of a second sequence corresponding to the sequence from aminoacid 1 to aminoacid 240 inclusive encoding for protein CKS.

Finally, the invention relates to the use of a mixture of mono- and poly-epitope fusion proteins to detect Cytomegalovirus-specific IgM in human sera by enzyme immunoassay, the mixture being characterized in that it includes, in combination:

(i)—a first fusion protein comprising: a first region, carrying an amino acid sequence (H10) corresponding to at least part of the sequence between aa 202 and aa 434, inclusive, read in 5'→3' direction, of viral protein pp52; a second region, carrying an amino acid sequence (F3) corresponding to at least part of the sequence between aa 1006 to aa 1048, inclusive, read in 5'→3' direction, of viral pp150; and a third region, carrying an amino acid sequence (A1C2) corresponding to at least part of the sequence between aa 595 and 614 inclusive, read in 5'→3' direction, of the same viral protein pp150; said regions capable of being variably arranged with respect to one another within the first fusion protein;

(ii)—a second fusion protein comprising an immunogen region consisting in a sequence of amino acids corresponding to at least part of the sequence between aa 297 to aa 510, inclusive, read in 5'→3' direction, of the major matrix protein pp65 encoded by the viral gene UL83; and (iii)—a third fusion protein comprising an immunogen region consisting in a sequence of amino acids corresponding to at least part of the sequence between aa 117 to aa 373, read in 5'→3' direction, of the viral assembly protein pp38 encoded by the viral gene UL80a.

The invention further relates to the use of the above mixture of fusion proteins to produce a diagnostic kit to detect Cytomegalovirus-specific IgM in human sera by enzyme immunoassay.

According to the first aspect of the present invention, starting from the studies on polyepitope fusion proteins of some of the Applicants [12], the content whereof is incorporated herein by reference, a series of clones have been prepared, operating with plasmid p-ROS, as according to the well known techniques described by Maniatis et al. (1982. Molecular cloning: a laboratory manual. Cold Spring Harbor Laboratory. Cold Spring Harbor, N.Y.); these clones, once inserted into *E. coli* and activated with IPTG, are capable of producing a whole range of fusion proteins comprising a portion of β-galactosidase (β-Gal), which were subsequently comparatively tested using the known techniques (Western blott, Immunoblott, ELISA, etc.) with HCMV-positive sera for HCMV-specific IgM and IgG from transplant recipients in order to ascertain their different detection levels.

In particular, there have been prepared a first plasmid, pMB28, capable of expressing amino acid sequence A1C2; a second plasmid, pGT1, capable of expressing a new immunogenic sequence F3 of ppUL32, comprising the last 44 aminoacids of COOH terminus of viral protein pp150 and encoded by UL32 nucleotides from 3013 to 3144, running 5'→3'; and a third plasmid, pMB34, capable of expressing A1C2 and F3 as a single fusion protein with β-Gal; said first plasmid having been obtained by inserting a modified and PCR amplified DNA fragment between sites SalI and HindIII of the polyclonation site of prokaryotes expression vector p-ROS according to Platchter et al. (1992. "Detection of cytomegalovirus . . . "; J. Clin. Microbiol. 30; 201–206); the second plasmid was obtained by inserting into site SmaI of p-ROS a DNA EcoRI fragment from a LambdaGT 11 clone, suitably altered by mutagenesis by means of vector p-Alter, so as to replace a STOP codon with a corresponding EcoRI site. The third plasmid was obtained from plasmid pMB28, inserting therein the same 78 bp (base pairs) EcoRI fragment encoding F3 used for pGT1 at site StuI, thus allowing, between said two DNA sequences encoding A1C2 and F3, for a bridge sequence consisting of five aminoacids: lys leu gin glu phe (K, L, Q, E and F, according to IUPAC). Moreover, the known, highly immunogenic epitope (H10) of viral protein pp52, consisting of the last 233 aminoacids of COOH terminus of the protein itself, has also been included in the comparison.

To this end, the nucleotide sequence H10, contained in the genome of phage Lambda GT11 between two closely arranged EcoRI restriction sites, immediately upstream from lacZ, is obtained according to the well known techniques described by Berg and Kaiser, by digestion with EcoRI; subsequently, the cohesive ends are caused to become blunt by a filling-in operation in the presence of DNA polymerase, wherein the adenine/thymine bases (A/T), unpaired, are paired with the complementary nucleotides. In the meantime, plasmid p-ROS is digested with SmaI, which causes its opening and linearization; then, EcoRI H10 fragment of Lambda GT11 and the open plasmid are incubated together in the presence of DNA lygase, thus causing fragment H10 to be inserted at the appropriate site SmaI provided for in p-ROS and a plasmid pGH10 to be formed. The latter is in turn inserted in *E.coli* by electrophoration and cloned.

Finally, a last "mixed" plasmid, comprising both DNA sequences encoding A1C2 and F3 and the one encoding H10 was prepared from the previous plasmids. To this end, a pair of oligonucleotides were synthesized for pGH10 and one for pMB34, respectively, their sequences allowing for them to be used for chain amplification with PCR of sequences H10 and A1C2-F3, respectively; said oligonucleotide pairs, containing sequences, capable of introducing suitable recognition sites for given restriction enzymes (in the case in point, EcoRI) at 5' ends, and sequences in common between 5' and 3' of H10 and A1C2-F3, respectively at opposite ends, were used for amplifying a single DNA fragment containing said three epitopes, already in the desired reading frame and ready for cloning at the target sites of the expression vector, in the case in point, at the SmaI site of pROS for the epitopes to be expressed as fusion protein with β-Gal; in the last analysis, the resulting plasmid, pMB40, therefore comprises, at site SmaI, DNA sequence SEQ ID NO: 1, corresponding to nucleotides 002 to 907, encoding a new fusion protein comprising, at the same time, both the most immunogenic known epitope of pp150 (A1C2) and the most immunogenic epitope of pp52 (H10), and the new immunogenic epitope of pp150 (F3), deriving from the addition of further 19 aminoacids to the known epitope of pp150, consisting of the last 25 aminoacids (sequence D1) at the COOH terminus of the said protein.

Surprisingly, said new fusion protein, H10/A1C2/F3, was found to have a much higher IgG and IgM reactivity than that obtainable by properly combining in one single test kit the proteins containing the three distinct epitopes. A synergic effect, therefore, takes place, probably owing to the fact that, arranging such epitopes, as are normally far off, close to one another on the same viral protein (A1C2 and F3 of ppUL32, for instance) or even on different proteins (such as H10 of ppUL44), causes conformational epitopes, likely to be present in the original complete viral proteins and/or on the virions, to be "mimicked".

The new fusion protein, comprising the said sequences, has indeed proven to be as active as the purified virions in binding with IgG and IgM of infected subjects, thus finally allowing for a standardized antigen, both as to quality and as to quantity, capable of actually replacing purified virions and/or infected cells in the preparation of diagnostic kits for HCMV infection serodiagnosis. Obviously, the previously described epitopes may be included into the new fusion protein as according to the present invention in the order of sequence SEQ ID NO: 2, currently preferred, or else in any other sequence, also allowing for bridge sequences to be inserted between them, like that corresponding to nucleosides 757 to 771 of SEQ ID NO: 1.

Plasmid pMB40, expressing such a protein, can be inserted into a prokaryotes host organism, such as E.coli. Besides, the specific method described for obtaining the "mixed" fragment further allows for its cloning in a different vector, in particular, after digestion with EcoRI, at the corresponding site of vector pHIL-S1, thus obtaining plasmid pHIL-D1, which allows for the recombinant protein to be expressed in Pichia pastoris, fused with a short peptide representing a secretion signal outside the yeast cell, in the culture medium. Such a manner of expression allows, among other things, for fusion protein production to be induced by the addition of methanol, instead of IPTG, as used for the expression in E.coli., thus representing a far less expensive method. Consequently, production of the poly-epitope fusion protein as according to the present invention can be large-scale, simple and economical.

According to a further aspect of the present invention, and starting from the results described above, the poly-epitope protein according to the first aspect of the invention has been further studied arranging the said regions in a different way and combining said recombinant material, expressed fused toghether with protein CKS, with immunogenic regions of other HCMV proteins, so obtaining a mixture of fusion proteins high effective against IgM.

The fusion proteins according to the present invention can be used alone or, according to the main aspect of the present invention, mixed together, for direct preparation of diagnostic reagents for serological detection of HCMV-specific antibodies, in that their ability of efficiently binding anti-HCMV IgM, in particular those produced during a primary asymptomatic phase of the infection, is substantially 100%. Such reagents may comprise the mixture of fusion proteins according to the invention, eventually in combination with other HCMV antigens, or else more complex fusion proteins, including the immunogenic sequences repeated many times and anyway in combination with one another.

The proteic materials represented by the fusion proteins according to the present invention can be further used for the preparation, by means of known techniques, of diagnostic reagents for serological detection of human Cytomegalovirus and/or antigens for the detection thereof represented by specific polyclonal sera, or by monoclonal antibodies (MaB) directed against the proteins of the invention and obtained via a number of different methods.

Said diagnostic reagents, containing the proteins according to the present invention, can be used, in turn, for the production of diagnostic kits for the demonstration, by serological methods, of the appearance of antibodies to human Cytomegalovirus (HCMV), wherein the reagent is adsorbed on nitrocellulose paper (blotting). Finally, the proteins according to the present invention can be used, after being purified, in ELISA assays, latex agglutination tests, RIA, as well as in all known serological screening methods for the presence of HCMV-specific IgG and IgM, both manual and partially or completely automized.

BRIEF DESCRIPTION OF THE DRAWINGS

FIGS. 6 and 7 show two tables comparing experimental data relating to the detection of IgG and IgM from HCMV-infected subjects, by ELISA assay, using the entire virus or different recombinant fusion proteins, including one according to a first aspect of the present invention;

FIG. 13A shows preparation of PCR fragments containing the A1C2F3 and H10 DNA sequences;

FIG. 13B shows preparation of PCR fragments containing the pp65(297-510aa) and pp38(117-373aa) DNA sequences;

FIGS. 14B, C, D show respectively: the nucleotide sequence of the plasmid pJO200, including the intended modification site at plasmid residues 151 to 180 (5'→3'); the double-stranded structure of the mutagenic oligonucleotide, 5'CGCGACGT3', synthesized for ligation into plasmid pJO200/MIuI/CIAP; and the nucleotide sequence of the plasmid pJO200ΔMIuI, including the modified residues 151 to 180 (5'-3');

FIG. 16A shows the preparation of PCR fragments containing the A1C2F3-H10, pp65(297-510aa), and pp38(117-373aa) DNA sequences;

FIG. 16B is a schematic representation of the construction of: plasmid pCMV-27:CKS-A1C2F3-H10-CKS, plasmid pCMV-28:CKS-pp65(297-510aa)-CKS, and plasmid pCMV-29:CKS- pp38(117-373aa)-CKS;

FIGS. 18 to 25 show tables comparing experimental data relating to the detection of IgM by EIA.

BEST MODE OF CARRYING OUT THE INVENTION

Figure 1:
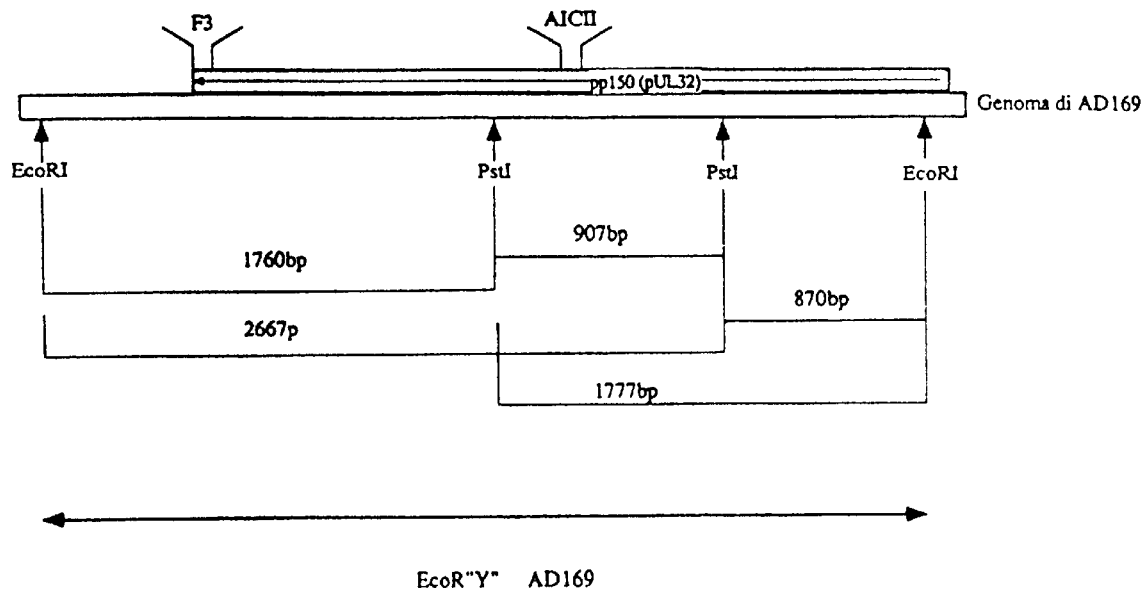
FIG. 1 illustrates schematically the position of the DNA fragments encoding two of the portions characterizing one of the fusion proteins according to the invention, in gene UL32 contained in EcoRI-Y fragment of the virus strain AD169.

The present invention will be better described by way of non-limiting examples thereof, with reference to the accompanying drawings.

EXAMPLES

REAGENT, ENZYMES AND CULTURE MEDIUM—Restriction enzymes, T4 DNA ligase, calf Intestinal alkaline phosphatase (CIAP), polynucleotide kinase, and the Klenow fragment of DNA Polymerase I were purchased from New England Biolabs, Inc., Beverly, Mass. or from Boehringer Mannheim Corp., Indianapolis, Ind. DNA and Protein molecular weight standards, Dalichi pre-cast gradient polyacrylamide gels, and Semi-Dry Blotting System with buffers were obtained from Integrated Separation Systems, Inc., Natick, Mass. Isopropyl-β-D-thiogalactoside (IPTG), acrylamide, N-N'-methylene-bis-acrylamide. N, N,N',N'-tetramethylethylenediamine (TEMED), 4-chloro-1-napththol, and sodium dodecylsulfate (SDS) were purchased from BioRad Laboratories, Richmond, Calif. Horseradish peroxidase (HRPO)- labeled antibodies were purchased from Kirkegeard & Perry Laboratories Inc. Gaithersburg, Md. "*EPICUREAN COLI* XL-1 Blue" (recA1, endA1, gyrA96, thi-I, hsdR17, supE44, relAl, lac [F'proAB lal$^q$ZdM15 Tn10 (Tet')]) Supercompetent *E. coli* cells, DNA isolation kit, RNA isolation kit, and ZAP-cDNA Synthesis kit were obtained from Stratagene Cloning Systems Inc. La Jolla, Calif. GeneAmp reagent kit and AmpliTaq DNA Polmerase were purchased from Perkin-Elmer Cetus, Norwalk, Conn. Nucleotide kit for DNA sequencing with Sequenase and 7-deaza-dGTP and Sequenase version 2.0 DNA Polymerase were obtained from U.S. Biochemical Corp., Cleveland, Ohio. PolyA+ mRNA purification kit was purchased from Pharmacia LKB Biotechnology Inc., Piscataway, N.J. Luria Broth plates with ampicillin (LiSamp plates) were purchased from Micro Diagnostics, Inc., Lombard, Ill. "OPTI-MEM" Medium, fetal calf serum, phosphate-buffered saline (PBS), competent *E.coli* DH5α (F$^-$ φ80dlacZdM15 d(lacZYA-arqF)U169 deoR recAl endAl phoA hsdR17 supE44 λ$^-$ thi-1 gyrA96 relA1), and "ULTRAPURE" agarose were purchased from GIBCO BRL, Inc., Grand Island, N.Y. Bacto-Tryptone, Bacto-Yeast Extract, and Bacto-Agar were obtained from Difco Laboratories, Detroit, Mich. "NZY" Broth was purchased from Becton Dickinson Microbiology Systems, Cockeysville, Md. Salmon Sperm DNA, lysozyme, ampicillin, N-lauroyl sarcosine, thimerosal, buffers, casein acid hydrolysate, urea, surfactants, like "TWEEN 20", diethylpyrocarbonate (DEPC), and inorganic salts were purchased from Sigma Chemical Co., St. Louis, Mo. "SUPER-BROTH II" contained 11.25 g/L tryptone, 22.5 g/L yeast extract, 11.4 g/L potassium phosphate dibasic, 1.7 g/L potassium phosphate monobasic, 10 ml/L glycerol, adjust pH to 7.2 with sodium hydroxide. Tris-buffered saline (TBS) consisted of 20 mM Tris, 150 mM NaCl, pH 7.5. Tris-buffered saline "TWEEN 20" consisted of TBS+0.05% "TWEEN 20". Membrane blocking solution consisted of 1% Bovine Serum Albumin, 1% Casein acid hydrolysate, 0.05% "TWEEN 20" in TBS. Rubazyme specimen dilution buffer (Rubazyme SDB) consisted of 100 mM Tris, pH 7.5, 135 mM NaCl, 10 mM EDTA, 0.2% "TWEEN 20", 0.01% thimerosal, and 4% bovine calf serum. Rubazyme conjugate diluent dilution buffer consisted of 100 mM Tris, pH 7.5, 135 mM NaCl, 0.01% thimerosal, and 10% bovine calf serum. "HRP" color development solution consisted of 0.06% 4-chloro-1-napththol, 0.02% $H_2O_2$, and 0.2% methanol in TBS. SDS-PAGE loading buffer consisted of 62 mM Tris, pH 6.8, 2% SDS (Sodium Dodecyl Sulphate), 10% glycerol, 5% β-mercaptoethanol, and 0.1% bromophenol blue. TE buffer consisted of 10 mM Tris, 1 mM EDTA, pH 8.0.

VIRUS PROPAGATION AND PREPARATION OF cDNA—CMV strain AD169 and Towne were propagated in human fibroblasts grown in "OPTI-MEM" Medium supplemented with 5% fetal calf serum. After 6 days post-infection, the infected cells were harvested by centrifugation, washed with PBS, and homogenized with a glass-PTFE ("TEFLON") homogenizer. Total viral DNA was isolated as described in Mocarski, E. S. et al. Proc.Nat.Acad.Sci 82:1266, 1985. Total RNA was isolated from the homogenized cells using the RNA Isolation Kit (Stratagene Cloning Systems, La Jolla, Calif.) and polyA+RNA was isolated using a mRNA Isolation Kit (Pharmacia Biotech, Piscataway, N.J.). HCMV cDNA was synthesized from the purified viral mRNA using a "ZAP-cDNA" Synthesis Kit (Stratagene Cloning Systems, La Jolla, Calif.).

GENERAL METHODS—All enzyme digestions of DNA were performed according to suppliers' instructions. At least 5 units of enzyme were used per microgram of DNA, and sufficient incubation time was allowed for complete digestion of DNA. Supplier protocols were followed for the various kits used in manipulation of DNA and RNA, and also for PCR and sequence of DNA. Standard procedures were used for (1) small scale preparation and large scale preparation of plasmid DNA from *E. coli*, (2) preparation of phage lysate DNA from *E. coli* cells infected with phage λ, (3) preparation of phage lysates for the absorption of anti-*E.coli* antibodies, (4) extraction with phenol-chloroform, (5) precipitation of DNA with ethanol, (6) restriction analysis of DNA on agarose gels, (7) purification of DNA fragments from agarose and polyacrylamide gels, (8) filling the recessed 3' termini created by digestion of DNA with restriction enzymes using the Klenow fragment of DNA Polymerase I, (9) ligation of DNA fragments with T4 DNA ligase, and (10) preparation of competent *E.coli* TB1 cells (F$^-$ ara d(lac-proAB) rpsL φ80dlacZdM15 hsdR17) as described in Sambrock, Fritsch, and Maniatis, Molecular Cloning: A Laboratory Manual, 2nd ed., New York: Cold Spring Harbor Laboratory Press 1989, the content of which is hereby incorporated by reference. The DNA fragments for cloning into plasmids that were generated by PCR amplification were extracted with phenol-chloroform and precipitated with ethanol prior to restriction enzyme digestion of the PCR reaction mixture. Oligonucleotides for PCR and DNA sequencing were synthesized on an Applied Biosystems Oligonucleotide Synthesizer, model 380B or 394, per manufacturer's protocol.

Example 1

Construction of lacZ-H10 Expression Vector pROSH10

Figure 2:
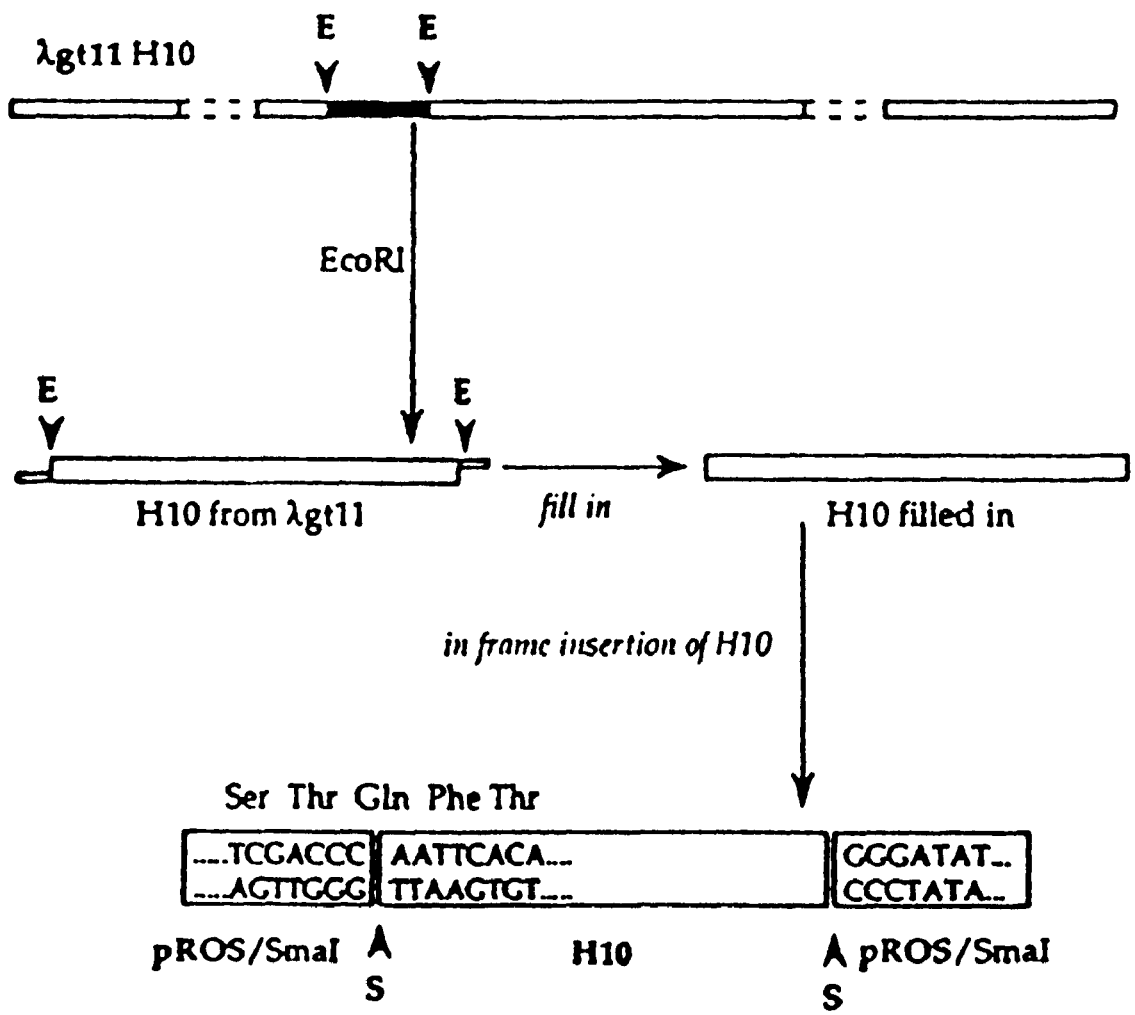

Operating with recombinant DNA standard methods, as described by Maniatis et al. (1982. Molecular cloning: a laboratory manual. Cold Spring Harbor Laboratory. Cold Spring Harbor, N.Y.) and from plasmids pROS supplied by the authors thereof (cf. Ellinger et al.), the genome of a clone, obtained from early gene expressing phage Lambda Gt11, which produces a fusion protein with β-galactosidase, highly reactive with CMV-positive sera, was purified. The genoma was then digested with restriction enzyme EcoRI to extract the DNA fragment expressed by the phage. The fragment was then cloned into vector pUC18 and sequenced. The sequence represented a fragment of 699 base pairs expressing 233 aminoacids at COOH terminus of pp52 (UL44). The fragment was then cloned at site SmaI of expression vector pROS, after filling in the EcoRI ends of the fragment, as illustrated schematically in FIG. 2. The plasmid so obtained was named pROSH10.

Example 2

Construction of lacZ-F3 Expression Vector pGT1

Operating with the methods described in Example 1, the genome of a clone, obtained from early gene expressing phage Lambda Gt11, which produces a fusion protein with β-galactosidase, highly reactive with CMV-positive sera, was purified. The genoma was then digested with restriction enzyme EcoRI to extract the DNA fragment expressed by the phage. The fragment was then cloned into vector pUC18 and sequenced. The sequence represented a fragment of 132 base pairs expressing 44 aminoacids at COOH terminus of p150 (UL32). The fragment was then cloned at site SmaI of expression vector pROS, after filling in the EcoRI ends of the fragment, as illustrated schematically in FIG. 2 referred to Example 1. The plasmid so obtained was named pGT1.

Example 3

Construction of lacZ-A1C2F3 Expression Vector pMB34

The plasmid pMB34 is a derivative of the lacZ expression vector pROS described in Ellinger et al., J. Clin. Micro. 27: 971, 1989. This vector contains a truncated form of the lacZ gene (1–375 amino acids) with a polylinker cloning site located downstream of the lacZ gene. The pMB34 plasmid was constructed in two steps by joining two regions of ppUL32, which encodes the basic phosphoprotein of 150 kD of HCMV, to the 3' end of the lacZ gene in pROS.

A. Construction of pMB28: lacZ-A1C2

Figure 3:
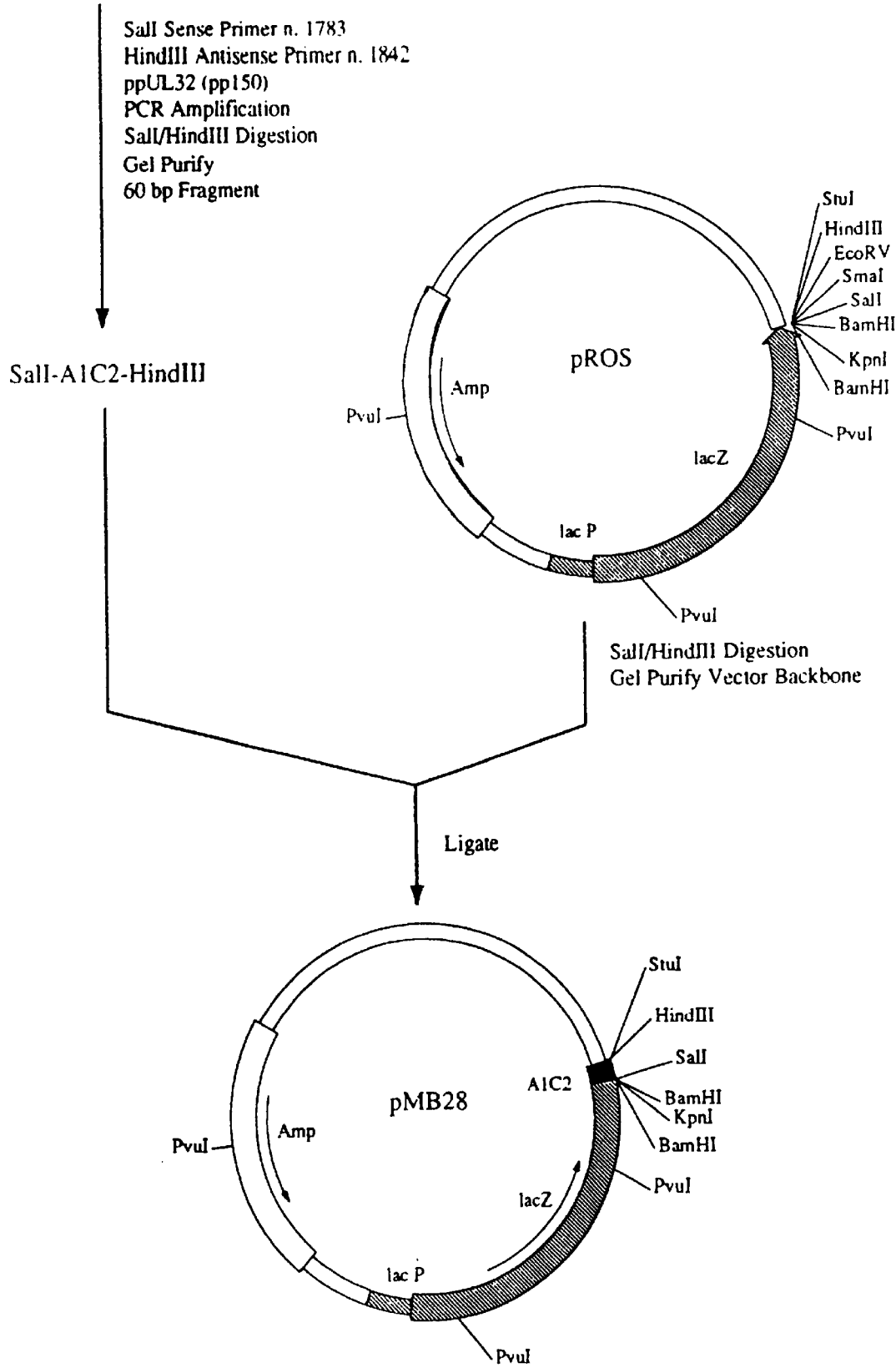
FIGS. 3 and 4 are schematic representations of the construction of plasmids pMB28: lacZ-A1C2 and pMB34:lacZ-A1C2F3.

The plasmid pMB28 is a derivative of plasmid pROS as shown in FIG. 3. This plasmid was constructed by cloning a DNA fragment containing HCMV-A1C2, obtained by PCR amplification of Human Cytomegalovirus (HCMV) genomic DNA from the region of ppUL32 encoding amino acids 595–614 of pp150 (nucleotides 1763–1842), into the polylinker region of pROS. Large scale plasmid DNA (pROS) was isolated from DH5α cells operating as described in general methods. Plasmid pROS was digested with SalI and HindIII and the vector backbone was purified on an agarose gel. A sense primer starting at nucleotide 1783 of ppUL32 containing a SalI site and an antisense primer starting at nucleotide 1842 of ppUL32 containing a HindIII site were synthesized and added to a PCR reaction mixture containing genomic HCMV DNA. After PCR amplification, the reaction mixture was digested with SalI and HindIII, and the 60 base pair fragment containing A1C2 (nucleotides 1733–1842) was purified on an agarose gel. This purified fragment was then ligated to purified pROS/SalI/HindIII overnight at 16° C. The next day the ligation mixture was transformed into competent DH5α cells. Small scale preparation DNA was prepared from the transformants and screened for the presence of the 60 base pair fragment in pROS at the end of the lacZ gene. Plasmid pMB28, which contains the A1C2 fragment, was isolated. The DNA sequence of A1C2 in pMB28 was confirmed and the A1C2 coding region was in frame with the lacZ coding sequence.

B. Construction of pMB34: lacZ-A1C2F3

Figure 4:
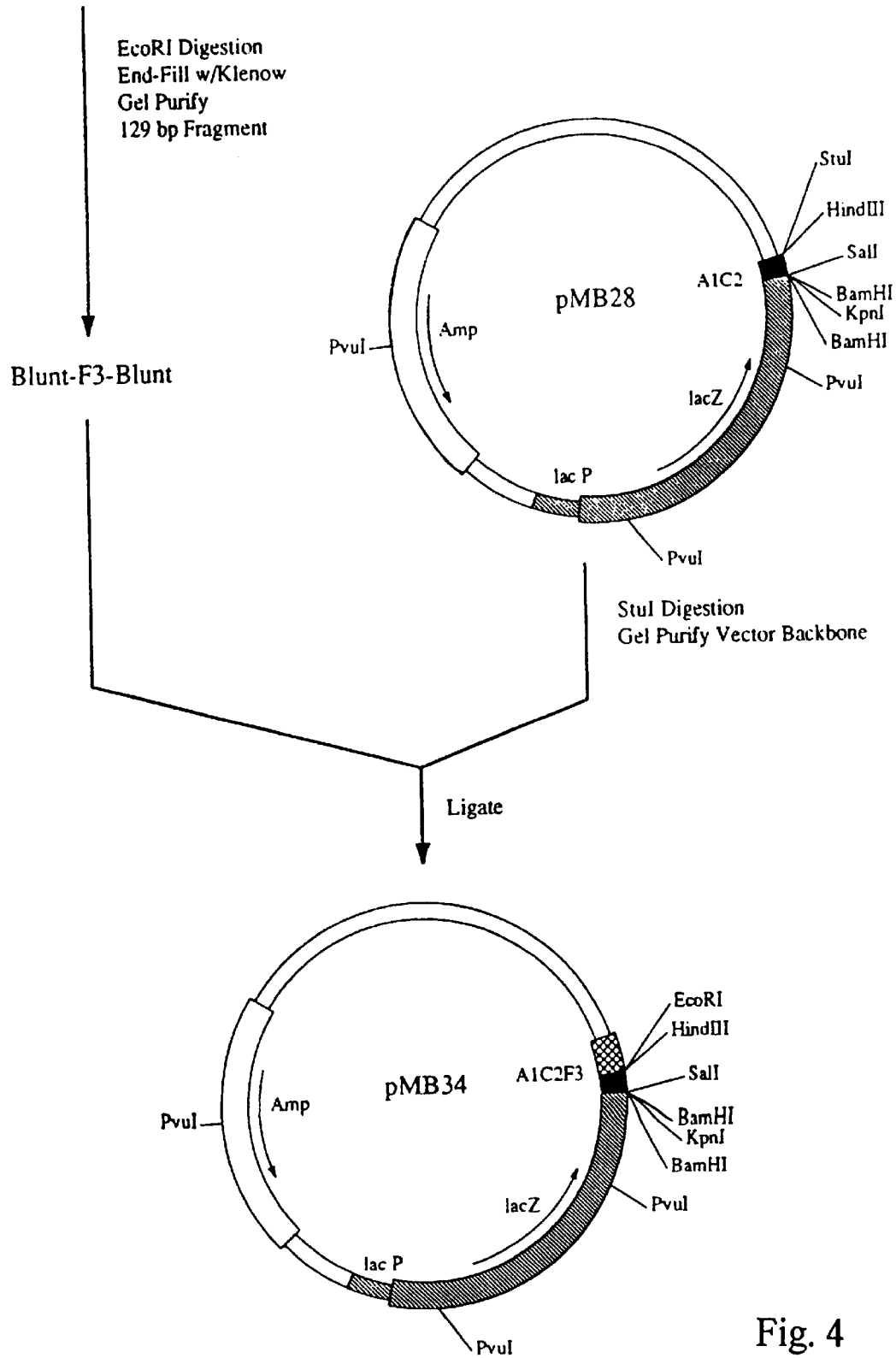

The plasmid pMB34 is a derivative of plasmid pMB28, as shown in FIG. 4. The plasmid pMB34 was constructed by cloning a DNA fragment, containing HCMV-F3 obtained from a λgt11 subclone of ppUL32 encoding amino acids 1006–1043 of ppUL32 (nucleotides 3016–3144) derived from the λgt11 library of Mocarski, E. S. et al. Proc. Nat. Acad. Sci 82: 1266, 1985, into the polylinker region of pMB28 just downstream of the A1C2 DNA sequence. Large scale plasmid DNA (pMB28) was isolated from DH5α cells as described in general methods. Phage lysate DNA was prepared from phage λgt11 clone λ-F3 as described in general methods. Plasmid pMB28 was digested with StuI and the vector backbone with blunt-ends was purified on an agarose gel. Phage λ-F3 DNA was digested with EcoRI and the recessed 3' termini were filled in with the Klenow fragment of DNA Polymerase I, leaving blunt-ends. The blunt-ended 129 base pair λ-F3 fragment was purified on an agarose gel and then blunt-end ligated to pMB28/StuI overnight at 16° C. The next day the ligation mixture was transformed into competent DH5α cells. Small scale preparation DNA was prepared from the transformants and screened for the presence of the 129 base pair fragment in pMB28 at the end of the lacZ gene in the correct orientation. Plasmid pMB34, which contains the F3 fragment in the correct orientation, was isolated. The DNA sequence of F3 in plasmid pMB34 was confirmed and the F3 coding region was in-frame with the lacZ-A1C2 coding sequence. The coding region of the lacZ-A1C2F3 construct in pMB34 contains a bridge of 5 amino acids between A1C2 and F3 as shown below using the International Standard one-letter Codification for amino acids (according to which: L is Leu, Q is Gln, K is Lys, E is Glu, F is Phe):

(1) lacZ(1-375aa)A1C2(595-614aa,pp 150)K-L-Q-E-F-F3(1006-1048aa,pp 150)

Example 4

Construction of lacZ-H10A1C2F3 Expression Vector pMB40

Figure 5:
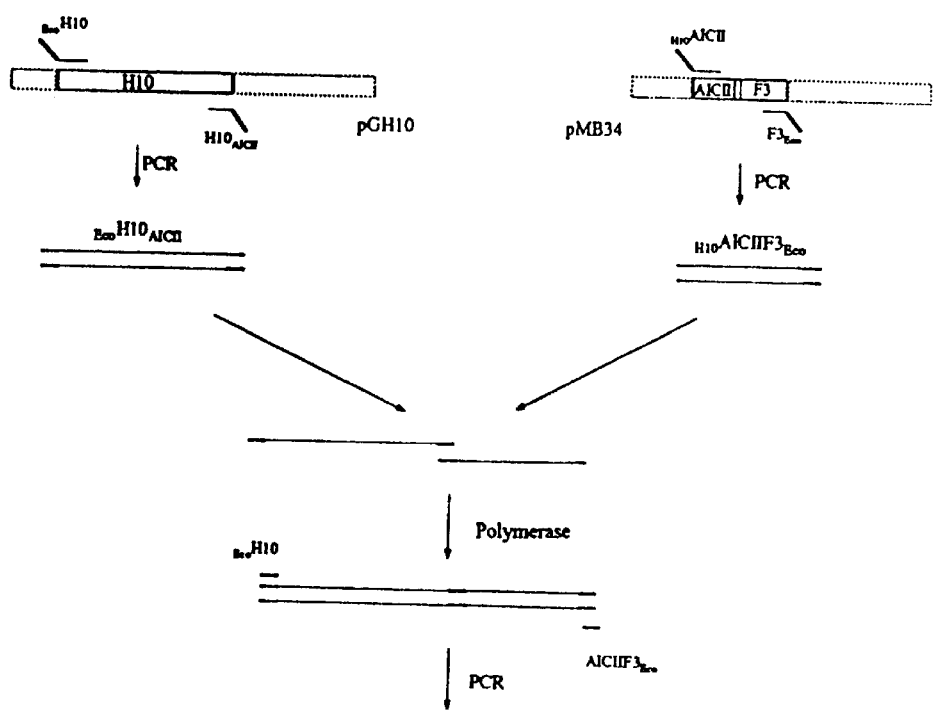
FIGS. 2 and 5 schematically illustrates methods for preparing plasmids used in the invention.

Starting from the previously described plasmids, and operating with such methods, as have been described in Examples 1, 2 and 3 hereinabove and as illustrated in FIG. 5, two pairs of oligonucleotides were synthesized, the sequences whereof allow for their use for chain amplification, with PCR, of H10 and A1C2-F3 sequences, respectively, localized in plasmids pGH10 and pMB34. The oligonucleotide sequences composing said primers are as follows:

$_{Eco}$H10: GAA TTC ACA GCC AAT AAC CGC GTC AGT TTC (SEQ ID NO: 6);

H10$_{A1C2}$: AGG CGT CGG CGT GCC GCA CTT TTG CTT CTT GGT GTT (SEQ ID NO: 7)

to amplify H10 from pGH10, introduce a site EcoRI in 5' in the amplified sequence and a sequence of 12 base pairs, homologous of A1C2, in 3' in the amplified fragment; and $_{H10}$A1C2: CAA AAG TGC GGC ACG CCG ACG CCT GTC AAT CCT TCC (SEQ ID NO: 8);

F3$_{Eco}$: GAA TTC CTA TTC CTC CGT GTT CTT AAT CTT (SEQ ID NO: 9)

to amplify A1C2-F3 fragment from plasmide pMB34, introducing in the amplified product, at 5', a sequence, homologous of H10, and an EcoRI site in 3'.

The two fragments, resulting from said two independent amplifications ($_{Eco}$H10$_{A1C2}$ and $_{H10}$A1C2-F3$_{Eco}$) were then mixed, together with external primers $_{Eco}$H10 and F3$_{Eco}$, and subjected to additional amplification. Owing to sequences 3'$_{Eco}$H10A1C2 and 5'$_{H10}$A1C2-F3$_{Eco}$ being complementary, the amplified product contains all three epitopes and has an EcoRI site at each end.

The amplified sequence was then cloned into pROS and the plasmid derived therefrom, named pMB40, includes, in connection with corresponding site SmaI, DNA sequence SEQ ID NO: 1, corresponding to nucleotides 002 to 907.

Example 5

The plasmids described in Examples 1 to 4 hereinabove, were inserted in E.coli, by electroporation and cloned; synthesis of the desired fusion protein was then induced by the addition of IPTG and the proteins so obtained were made competent by lysis of bacterial cells and denaturation of the cell lyses with SDS and β-mercaptoethanol; the proteins were then run in 9%–12% acrylamide gel with SDS-PAGE and then transferred to nitrocellulose, where immunoreactions took place; a preliminary screening of a number of serum samples was carried out by Miniblotter (Immunetics, Cambridge-Mass. USA); both IgG purified ("ENDOBULIN", of Immuno AG, Wien AT) and a group of IgM-highly positive sera were used at a dilution of 1:100. Individual human serum samples were diluted at 1:80 for IgG and IgM detection; a peroxidase-conjugated anti-g or anti-μ chain was used as a second antibody.

Two groups of human serum samples were used: the first group of sera consisted of seventeen HCMV-positive samples, eight whereof with a high IgG titre to HCMV and seven a medium/low level of HCMV-specific IgG, as detected by ELISA; the presence of HCMV-specific IgG was confirmed by immunoblotting. The second group of sera consisted of nineteen HCMV-positive samples, ten whereof with a high IgM titre to HCMV and nine a medium/low level of HCMV-specific IgM, as detected by ELISA; also in this case, the presence of HCMV-specific IgM was confirmed by immunoblotting.

The evaluation of anti-HCMV IgG was carried out with a CMV kit of M.A. Bioproducts (Walkersville, Md. USA); plates were read on a "microELISA" automatic reader (Dynatech Products, Alexandria, Va. USA). To perform linear regression analysis and to standardize the test run, every plate included three serum calibrators. The evaluation of anti-HCMV IgM was carried out with a CMV IgM "ELA" kit of Technogenetics (Hamburg, Germany). The results were interpreted as suggested by the manufacturers.

In order to avoid false positive results, all samples were also subjected to a test run for the detection of Rheumatoid factor by lattex agglutination (Rheuma-Wellco test of Wellcome, Dartford, Great Britain) and only the negative samples were used for comparison. Results are shown in Tables 1 and 2 of FIGS. 6 (IgG) and 7 (IgM).

As it is clear from the data presented, not only have the results obtained with H10/A1C2/F distinctly improved, as compared to those obtained with the other fusion proteins, both to IgG and to IgM, but they are fully superimposable to the results obtained with antigens composed of the entire virus.

Example 6

Construction of CKS Expression Vector pJO200

The CKS expression vector pJO200 allows the fusion of recombinant proteins to the CMP-KDO synthetase (CKS) protein. The DNA sequence for the structural gene encoding CKS (the kdsB gene) is published in Goldman et al., J. Biol. Chem. 261:15831, 1986. The amino acid sequence, 248 total, for CKS derived from the DNA sequence, is described in the same article. This pJO200 vector is constructed by a three-step procedure starting with the plasmid pTB201 (FIG. 8) described in Bolling and Mandecki, Biotechniques 8: 468, 1990. The construction plan for plasmid pJO200 involves the removal of two restriction enzyme sites and the addition of a multi-cloning site at the 3' end of the CKS gene. This was done to facilitate the cloning of HCMV (Human Cytomegalovirus) genes encoding protein antigens at the 3' end of CKS. The completed vector contains the coding sequence for 240 amino acids of the original kdsB gene plus an additional 20 amino acids at the end of the CKS gene contributed by the polylinker DNA sequence, for a total of 260 amino acids.

A. Construction of pJO210

The plasmid, pJO210, is a derivative of the CKS expression vector, pTB201. This plasmid was constructed by removing a single EcoRI site present in pTB201 located upstream from the promoter for the CKS gene. Large scale plasmid DNA (pTB201) was isolated from TB1 cells using the techniques described in the section above named "General Methods". The DNA was digested with EcoRI to completion and purified on a polyacrylamide gel. The purified pTB201/EcoRI fragment was then treated with the Klenow fragment of DNA Polymerase I in the presence of deoxynucleotide triphosphates. This enzyme fills in the recessed 3' termini produced after digestion with EcoRI, leaving blunt ends. After treatment with Klenow fragment, the DNA was phenol/chloroform extracted, ethanol precipitated, and resuspended in T4 DNA ligase buffer and ligated at room temperature with T4 DNA ligase for 4 hours. The ligation mixture was transformed into competent TB1 cells. Small scale preparation DNA was prepared from the transformants and screened for the loss of the EcoRI site. Plasmid pJO210, which has lost the EcoRI site, was isolated.

B. Construction of pJO215

Figure 8:
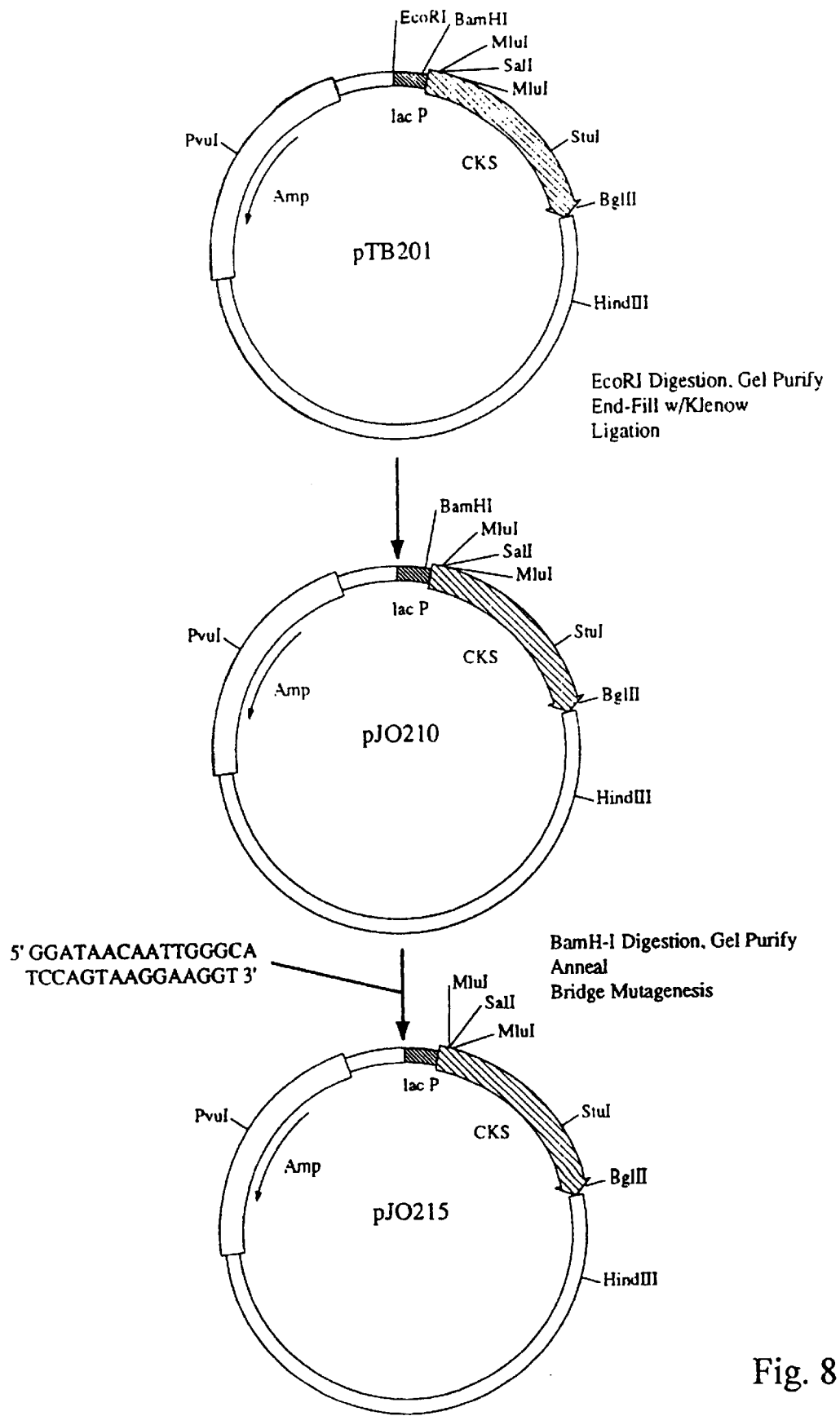
FIG. 8 is a schematic representation of the construction of plasmids JO210 and pJO215.

The plasmid pJO215 is a derivative of the plasmid pJO210 (FIG. 8). This plasmid was constructed by removing a single BamH-I site located in the promoter for the CKS gene using bridge mutagenesis (Mandecki, W., Proc. Nat. Acad. Sci. 837177,1986). Large scale plasmid DNA (pJO210) was isolated from TB1 cells as described in general methods. The DNA was digested with BamH-I to completion and purified on a acrylamide gel. The purified pJO210/BamH-I fragment was then mixed with the following mutagenic oligonucleotide:

(2) 5' GGATAACAAT TGGGCATCCA GTAAGGAGGT 3' (SEQ ID NO: 10)

which is complementary to one of the DNA strands of pJO210 in the region of the plasmid spanning the BamH-I site. This oligonucleotide contains a single base change, underlined, which will destroy the BamH-I site when incorporated into plasmid pJO210. After mixing the mutagenic oligonucleotide with pJO210/BamH-I, the mixture was boiled for 3 minutes, cooled to room temperature for 5 minutes and then transformed into competent TB1 cells. Small scale preparation DNA was prepared from the transformants and screened for the loss of the BamH-I site. Plasmid pJO215, which has lost the BamH-I site, was isolated.

C. Construction of pMC200

Figure 9:
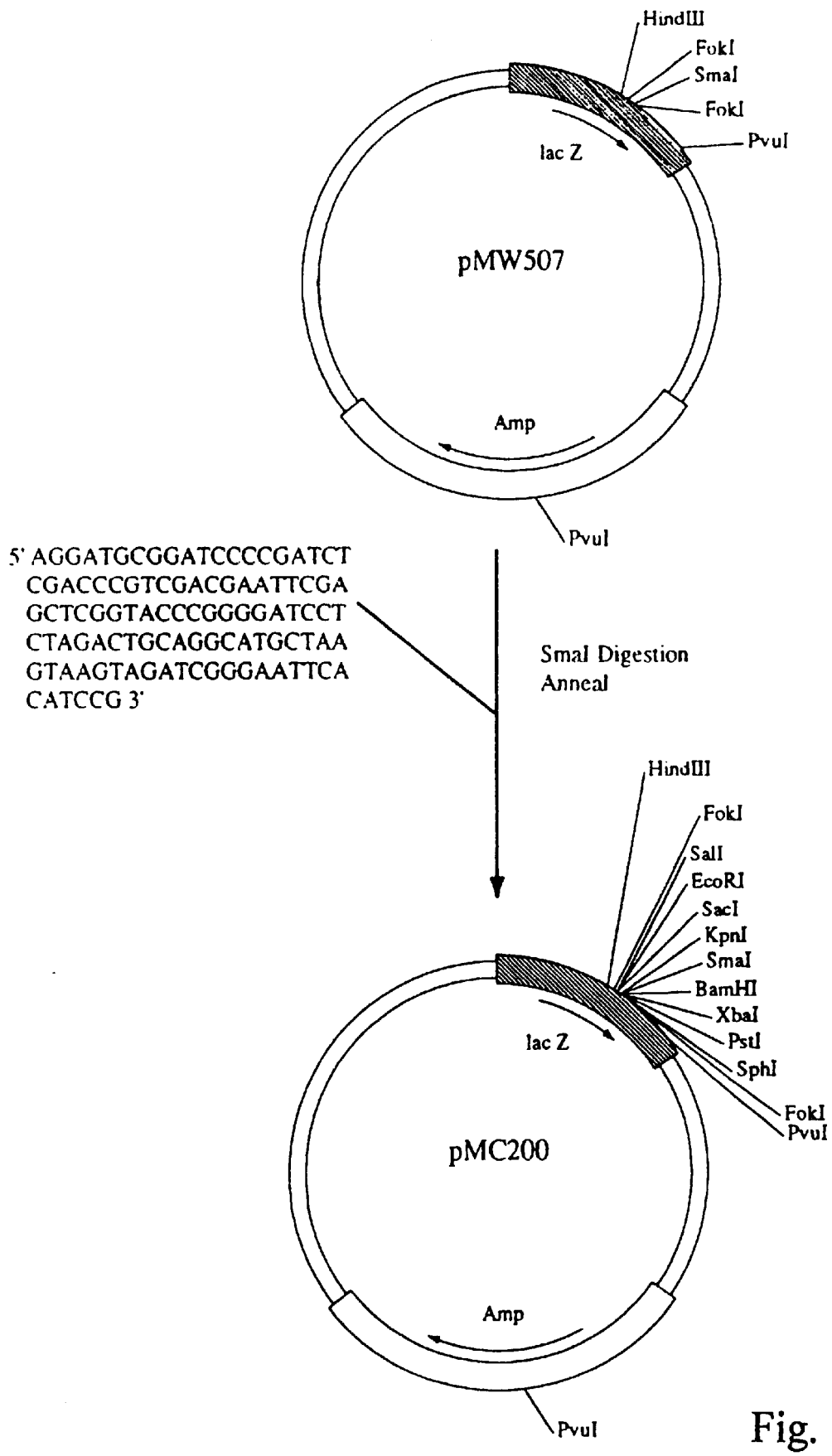
FIG. 9 is a schematic representation of the construction of plasmid pMC200.

The plasmid pMC200 is a derivative of plasmid pMW507 described in Mandecki and Bolling, Gene 68: 101, 1988 (FIG. 9). This plasmid was constructed by cloning a synthetic oligonucleotide containing a multi-cloning site into pMW507 using the FokI method of gene synthesis described by Mandecki and Bolling, 1988. Large scale plasmid DNA (pMW507) was isolated from TB1 cells as described in general methods. The DNA was digested to completion with SmaI and then mixed with the following oligonucleotide:

5' AGGATGCGGA TCCCCGATCT CGACCCGTCG ACGAATTCGA (3) GCTCGGTACC CGGGGATCCT CTAGACTGCA GGCATGCTAA GTAAGTAGAT CGGGAATTCA CATCCG 3' (SEQ ID NO: 11) which contains FokI arms at the end and several restriction enzyme sites, as follows:

5' FokI arm-BglII sticky end-SalI/AccI/HincII-EcoRI-SstI-KpnI-SmaI/XmaI-(4) BamH-I-XbaI-PstI-SphI-stop codons -BglII sticky end-FokI arm 3'

After mixing the oligonucleotide with pMW507/SmaI, the mixture was boiled for 3 minutes, cooled to room temperature for 5 minutes, and then transformed into competent TB1 cells. Small scale preparation DNA was prepared from the transformants and screened for the presence of the multi-cloning site. Plasmid pMC200, which contains the multi-cloning site, was isolated. The DNA sequence of the multi-cloning site was confirmed.

D. Construction of pJO200

Figure 10:
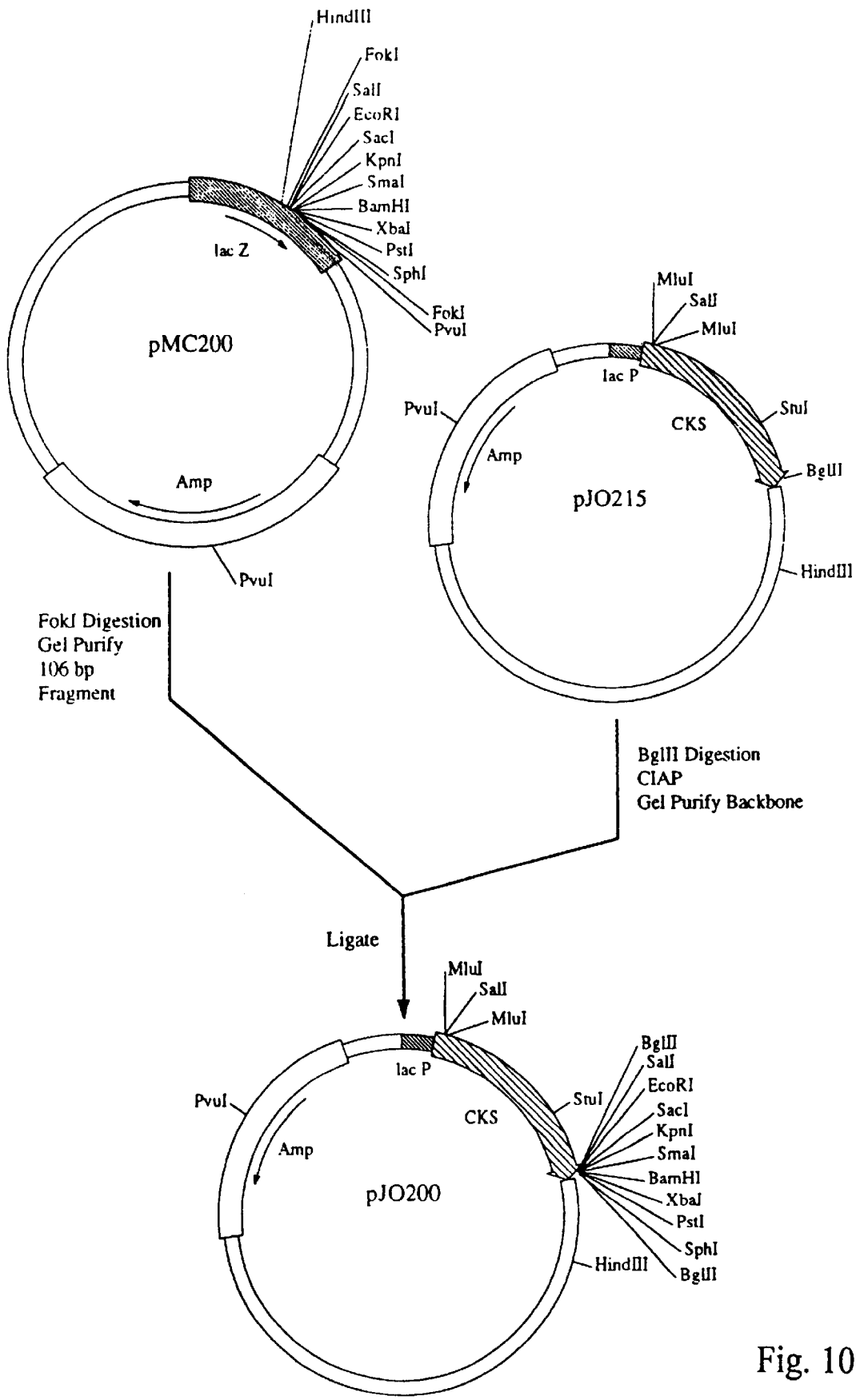
FIG. 10 is a schematic representation of the construction of plasmid pJO200.

The plasmid pJO200 is a derivative of plasmid pJO215 (FIG. 10). This plasmid was constructed by removing the multi-cloning site from pMC200 and cloning this site at the 3' end of the CKS gene in pJO215. Large scale plasmid DNA (pMC200 and pJO215) was isolated from TB1 cells as described in general methods. Plasmid pJO215 was digested to completion with BglII and then treated with calf intestinal alkaline phosphatase (CIAP) to prevent recircularization of the plasmid during the ligation reaction. Plasmid pMC200 was digested with FokI and then the pJO215/BglII/CIAP DNA and the pMC200/FokI DNA containing the multi-cloning site (106 base pairs) were purified on a polyacrylamide gel. Digestion of plasmid pMC200 with FokI releases the multi-cloning site DNA from the plasmid. This DNA contains BglII sticky ends which will readily ligate into pJO215 DNA digested with BglII.

These purified DNA fragments were mixed and ligated at 16° C. with T4 DNA ligase overnight. The next day the ligation mixture was transformed into competent TB1 cells. Small scale preparation DNA was prepared from the transformants and screened for the presence of the multi-cloning site in the correct orientation at the BglII site. Plasmid pJO200, which contains the multi-cloning site in the correct orientation, was isolated. The DNA sequence of the multi-cloning site in pJO200 at the BglII site was confirmed.

Example 7

Construction of lacZ-pp38(106-373aa) Expression Vector pMB38

Figure 11:
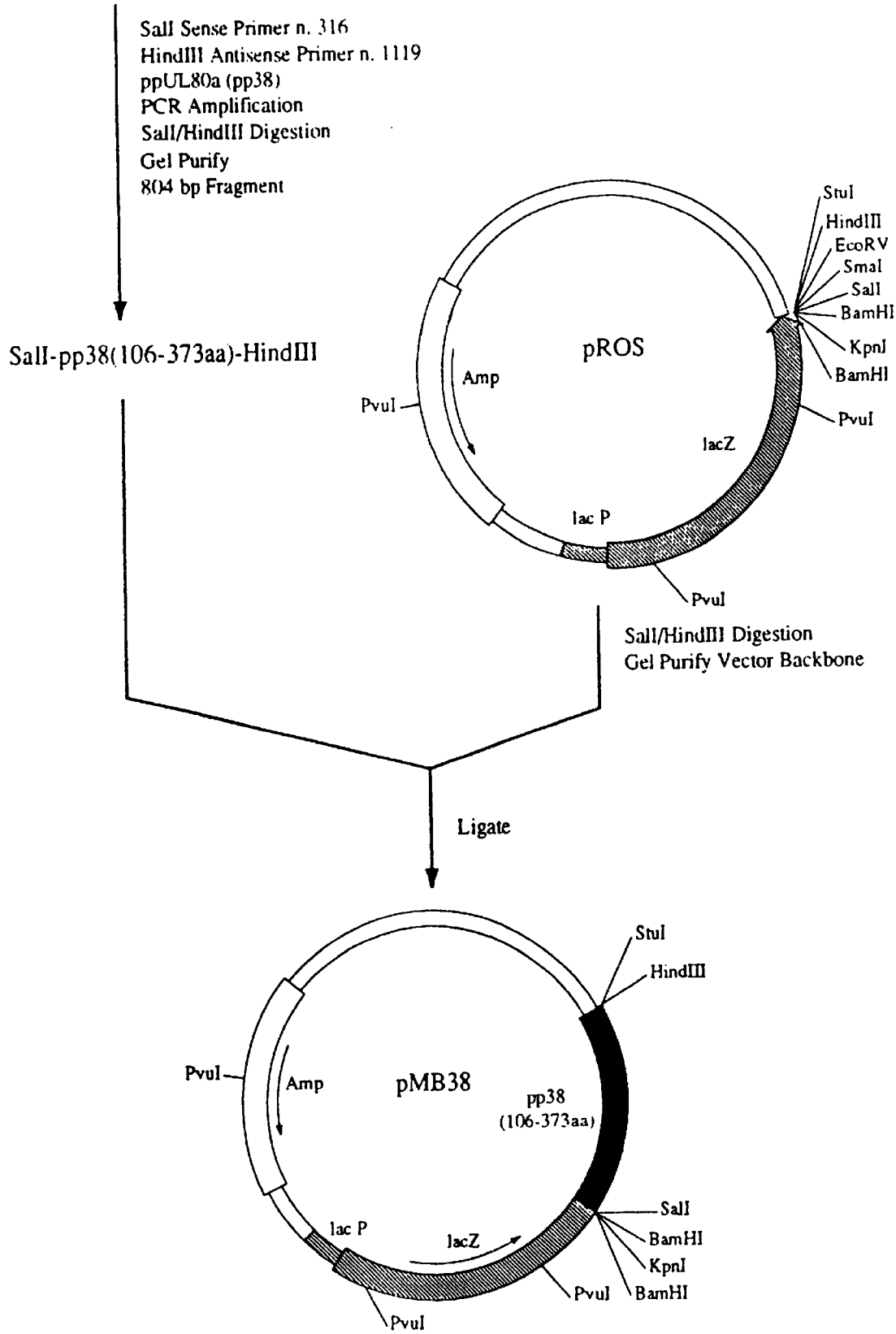
FIG. 11 is a schematic representation of the construction of plasmid pMB38: lacZpp38(106-373aa)

The plasmid pMB38 is a derivative of the lacZ expression vector pROS (FIG. 11). This plasmid was constructed by cloning a DNA fragment containing HCMV-pp38(106-373aa), obtained by PCR amplification of genomic HCMV DNA from the region of ppUL80a encoding amino acids 106-373aa of pp38 (nucleotides 316–1119), into the polylinker region pROS. The ppUL80a region encodes a phosphoprotein of 38 kD of HCMV. Plasmid pROS was digested with SalI and HindIII and the vector backbone was purified on an agarose gel. A sense primer starting at nucleotide 316 of ppUL80a containing a SalI site and an antisense primer starting at nucleotide 1119 of ppUL80a containing a HindIII site were synthesized and added to a PCR reaction mixture containing genomic HCMV DNA. After PCR amplification, the reaction mixture was digested with SalI and HindIII and the 804 base pair fragment containing pp38(106-373aa) was purified on an agarose gel. This purified fragment was then ligated to purified pROS/SalI/HindIII overnight at 16° C. The next day the ligation mixture was transformed into competent DH5α cells. Small scale preparation DNA was prepared from the transformants and screened for the presence of the 804 base pair pp38 (106-373aa) fragment in pROS at the end of the lacZ gene. Plasmid pMB38, which contains the pp38(106-373aa) fragment, was isolated. The DNA sequence of pp38 (106-373aa) in pMB38 was confirmed and the pp38(106-373aa) coding region was in-frame with the lacZ coding sequence.

Example 8

Construction of CKS-CMV Expression Vectors Based on pJO200

The CKS expression vector pJO200 is the building block for a series of five CKS-CMV gene fusion constructs. Two types of CKS-CMV gene fusion plasmids were constructed. One type of CKS-CMV gene fusion plasmid was constructed in which the CMV gene sequence is embedded within the CKS gene at nucleotide 638 of pJO200 (amino acid 171 of CKS) as shown below:

(5) CKS(1-171aa)-CMV-CKS(171-260aa)

This method of CKS-CMV gene fusion construction is called epitope-embedding. Fusion proteins expressed in E.coli from this type of construct contain the epitopes of the antigen embedded entirely within the CKS amino acid sequence. Plasmid pCMV-1A was constructed in this manner.

Another type of CKS-CMV gene fusion plasmid was constructed in which the CMV gene DNA sequence is linked to the 3' end of the CKS gene at amino acid 248 as shown below:

(6) CKS(1-248aa)-CMV

Plasmids pCMV-3B, pCMV-4, pCMV-9, and pCMV-26 were constructed in this manner. Large scale plasmid DNA (pJO200) was isolated using general methods for the constructs described below.

Figure 12:
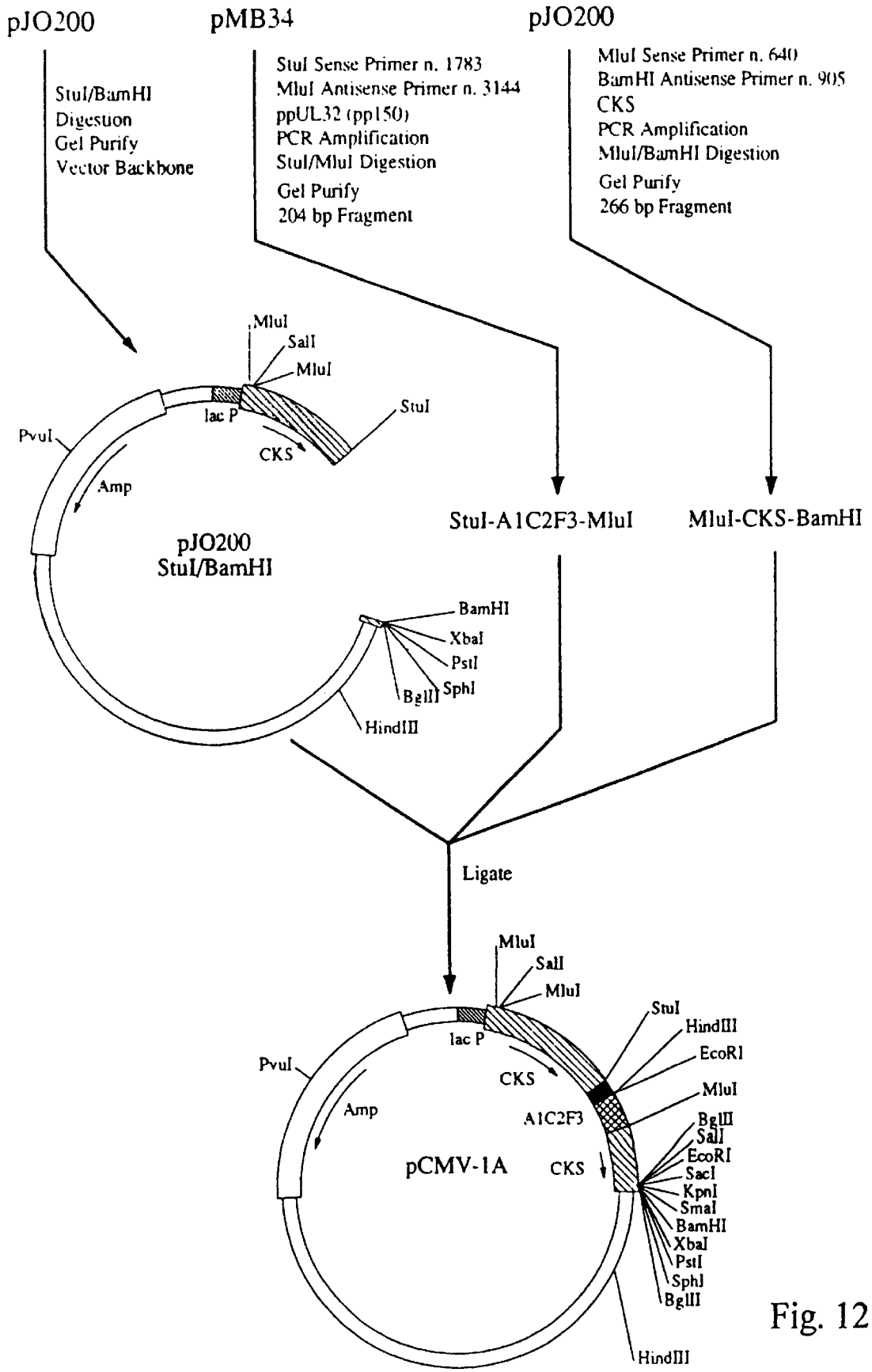
FIG. 12 is a schematic representation of the construction of plasmid pCMV-1A: CKS-A1C2F3-CKS.

A. Construction of pCMV-1A: CKS-A1C2F3-CKS—The plasmid pCMV-1A is a derivative of plasmid pJO200 (FIG. 12). This plasmid was constructed by cloning a DNA fragment containing HCMV-A1C2F3, obtained by PCR amplification of A1C2F3 DNA contained in plasmid pMB34, into the StuI site of pJO200. Large scale plasmid DNA (pMB34) was isolated by general methods. Plasmid pJO200 was digested with StuI and BamH-I and the vector backbone was purified on an agarose gel. This digest removes a portion of the 3' end of the CKS gene which will be restored in the ligation reaction. Into this vector backbone two PCR-derived DNA fragments will be cloned in a threeway ligation reaction. A1C2F3 will be cloned as a StuI/MluI DNA fragment and the remaining 3' portion of the CKS gene will be cloned as a MluI/BamH-I DNA fragment, restoring the complete CKS gene. A sense primer starting at nucleotide 1783 of ppUL32 containing a StuI site and an antisense primer starting at nucleotide 3144 of ppUL32 containing an MluI site were synthesized and added to a PCR reaction mixture containing plasmid pMB34. After PCR amplification, the reaction-mixture was digested with StuI and MluI, and the 204 base pair fragment containing A1C2F3 was purified on an agarose gel. A sense primer starting at nucleotide 640 of pJO200 containing an MluI site and an antisense primer starting at nucleotide 905 of pJO200 containing a BamH-I site were synthesized and added to a PCR reaction mixture containing plasmid pJO200. After PCR amplification, the reaction mixture was digested with MluI and BamH-I, and the 266 base pair fragment containing the 3' portion of the CKS gene was gel purified. These purified PCR-derived DNA fragments were then ligated to pJO200/StuI/BamH-I overnight at 16° C. The next day the ligation mixture was transformed into competent XL-1 Blue cells. Small scale preparation DNA was prepared from the transformants and screened for the presence of A1C2F3 inserted at the StuI site of pJO200. Plasmid pCMV-1A, which contains AIC2F3 inserted at the StuI site, was isolated. The DNA sequence of A1C2F3 and the 3' end of the CKS gene was confirmed. The coding region of the CKS-A1C2F3-CKS construct in pCMV-1A contains a bridge of 2 amino acids (threonine and arginine) contributed from the MluI site between A1C2F3 and the 3' end of CKS. In addition, amino acid 171 of CKS is duplicated in the construct as shown below:

(7) CKS(1-171aa)-A1C2-K-L-Q-E-F-F3-T-R-CKS(171-260aa)

Figure 13C:
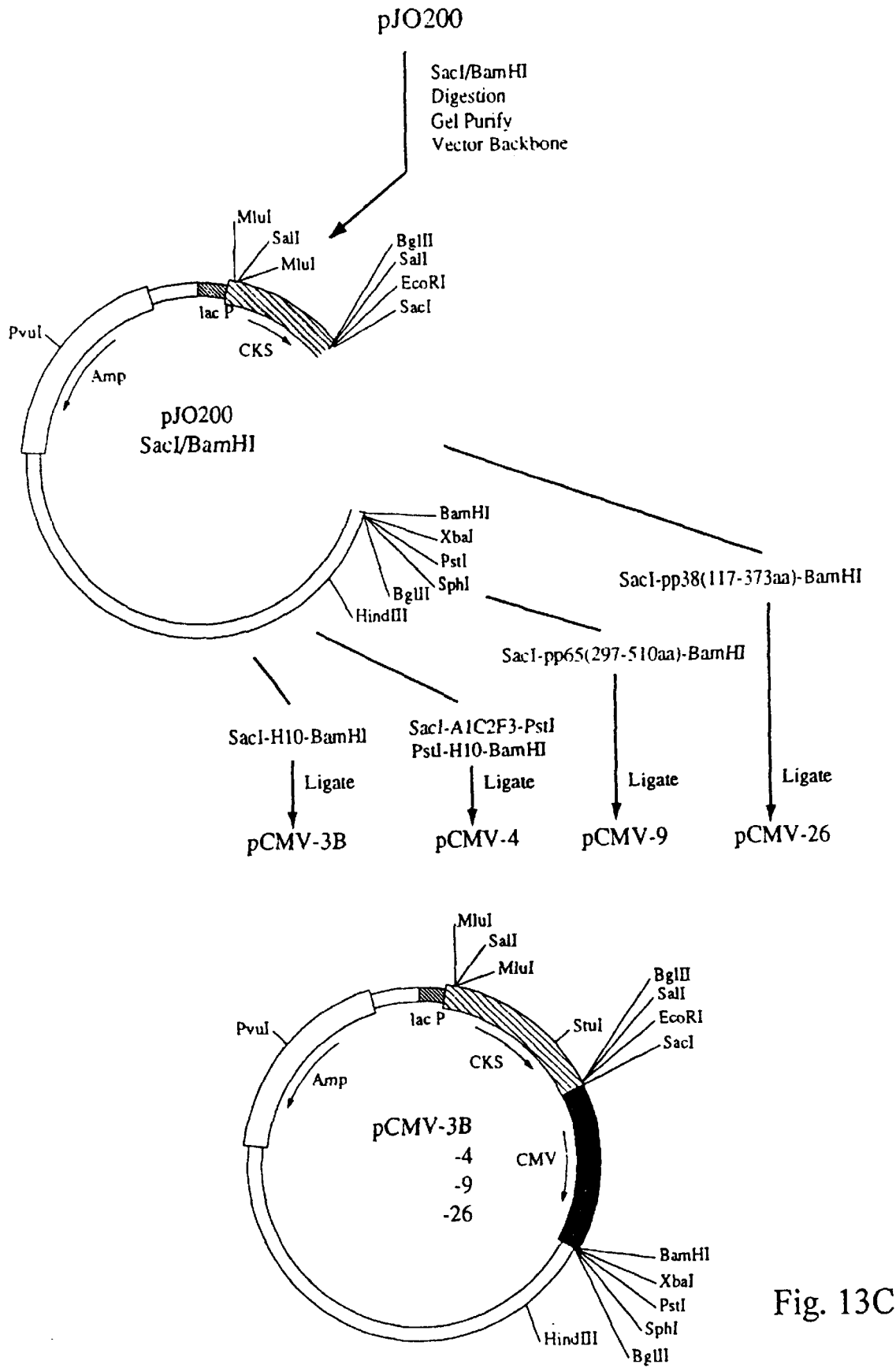
FIG. 13C is a schematic representation of the construction of: plasmid pCMV-3B:CKS-H10, plasmid pCMV-4:CKS-A1C2F3-H10, plasmid pCMV-9:CKS-pp65(297-510aa), and plasmid pCMV-26:CKS-pp38(117-373aa)

B. Construction of pCMV-3B: CKS-H10—The plasmid pCMV-3B is a derivative of plasmid pJO200 (FIGS. 13A and 13C). This plasmid was constructed by cloning a DNA fragment containing HCMV-H10 from plasmid pROSH10, described in Example 1 [see also: Ripalti et al. J. Virological Methods 46: 39, 1994], into pJO200. The H10 DNA sequence is derived from ppUL44 which encodes the phosphoprotein of 52 kD of HCMV. The H10 portion of ppUL44 in pROSH10 contains nucleotides 604–1299 (amino acids 202–434). H10 encodes the C-terminal half of phosphoprotein pp52. Plasmid pCMV-3B was constructed by cloning the H10 DNA fragment from pROSH10, obtained by PCR amplification of the H10 DNA sequence, into the SacI/BamH-I sites of pJO200. Plasmid pJO200 was digested with SacI and BamH-I and the vector backbone was purified on an agarose gel. A sense primer starting at nucleotide 604 of ppUL44 containing a SacI site and an antisense primer starting at nucleotide 1299 of ppUL44 containing a stop codon at the end of the H10 coding sequence and a BamH-I site were synthesized and added to a PCR reaction mixture containing plasmid pROSH10. After PCR amplification, the reaction mixture was digested with SacI and BamH-I, and the 696 base pair fragment containing H10 was purified on an agarose gel and then ligated to pJO200/SacI/BamH-I overnight at 16° C. The next day the ligation mixture was transformed into competent XL-1 Blue cells. Small scale preparation DNA was prepared from the transformants and screened for the presence of the 696 base pair fragment in pJO200 at the SacI/BamH-I sites. Plasmid pCMV-3B, which contains the H10 fragment fused in-frame with the CKS gene, was isolated. The DNA sequence of H10 and the 3' end of the CKS gene was confirmed. This CKS-CMV fusion construct is diagrammed below:

(8) CKS(1-248aa)-H10

C. Construction of pCMV-4: CKS-A1C2F3-H10—The plasmid pCMV-4 is a derivative of pJO200 (FIGS. 13A and 13C). This plasmid was constructed by cloning PCR amplified DNA fragments, containing HCMV-A1C2-K-L-Q-E-F-F3 (briefly: A1C2F3) and HCMV-H10, derived from pMB34 and pROSH10, respectively, into pJO200. Plasmid pJO200 was digested with SacI and BamH-I and the vector backbone was purified on an agarose gel. Into this vector backbone the two PCR-derived DNA fragments will be cloned in a three-way ligation reaction. A1C2-bridge-F3 will be cloned as a SacI/PstI DNA fragment and H10 will be cloned as a PstI/BamH-I DNA fragment. A sense primer starting at nucleotide 1783 of ppUL32 containing a SacI site and an antisense primer starting at nucleotide 3144 of ppUL32 containing an PstI site were synthesized and added to a PCR reaction mixture containing plasmid pMB34. After PCR amplification, the reaction mixture was digested with SacI and PstI, and the 204 base pair fragment containing A1C2F3 was purified on an agarose gel. A sense primer starting at nucleotide 604 of ppUL44 containing a PstI site and an antisense primer starting at nucleotide 1299 of ppUL44 containing a stop codon at the end of the H10 coding sequence and a BamH-I site were synthesized and added to a PCR reaction mixture containing plasmid pROSH10. After PCR amplification, the reaction mixture was digested with PstI and BamH-I, and the 696 base pair fragment containing H10 was purified on an agarose gel. These purified PCR-derived DNA fragments were then ligated to pJO200/SacI/BamH-I overnight at 16° C. The next day the ligation mixture was transformed into competent XL-1 Blue cells. Small scale preparation DNA was prepared from the transformants and screened for the presence of A1C2F3 and H10 inserted at the SacI/BamH-I sites of pJO200. Plasmid pCMV-4, which contains A1C2F3 and H10 at the end of the CKS gene in pJO200, was isolated. The DNA sequence of A1C2-K-L-Q-E-F-F3 and H10 was confirmed. The coding region of the CKS-A1C2F3-H10 construct in pCMV-4 contains a bridge of 2 amino acids contributed from the PstI site between A1C2F3 and H10. This CKS-CMV fusion construct is diagrammed below:

(9) CKS(1–248aa)-A1C2-K-L-Q-E-F-F3-L-Q-H10

D. Construction of pCMV-9: CKS-pp65(297-510aa)—The plasmid pCMV-9 is a derivative of pJO200 (FIGS. 13B and 13C). This plasmid was constructed by cloning a DNA fragment containing HCMV-pp65(297-510aa), obtained by PCR amplification of HCMV cDNA from the region of ppUL83 encoding amino acids 297–510 of pp65 (nucleotides 889–1530), into pJO200. Plasmid pJO200 was digested with SacI and BamH-I and the vector backbone was purified on an agarose gel. A two-stage nested PCR reaction was used to generate the HCMV-pp65(297-510aa) DNA fragment using HCMV cDNA as template, as follows. For the outer nest PCR amplification reaction, a sense primer starting at nucleotide 807 of ppUL83 and an antisense primer starting at nucleotide 1572 of ppUL83 were synthesized and added to a PCR reaction mixture containing HCMV cDNA. After PCR amplification, the outer nest PCR reaction mixture was used as template DNA for the inner nest PCR amplification reaction. For the inner nest PCR amplification reaction, a sense primer starting at nucleotide 889 of ppUL83 containing a SacI site and an antisense primer starting at nucleotide 1530 of ppUL83 containing a stop codon at the end of the pp65(297-510aa) coding sequence and a BamH-I site, were synthesized and added to a PCR reaction mixture containing outer nest amplified DNA. After PCR amplification, the reaction mixture was digested with SacI and BamH-I, and the 642 base pair fragment containing pp65(297-510aa) was purified on an agarose gel. This purified DNA fragment was then ligated to pJO200/SacI/BamH-I overnight at 16° C. The next day the ligation mixture was transformed into competent XL-1 Blue cells. Small scale preparation DNA was prepared from the transformants and screened for the presence of pp65(297-510aa) inserted at the SacI/BamH-I sites of pJO200. Plasmid pCMV-9, which contains pp65(297-510aa) at the end of the CKS gene in pJO200, was isolated. The DNA sequence of pp65(297-510aa) was confirmed. This CKS-CMV fusion construct is diagrammed below:

(10) CKS(1-248aa)-pp65(297-510aa)

E. Construction of pCMV-26: CKS-pp38(117-373aa)—The plasmid pCMV-26 is a derivative of pJO200 (FIGS. 13B and 13C). This plasmid was constructed by cloning a DNA fragment containing HCMVpp38(117-373aa), obtained by PCR amplification of pp38 DNA from the region of ppUL80a encoding amino acids 117–373 of pp38 (nucleotides 349–1119) derived from pMB38, into pJO200. Large scale plasmid DNA (pMB34) was isolated as described in general methods. Plasmid pJO200 was digested with SacI and BamH-I and the vector backbone was purified on an agarose gel. A sense primer starting at nucieotide 349 of ppUL80a containing a SacI site and an antisense primer starting at nucleotide 1119 of ppUL80a containing a BamH-I site were synthesized and added to a PCR reaction mixture containing pMB38 DNA. After PCR amplification, the reaction mixture was digested with SacI and BamH-I, and the 771 base pair fragment containing pp38(117-373aa) was purified on an agarose gel. This purified DNA fragment was then ligated to pJO200/SacI/BamH-I overnight at 16° C. The next day the ligation mixture was transformed into the competent XL-1 Blue cells. Small scale preparation DNA was prepared from the transformants and screened for the presence of pp38(117-373aa) inserted at the SacI/BamH-I sites of pJO200. Plasmid pCMV-26, which contains pp38 (117-373aa) at the end of the CKS gene in pJO200, was isolated. The DNA sequence of pp38(117-373aa) was confirmed. This CKS-CMV fusion construct is diagrammed below:

(11) CKS(1-248aa)-pp38(117-373aa)

Example 9

Construction of CKS Epitope-Embedding Expression Vector pEE1

The CKS epitope-embedding expression vector pEE1 allows the embedding of recombinant proteins containing epitopes within the CKS protein as diagrammed below:

(12) CKS(1-171aa)-Recombinant Protein-T-R-CKS(171-260aa)

This pEE1 vector was constructed in two steps starting with the CKS expression vector pJO200. In the first step a mutagenic oligonucleotide is cloned into a pair of adjacent MluI sites located near the 5' end of the CKS gene in pJO200, removing both MluI sites and a SalI site. This modification to pJO200 allows the use of a unique MluI cloning site to be introduced further downstream in the CKS gene in the next step. In the second step a fragment of DNA from pCMV-1A is cloned into this modified pJO200 vector, thus permitting the embedding of genes as StuI/MluI fragments into the CKS gene.

Figure 14A:
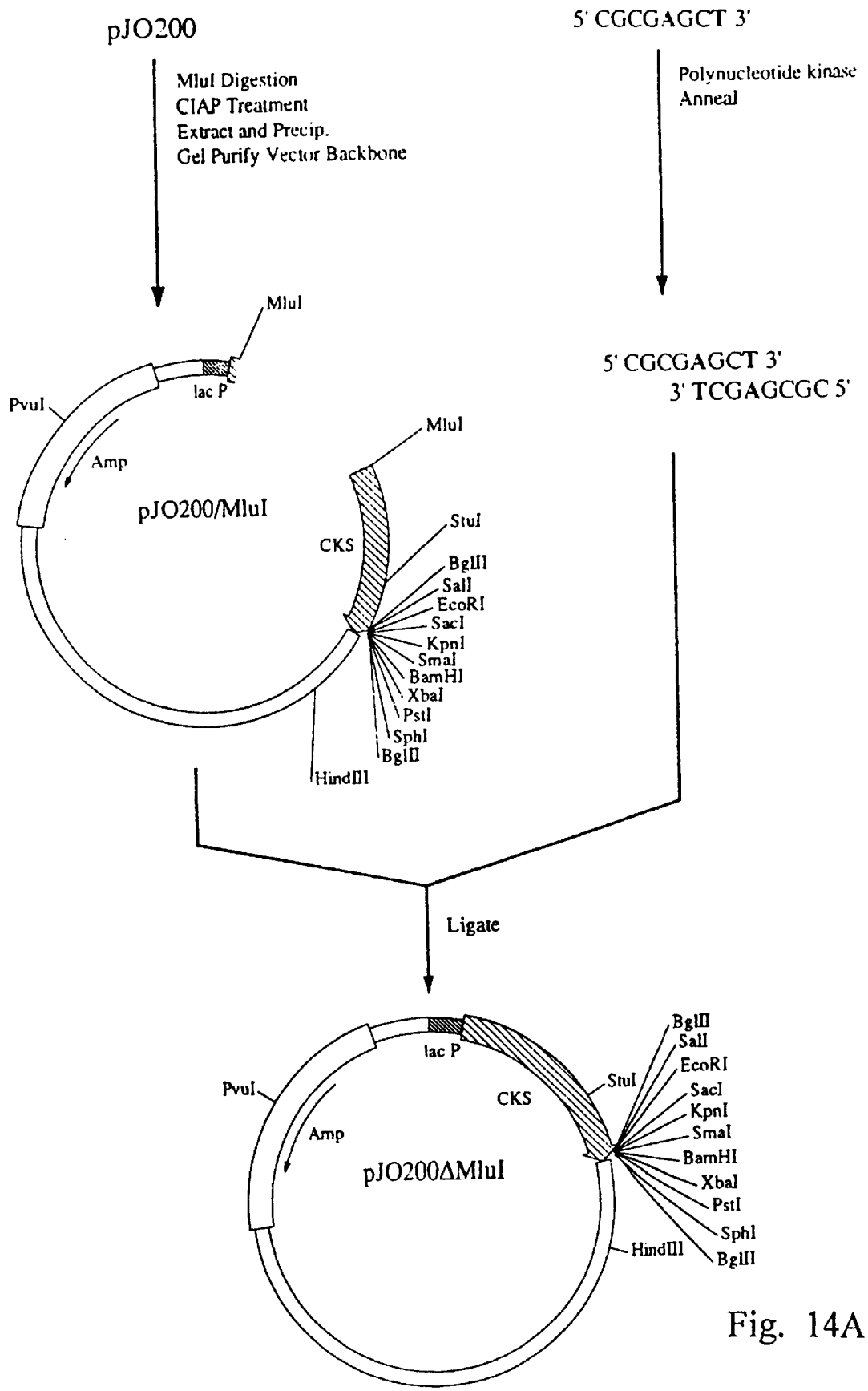
FIG. 14A is a schematic representation of the construction of plasmid pJO200-ΔMIuI.

A. Construction of pJO200-ΔMluI—The plasmid pJO200-ΔMluI is a derivative of the CKS expression vector pJO200 (FIG. 14A). This plasmid was constructed by removing a pair of adjacent MluI sites and a SalI site located at nucleotides 161–174 (11–15 amino acids) in the pJO200 DNA sequence shown below using a mutagenic oligonucleotide:

```
              MluI  SalI  MluI
               ▽    ▽    ▽
(13) ¹⁵¹CCC GCG CGC TAC GCG TCG ACG CGT CTG CCC¹⁸⁰   (SEQ ID NO:12)
         pro Ala Arg Tyr Ala Ser Thr Arg Leu Pro    (SEQ ID NO:14)
Native pJO200 DNA sequence nucleotides 151–180 taken in direction 5'→3'
```

Plasmid pJO200 was digested with MluI and then ethanol precipitated and resuspended in alkaline phosphatase buffer.

(15) 5' CGCGAGCT 3' (SEQ ID NO:15)
     3' TCGAGCGC 5'

This oligonucleotide contains MluI sticky-ends permitting ligation into MluI digested pJO200 DNA. The sequence of this oligonucleotide differs from the native pJO200 DNA sequence in that the "T" and "A" residues underlined in the pJO200 sequence (13) above have been reversed in the mutagenic oligonucleotide as underlined. Thus, the mutagenic oligonucleotide when cloned into the MluI site of pJO200 will destroy both MluI sites and the SalI site. After oligonucleotide synthesis, the synthetic oligonucleotide was phosphorylated at its 5' end using polynucleotide kinase. After treatment with this enzyme, the phosphorylated oligonucleotide was heated to 65° C. for 20 minutes to inactivate the kinase. After cooling to room temperature, the phosphorylated oligonucleotide was mixed with the pJO200/MluI/CIAP, heated at 65° C. for 5 minutes and then cooled to room temperature gradually to permit annealing of the phosphorylated oligonucleotide to itself. Ligation buffer and T4 DNA ligase were then added to the mixture and incubated overnight at range of temperatures from 20° C. to 4° C. The next day the ligation mixture was transformed into competent XL-1 Blue cells. Small scale preparation DNA was prepared from the transformants and screened for the loss of the MluI and SalI sites. Plasmid pJO200ΔMluI, which has lost these restriction enzyme sites, was isolated. The DNA sequence of the 5' end of the CKS gene was confirmed. In addition to removing the MluI and SalI sites, the mutagenic oligonucleotide changes the amino acids coded by nucleotides 166–171 from Ser-Thr to Thr-Ser as shown below:

```
(13') ¹⁵¹CCC GCG CGC TAC GCG ACG TCG CGT CTG CCC¹⁸⁰   (SEQ ID NO:13)
           pro Ala Arg Tyr Ala Thr Ser Arg Leu Pro    (SEQ ID NO:15)
     pJO200ΔMluI DNA sequence nucleotides 151–180 taken in direction 5→3'
```

Plasmid pJO200/MluI was then treated with calf intestinal alkaline phosphatase (CIAP) to remove the 5' phosphate groups to prevent self-ligation. After treatment with CIAP the DNA was extracted with phenol-chloroform, ethanol precipitated, resuspended in TE buffer, and then the vector backbone was purified on an agarose gel. The following mutagenic oligonucleotide was synthesized in preparation for ligation to pJO200/MluI/CIAP:

(14) 5' C.GCGACGT 3'

Figure 15:
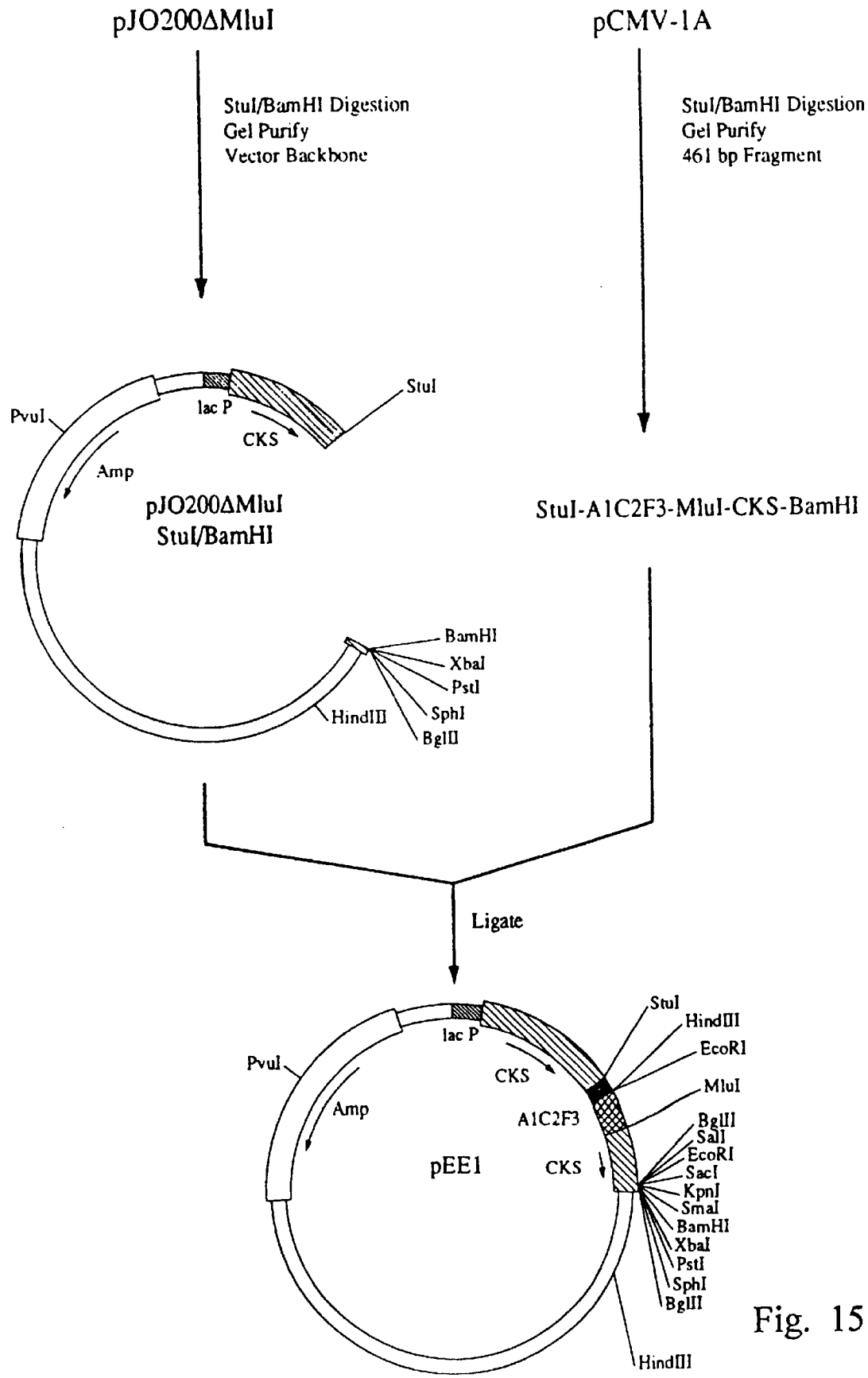
FIG. 15 is the schematic representation of the construction of plasmid pEE1.

This oligonucleotide is self-complementary at its 3' end and will form the following double-stranded structure after a heat denaturation step followed by an annealing step:

B. Construction of pEE1—The plasmid pEE1 is a derivative of the plasmid pJO200ΔMluI (FIG. 15). This plasmid was constructed by cloning a StuI/BamH-I fragment from pCMV-1 A, which contains HCMV-A1C2F3 embedded within the CKS gene, into the StuI/BamH-I sites of pJO200ΔMluI. By substituting the StuI/BamH-I DNA fragment within the CKS coding region present in pJO200ΔMluI with the StuI/BamH-I fragment from pCMV-1A, the resulting plasmid pEE1 contains HCMV-A1C2F3 embedded within the CKS gene. Plasmid pEE1 differs from plasmid pCMV-1A in that pEE1 does not contain the upstream MluI sites present in the 5' end of the CKS gene. Hence, digestion of pEE1 with StuI and MluI will release the HCMV-A1C2F3 DNA fragment and provide a vector backbone, after purification on an agarose gel, capable of accepting other genes for embedding into the CKS gene as blunt/MluI compatible sticky-end DNA fragments. Large scale plasmid DNAs (pJO200ΔMluI and pCMV-1A) were isolated as described in general methods. Plasmid pCMV-1A was digested with StuI and BamH-I and the 461 base pair fragment, containing A1C2F3 and the 3' end of the CKS gene, was purified on an agarose gel. Plasmid pJO200ΔMluI was digested with StuI and BamH-I and the vector backbone was purified on an agarose gel. These purified DNA fragments were then mixed together and ligated overnight at 16° C. The next day the ligation mixture was transformed into competent XL-1 Blue cells. Small scale preparation DNA was prepared from the transformants and screened for the presence of the 461 base pair A1C2F3 DNA fragment in pJO200ΔMluI. Plasmid pEE1, which contains the A1C2F3 DNA fragment and no MluI sites in the 5' end of the CKS gene, was isolated. The DNA sequence of the 3' end of the CKS gene and the A1C2F3 fragment was confirmed. Digestion of plasmid pEE1 with StuI and BamH-I followed by purification of the vector backbone on an agarose gel removes the A1C2F3 DNA fragment completely in preparation for ligation with other DNA fragments. This purified vector backbone can accept DNA fragments for embedding into the CKS gene in the correct reading frame in the following format:

(16) 5' X-Gene of interest-Y 3' where X is a blunt end and Y is an MluI compatible sticky-end, for example MluI or BssHII.

Example 10

Construction of CKS-epitope-embedding Expression Vectors Based on pEE1

The CKS expression vector pEE1 is the building block for a series of three CKS-CMV-CKS gene fusion constructs. For each construct plasmid pEE1 was digested with StuI and MluI and the vector backbone was purified. This backbone is ready to accept CMV gene fragments generated by PCR which have a StuI site at their 5' end and a MluI site at their 3' end. After digestion with StuI and MluI, the PCR fragments are cloned in-frame into the pEE1/StuI/MluI backbone. The CKS-CMV-CKS fusion proteins expressed from these vectors are diagrammed below where T and R are the threonine and arginine residues, respectively, encoded by the synthetic MluI site introduced into the vector:

(17) CKS(1-171aa)-CMV-T-R-CKS(171-260)

A. Construction of pCMV-27: CKS-A1C2F3-H10-CKS—The plasmid pCMV-27 is a derivative of pEE1 (FIGS. 16A and 16B). This plasmid was constructed by cloning a PCR amplified DNA fragment, containing HCMV-A1C2F3-H10 derived from pCMV-4 (therefore containing the bridge KLQEF between A1C2 and F3), into pEE1. Large scale plasmid DNA (pEE1 and pCMV-4) was isolated operating as described in general methods. Plasmid pEE1 was digested with StuI and MluI and the vector backbone was purified on an agarose gel. A sense primer starting at nucleotide 1783 of ppUL32 containing a StuI site and an antisense primer starting at nucleotide 1299 of ppUL44 containing an MluI site were synthesized and added to a PCR reaction mixture containing plasmid pCMV-4. After PCR amplification, the reaction mixture was digested with StuI and MluI, and the 906 base pair fragment containing A1C2F3-H10 was purified on an agarose gel. This purified DNA fragment was ligated to pEE1/StuI/MluI overnight at 16° C. The next day the ligation mixture was transformed into competent XL-1 Blue cells. Small scale preparation DNA was prepared from the transformants and screened for the presence of the A1C2F3-H10 DNA fragment inserted at the StuI/MluI sites of pEE1. Plasmid pCMV-27, which contains A1C2F3-H10 embedded at the StuI/MluI sites of pEE1, was isolated. The DNA sequence of A1C2F3-H10 and the adjacent DNA sequence of CKS was confirmed. This CKS-CMV-CKS fusion construct is diagrammed below, where L, Q and T, R are the leucine, glutamine and threonine, arginine residues, respectively, encoded by the synthetic PstI and MluI sites introduced into the vector:

(18) CKS(1-171aa)-A1C2-K-L-Q-E-F-F3-L-Q-H10-T-R-CKS(171-260aa)

B. Construction of pCMV-28: CKS-pp65(297-510aa)-CKS—The plasmid pCMV-28 is a derivative of pEE1 (FIGS. 16A and 16B). This plasmid was constructed by cloning a PCR amplified DNA fragment, containing HCMV-pp65(297-510aa) derived from pCMV-9, into pEE1. Large scale plasmid DNAs (pEE1 and pCMV-9) were isolated by general methods. Plasmid pEE1 was digested with StuI and MluI and the vector backbone was purified on an agarose gel. A sense primer starting at nucleotide 889 of ppUL83 containing a StuI site and an antisense primer starting at nucleotide 1530 of ppUL83 containing an MluI site were synthesized and added to a PCR reaction mixture containing plasmid pCMV-9. After PCR amplification, the reaction mixture was digested with StuI and MluI, and the 642 base pair fragment containing pp65(297-510aa) was purified on an agarose gel. This purified DNA fragment was ligated to pEE1/StuI/MluI overnight at 16° C. The next day the ligation mixture was transformed into competent XL-1 Blue cells. Small scale preparation DNA was prepared from the transformants and screened for the presence of the pp65 (297-510aa) DNA fragment inserted at the StuI/MluI sites of pEE1. Plasmid pCMV28, which contains pp65(297-510aa) embedded at the StuI/MluI sites of pEE1, was isolated. The DNA sequence of pp65(297-510aa) and the adjacent DNA sequence of CKS was confirmed. This CKS-CMV-CKS fusion construct is diagrammed below where T and R are the threonine and arginine residues, respectively, encoded by the synthetic MluI sites introduced into the vector:

(19) CKS(1-171aa)-pp65(297-510aa)-T-R-CKS(171-260aa)

C. Construction of pCMV-29: CKS-DD38(117-373aa)-CKS—The plasmid pCMV-29 is a derivative of pEE1 (FIGS. 16A and 16B). This plasmid was constructed by cloning a PCR amplified DNA fragment, containing HCMV-pp38(117-373aa) derived from pCMV-26, into pEE1. Large scale plasmid DNA (pEEI and pCMV-26) was isolated as described in general methods. Plasmid pEE1 was digested with StuI and MluI and the vector backbone was purified on an agarose gel. A sense primer starting at nucleotide 349 of ppUL80a containing a StuI site and an antisense primer starting at nucleotide 1119 of ppUL80a containing an MluI site were synthesized and added to a PCR reaction mixture containing plasmid pCMV-26. After PCR amplification, the reaction mixture was digested with StuI and MluI, and the 771 base pair fragment containing pp38(117-373aa) was purified on an agarose gel. This purified DNA fragment was ligated to pEE1/StuI/MluI overnight at 16° C. The next day the ligation mixture was transformed into competent XL-1 Blue cells. Small scale preparation DNA was prepared from the transformants and screened for the presence of the pp38(117-373aa) DNA fragment inserted at the StuI/MluI sites of pEEI. Plasmid pCMV-29, which contains pp38(117-373aa) embedded at the StuI/MluI sites of pEE1, was isolated. The DNA sequence of pp38(117-373aa) and the adjacent DNA sequence of CKS was confirmed. This CKSCMV-CKS fusion construct is diagrammed below where T and R are the threonine and arginine residues, respectively, encoded by the synthetic MluI sites introduced into the vector:

(20) CKS(1-171aa)-pp38(117-373aa)-T-R-CKS(171-260aa)

Example 11

A. Expression of HCMV Genes.

Bacterial clones expressing HCMV fusion proteins of Example 10, the control bacterial strain expressing unfused CKS, and bacterial clones expressing HCMV fusion proteins of Example 8, were grown in "SUPERBROTH II" media containing 100 µg/ml ampicillin to log phase and the synthesis of the CKS-HCMV fusion proteins was induced by the addition of IPTG as previously described [22]. After 4 hours post-induction, the cells were harvested and the cell pellets were stored at −80° C. until protein purification. The relevant data of all the expressed proteins are given in Table 3.

Purification of Unfused CKS and Recombinant CKS-HCMV Fusion Proteins.

Insoluble CKS-HCMV fusion proteins (rpCMV-1A, rpCMV-3B, rpCMV-4, rpCMV-9, rpCMV-27, rpCMV-28, rpCMV-29) were purified after lysis by a combination of detergent washes that were followed by solubilization in 8M urea [22]. After solubilization in 8M urea, the fusion proteins were purified by Q-Sepharose chromatography (Pharmacia Biotech, Piscataway, N.J.). Fusion protein 4 (rpCMV-4) and 9 (rpCMV-9) were subjected to additional purification by Sephacryl S-200 chromatography (Pharmacia Biotech, Piscataway, N.J.). Soluble CKS-HCMV fusion protein 26 (rpCMV-26) was purified after cell lysis on preparative SDS-PAG using a BIO-Rad Prep Cell (Bio-Rad, Richmond, Calif.). Soluble CKS protein was purified after cell lysis by ammonium sulfate precipitation followed by DEAE chromatography.

Example 12

Automated HCMV IgM Immunoassay

The use of recombinant polypeptides, which contain epitopes within the ppUL32, ppUL44, ppUL83, and ppUL80a regions of the HCMV genome, provide immunological assays that have increased sensitivity and that may be more specific than HCMV IgM immunoassays using epitopes from the virus.

In the automated HCMV IgM immunoassay, three E.Coli expressed recombinant proteins, CKS-A1C2F3-H10-CKS (rpCMV-27), CKS-pp65-CKS (rpCMV-28), and CKS-pp38-CKS (rpCMV-29), representing four distinct regions of the HCMV genome were used. Each of these recombinant polypeptides were prepared according to Example 10 (A,B and C) and 11. In the automated immunoassay, each of these three recombinant antigens were coated separately onto polystyrene microparticles, one antigen per microparticle. The automated immunoassay can then be run in either a sequential mode of operation or in a combination mode of operation. In a modification of the automated immunoassay, all of these three recombinant antigens may be coated together onto the same polystyrene microparticle, three antigens per microparticle. The modified automated immunoassay can then be run in a combination mode of operation.

The polystyrene microparticles (2.65 µm size) in distilled water were introduced into a solution containing 50 mM Tris, 137 mM sodium chloride, 0.1% sodium azide, pH 7.5.

The polystyrene microparticles were then dispensed into three separate bottles designated rpCMV-27, rpCMV-28, and rpCMV-29. Recombinant rpCMV-27 in 50 mM Tris, pH 8.5 was added to the bottle containing rpCMV-27 to give a final concentration of 25–100 µg/ml. Recombinant rpCMV-28 in 50 mM Tris, pH 8.5 was added to the bottle containing rpCMV-28 to give a final concentration of 25–100 µg/ml. Recombinant rpCMV-29 in 50 mM Tris, pH 8.5 was added to the bottle containing rpCMV-29 to give a final concentration of 25–100 µg/ml. The final concentration of the polystyrene microparticles in each bottle was 1–3% solids. The bottles were rotated end over end (30–50 rpm) for two hours at room temperature (19–22° C.) and were then centrifuged at 10,000–15,000×g for 10 minutes at room temperature. The microparticles, which were in the form of pellets, were then resuspended in a mixture containing 90 mM Tris, 135 mM sodium chloride, 100 mM disodium EDTA, 6% sucrose, 0.18% "TWEEN-20", 50% fetal calf serum (CMV antibody free), 35 µg/ml CKS protein, pH 7.5 to give a final concentration of 0.1–0.25% solids. The microparticles were then loaded into plastic bottles.

The polystyrene microparticles coated with rpCMV-27 rpCMV-28, and rpCMV-29 were used in an antibody capture format in an automated immunoassay performed on the ABBOTT "IMx"® instrument (Abbott Laboratories, Abbott Park, Ill.). The aforementioned coated microparticles can also be used in an antibody capture format in an automated immunoassay performed on the Abbott "AxSYM"® instrument (Abbott Laboratories, Abbott Park, Ill.).

These systems employ pipetting devices that dispense serum samples and reagents automatically. These instruments employ an optical reader that can measure the fluorescence emission reflectance at 448 nm from the sample matrix. In the sequential mode of operation, the serum sample is incubated separately with each of the three coated microparticles. In the combination mode of operation, an equal volume of each of the three coated microparticles are mixed together prior to incubation with the serum sample. In either mode the appropriate stock microparticles are dispensed into plastic bottles and then are loaded onto the instrument.

The preferred conjugate is goat anti-human IgM alkaline phosphatase conjugate. The conjugate is titered to determine a working concentration of 1–5 µg/ml. The conjugate diluent includes 90 mM Tris, 135 mM sodium chloride, 5% fetal calf serum, 0.1% sodium azide, pH 7.4. The conjugate is sterile filtered, filled in plastic bottles, and loaded onto the instrument. The preferred substrate for the conjugate is 4-methylumbelliferyl phosphate.

Anti-HCMV positive index calibrator is prepared from plasma units positive for antibodies to HCMV. The pool of units includes plasma with antibodies reactive to rpCMV-27, rpCMV-28, and rpCMV-29. The pooled units are recalcified, aliquoted, and stored at −20° C. or at 2–8° C. For each lot of positive Index calibrator, the stock solution is diluted with negative control containing 0.1% sodium azide as a preservative. The final material is sterile filtered and filled in plastic bottles.

Anti-HCMV negative control is prepared from recalcified human plasma negative for antibodies to rpCMV-27, rpCMV-28. and rpCMV-29 proteins of HCMV. The plasma is also negative for antibodies to human immunodeficiency virus (HIV) and negative for hepatitis B surface antigen (HBsAg). The units are pooled, and 0.1% sodium azide is added as a preservative. The final material is sterile filtered and filled in plastic bottles.

The serum samples to be tested are dispensed into the instrument's reaction vessels. The appropriate code to run the automated CMV IgM immunoassay is entered and then the assay is begun. The instrument dilutes the serum sample in line diluent (0.1 M sodium phosphate, 0.1% sodium azide, pH 7-5 or 0.3 M sodium chloride, 0.1 M Tris, 0.1% sodium azide, pH 7.5) and then adds the microparticles to the diluted serum sample. After incubation for 5–10 minutes, the mixture is then transferred to the reaction vessel matrix. The matrix is washed with line diluent and then the conjugate is added to the reaction vessel matrix. After incubation for 8–10 minutes, the matrix is washed with line diluent and then the substrate for the conjugate is added. The fluorescence emission reflectance at 448 nm from the sample matrix is read immediately and the instrument reports both a rate count value and an index value for each sample. The index value is equal to the rate count value for the sample divided by the rate count value for the positive index calibrator.

In order to maintain acceptable assay specificity, the cut-off value for the assay should be at least 3–4 standard deviations above the mean of the index values for the negative samples. The cut-off value for the automated HCMV IgM immunoassay was set at an index value of 0.6. Any samples with an index value greater than or equal to 0.5 had to be treated with rheumatoid factor neutralization reagent and then rerun again on the instrument. Samples with an index value equal to or greater than 0.6 were considered positive for HCMV IgM antibody. Samples with an index value of 0.500–0.599 were considered equivocal, and samples with an index value less than 0.500 were considered negative for HCMV IgM antibody. The characteristics of the fusion proteins used in the assay are referred to in Table 3.

Automated HCMV IgM Immunoassay Performance

The performance of the automated HCMV IgM immunoassay was evaluated by testing seven HCMV IgM-negative serum samples and eleven HCMV IgM-positive serum samples. The titer of HCMV IgM antibody for these samples was initially determined using the HCMV IgM microtiter recombinant EIA described in Example 13. All HCMV IgM positive samples were confirmed to be positive by Western Blot using purified viral antigen (see Table 5). All HCMV IgM positive samples were treated with rheumatoid factor neutralization reagent prior to running them in the immunoassays described below in (a) and (b).

(a)—Sequential Mode of Operation

In the sequential mode of operation of the automated immunoassay, each serum/plasma sample is tested separately using the rpCMV-27 coated microparticles, rpCMV-28 coated microparticles, and rpCMV-29 coated microparticles.

A sample is considered positive for HCMV IgM antibody in the sequential mode of operation when the index value for the sample is equal to or greater than 0.6 with any one of rpCMV-27 coated microparticles or rpCMV-28 coated microparticles or rpCMV-29 coated microparticles.

A sample is considered equivocal for HCMV IgM antibody in the sequential mode of operation when the index value for the sample is 0.500–0.599 with rpCMV-27 coated microparticles or rpCMV-28 coated microparticles or rpCMV-29 coated microparticles.

A sample is considered negative for HCMV IgM antibody in the sequential mode of operation when the index value for the sample is less than 0.500 with rpCMV-27, rpCMV-28, and rpCMV-29 coated microparticles. As shown in Tables 4 and 5, all negative samples were determined to be negative for HCMV IgM antibody and all positive samples were determined to be positive for HCMV IgM antibody in the sequential mode of operation of the HCMV IgM automated immunoassay.

(b)—Combination Mode of Operation

In the combination mode of operation of the automated immunoassay, each serum/plasma sample is tested using an equal volume mixture of rpCMV-27, rpCMV-28, and rpCMV-29 coated microparticles (pooled microparticles). A sample is considered positive for HCMV IgM antibody in the combination mode of operation when the index value for the sample is equal to or greater than 0.6 with the pooled microparticles. A sample is considered equivocal for HCMV IgM antibody in the combination mode of operation when the index value for the sample is 0.500–0.599 with pooled microparticles. A sample is considered negative for HCMV IgM antibody in the combination mode of operation when the index value for the sample is less than 0.500 with pooled microparticles. As shown in Tables 4 and 5, all negative samples were determined to be negative for HCMV IgM antibody and all positive samples were determined to be positive for HCMV IgM antibody in the combination mode of operation of the HCMV IgM automated immunoassay.

Example 13

Manual HCMV IgG/IgM Immunoassay

1. HCMV Serology.

1.1—Conventional EIA (conv-EIA)—The evaluation of anti-HCMV IgG was carried out with a commercial kit ("ENZYGNOST" anti-HCMV/IgG EIA alpha method, Behring AG, Marburg, Germany). Plates were read on a microEIA automatic reader (Behring AG-Marburg, Germany). The evaluation of anti-HCMV IgM was performed using the "ENZYGNOST" Anti-HCMV/IgM kit (Behring AG, Germany). Both kits were used and the results interpreted as suggested by the manufacturers.

1.2—Western blotting (WB). Protein extracts from purified viral particles (Towne strain) were run in 9% acrylamide gel and electrophoretically separated polypeptides were then transferred to nitrocellulose paper. Infection of cells, virus purification, protein extraction, blotting and immune reaction with sera were done as previously described in detail [16].

1.3—Recombinant EIA (rec-EIA). EIA was performed following the procedure and using the reagents of the commercial kit Enrygnost anti-HCMV/IgG and IgM (Behring, Marburg, Germany). Briefly 0.05 $\mu$g of purified recombinant protein per well in bicarbonate buffer (pH 9.6) was used to coat EIA plastic plates (A/S NUNC, Roskilde, Denmark). After an overnight incubation at 4° C., plates were rinsed three times with PBS-"TWEEN 20" (0.05%) and incubated with BSA (1%) in bicarbonate buffer (pH 9.6). After a 1 hour incubation period at room temperature, wells were rinsed three times with PBS-"TWEEN 20" (0.05%) and incubated with human serum samples at a dilution of 1:100 and 1:40 in PBS for IgG and IgM respectively (50 $\mu$l final volume). The incubation was carried out at 37° C. for 2 hours. After three washes with PBS-"TWEEN 20", peroxidase-conjugated goat anti-human IgG or IgM antibodies were deposited into wells, and plates were incubated at 37° C. for 1.5 hours. After three washes with PBS-"TWEEN 20", immunoreactions were evidenced by addition of chromogen—TMB (Tetramethylene benzidine dihydrochloride). The reaction was stopped after one hour by the addition of sulfuric acid (0.5 N), and the results read on a "MICROEIA" automatic reader. For each sample, the immunoreaction level was considered to be the difference between the measured absorbances, (A rec.antigen- A control antigen), obtained. The cut-off value for each individual fusion protein was determined by testing 210 sera that did not contain IgM to HCMV (determined using both conv-EIA and WB). Cut off values for each fusion protein are reported in Table 3. For the determination of IgM antibodies, "The RF absorbent" (Behring, Marburg, Germany) was used to remove Rheumatoid factor from serum samples. To perform linear regression analysis and to standardize the test run, every plate included three serum calibrators. Reproducibility was controlled by including in each EIA plate six standard sera whose reactivity had previously been assayed in four independent experiments. Test runs were considered acceptable when the value of the internal control sera were within the interval of two standard deviations from the mean value previously established.

2. Human Serum Samples.

Many groups of human serum samples (sera) were used in this work. The first group of samples, which was used for the determination of the cut-off values, consisted of 210 sera from blood donors (150) and healthy adults (60). While sixty-eight sera were IgG/IgM–, 142 were IgG+/IgM– as judged by both conv-EIA and Western blotting. The second group of sera consisted of 150 HCMV-positive samples from immunocompetent subjects (50 with a high IgM titre to HCMV as detected by conv-EIA, 50 with a medium IgM level and 50 with a low level of HCMV-specific IgM). The presence of HCMV-specific IgM in this group of sera was determined by conv-EIA and confirmed by Western blotting. A third group of sera consisted of 51 sera from pregnant women (18 were from HCMV-uninfected women, 26 from HCMV infected women who did not transmit the infection and 7 from HCMV-infected pregnant women who transmitted the infection). All these sera were obtained between 22 and 24 weeks of gestation. A group of 35 sera from 35 newborns was also tested: 6 serum samples were obtained during the first week of life from 6 congenitally infected newborns, 19 sera were from newborns (1–8 months of life) in which the virus was repeatedly isolated from urine. Twelve newborns had different symptoms (maculopapular rash, encephalopathy, growth delay), the others were asymptomatic shedders. Finally ten sera were from HCMV-uninfected newborns during the first 8 months of life. Another group of samples consisted of 104 sera from 23 transplanted patients (20 heart and 3 kidney transplant recipients) who underwent a HCMV infection during the first 3 months alter transplantation. Eight patients had a primary infection, while 15 underwent a viral reactivation. The last group consisted of 200 serum samples randomly selected among sera from renal transplant recipients (150) and pregnant women (150), who came to diagnostic laboratory for HCMV monitoring after transplantation and during pregnancy.

3. Determination of a HCMV Infection in a Pregnant Woman and Newborns.

HCMV infection in pregnant women was determined by one or more of the following parameters: virus isolation from urine, saliva, blood, seroconversion for anti-HCMV antibodies. A congenital HCMV infection in a newborn was determined by HCMV isolation from urine during the first week of life. A HCMV infection in newborns was determined by virus isolation from urine.

4. Determination of a HCMV Infection in Transplanted Patients.

HCMV infection in transplanted patients was determined by the presence of pp65-positive PMNL (antigenemia) in peripheral blood as determined by indirect immunofluorescence and the presence of the HCMV genome in the same cells as determined by PCR.

5. Virological Detection of HCMV.

HCMV isolation. The "shell vial" procedure [23] was used for HCMV isolation from urine and saliva. The inoculated cells were fixed 24–48 hours after inoculation and stained in an indirect immunofluorescence (IIF) assay using a monoclonal antibody reacting with HCMV-IE1/IE2 gene product (EI3 from Bioline, Paris, France).

Antigenemia. The presence of HCMV-pp65 (ppUL83) in PMNL was determined as originally described by Schirm et al. [24] and modified by Revello et al [25] using a HCMV-pp65 specific pool of two monoclonal antibodies (Biotest, Frankfurt, Germany) in IIF tests.

Determination of the presence of HCMV genome by PCR. Aliquots of $5 \times 10^5$ PMNL were resuspended in 100 µl of PCR buffer (KCl 50 mM, Tris-HCl 10 mM, pH 8.3, $MgCl_2$ 2 mM, gelatin 0.01%), with non-ionic detergents and Proteinase K. Samples were incubated at 60° C. for one hour and then at 95° C. for 20 minutes to inactivate the proteinase. Thirty microliters of each sample were added to 20 µl of reaction buffer containing 50 mM KCl, 10 mM Tris-HCl pH 8.3, 2 mM $MgCl_2$, 0.2 mM each of the four deoxynucleotide triphosphates, 50 picomoles of each primer and 1.25 units of native Taq DNA-polymerase (Perkin Elmer Cetus, Norwalk, Conn., USA). HCMV specific primers were synthesized by Genset (Paris, France). Sequences are from the 4th exon of HCMV immediate early gene (EcoRI J fragment of the AD169 strain) and correspond to nucleotides 1767 to 1786 and from nucleotide 1894 to 1913. Using these primers, a fragment of 147 base pairs was amplified. A third oligonucleotide consisting of nucleotides 1807–1847 was complementary to the antisense DNA strand in the region between the binding sites of the other oligonucleotides and was used for hybridization [26]. The amplification reaction was carried out in a DNA thermal cycler (Perkin-Elmer/Cetus, Norwalk, Conn., USA) for 35 cycles. Each sample was initially subjected to analysis with oligonucleotide primers GH26 and GH27 (Perkin Elmer Cetus) (20 pmol each), with flank a conserved region of the HLA-DQa locus, to determine the capacity of DNA to be amplified. Fifteen microliters of the reaction mixture were subjected to electrophoresis on 1.2% "NUSIEVE" GTG-agarose and 0.4% Seakem LE-agarose (FMC Bioproducts, Rockland, Me., USA) gel. The DNA was visualized by UV fluorescence after ethidium bromide staining. Nucleic acids were denatured and neutralized using standard procedures and then transferred to nylon membranes (Mybond N, Amersham, UK) using a trans-blott apparatus (Hoefer Scientific Instruments, San Francisco, Calif.). Hybridization with a terminally labeled oligonucleotide was carried out by a commercial kit (3'-oligolabelling and detection system, ECL, Amersham, UK) as suggested by the manufacturers. The sensitivity and specificity of the PCR reaction were determined as described in a previous work [27].

6. Results.

As summarized in Table 3, five different fusion proteins have been comparatively tested.

The first fusion protein (rpCMV-1A) carries the two ppUL32 major antigenic regions fused together. The second fusion protein (rpCMV-3B) carries the COOH half of ppUL44. The third fusion protein (rpCMV-4) carries three regions (two regions of ppUL32 and one of ppUL44) fused together. Fusion proteins rpCMV-9 and rpCMV-26 carry large fragments of ppUL83 and ppUL80a respectively. The cut-off values for the manual assay, for each recombinant protein, are reported in Table 3 and correspond to Optical Density values higher than the maximum value obtained from the 210 serum samples (they approximately correspond to the mean values plus 4–5 standard deviations). In order to evaluate the sensitivity of the rec-EIA, 150 serum samples were selected from several hundred sera because they definitely contained IgM-to HCMV as they gave an IgM-positive result with both conv-EIA and WB. Sera were divided into three groups on the basis of the conv-EIA titre for HCMV-specific IgM. In particular, sera with OD values between 210 and 400 were considered to have a low IgM titre, those with OD ($\times 10^3$) from 401 to 800 were considered to have a medium titre, and those with OD ($\times 10^3$) higher than 800 were considered to have a high IgM titre. As summarized in Table 6, all the sera with medium and high IgM titres to HCMV reacted with one or more fusion proteins. Among the sera with a low IgM titre only two were not detected by any fusion protein. The % of reactivity is therefore higher than 98%. The highest reactivity obtained was against fusion proteins rpCMV-3B and rpCMV-4 and the combination of proteins rpCMV-4, rpCMV-9 and rpCMV-26 gave a reactivity of 98%. Only one serum did not react with this combination and was found to be reactive with fusion protein rpCMV-3B alone.

Having determined the high sensitivity of the recombinant EIA, several sera obtained from different groups of subjects were tested. Table 7 compares the results obtained by recombinant EIA with fifty-one sera obtained from pregnant women with the results obtained by a conv-EIA with the same sera. Among eighteen HCMV uninfected pregnant women, none was found IgM-positive by either conventional or recombinant EIA. On the contrary, among twenty-six HCMV-infected pregnant women who did not transmit the infection to their offspring, recombinant EIA detected IgM in twenty cases, while conv-EIA detected IgM in only twelve cases. Among a group of eight HCMV-infected pregnant women who transmitted the infection, all eight were found IgM-positive by recombinant and six by conv-EIA. The highest reactivity was always observed against the triple antigen fusion protein (fusion protein rpCMV-4). The combination of proteins rpCMV-4, rpCMV-9 and rpCMV-26 gave the maximum reactivity. As shown in Table 7, a significant difference in IgM titre to fusion protein rpCMV-4 was observed between HCMV-infected pregnant women who did not transmit the infection (lower titres) and those who transmitted the infection (higher titres). Although less significant, also the titre against rpCMV-26 was different in the two groups (table 7). The differences in titres to fusion proteins rpCMV-3B and rpCMV-9 were not significant.

A group of thirty-five sera from newborns was also tested (Table 8). Among ten HCMV-uninfected newborns, none was found IgM-positive by either conventional or recombinant EIA. On the contrary, among six sera obtained from six congenitally infected newborns during the first week of life, two gave a positive reaction by rec-EIA and none with the conventional test. The maximum IgM reactivity observed was specific for fusion proteins rpCMV-9 and rpCMV-26. In another group of nineteen sera from newborns persistently excreting HCMV in urine during the first year of life (these newborns were not checked for HCMV at birth) rec-EIA detected IgM in ten cases while conv-EIA detected IgM in only two cases. The maximum IgM reactivity obtained was against fusion proteins rpCMV-4 and rpCMV-26 and the combination of rpCMV-4, rpCMV-9 and rpCMV-26 gave the maximum reactivity.

Figure 17A:
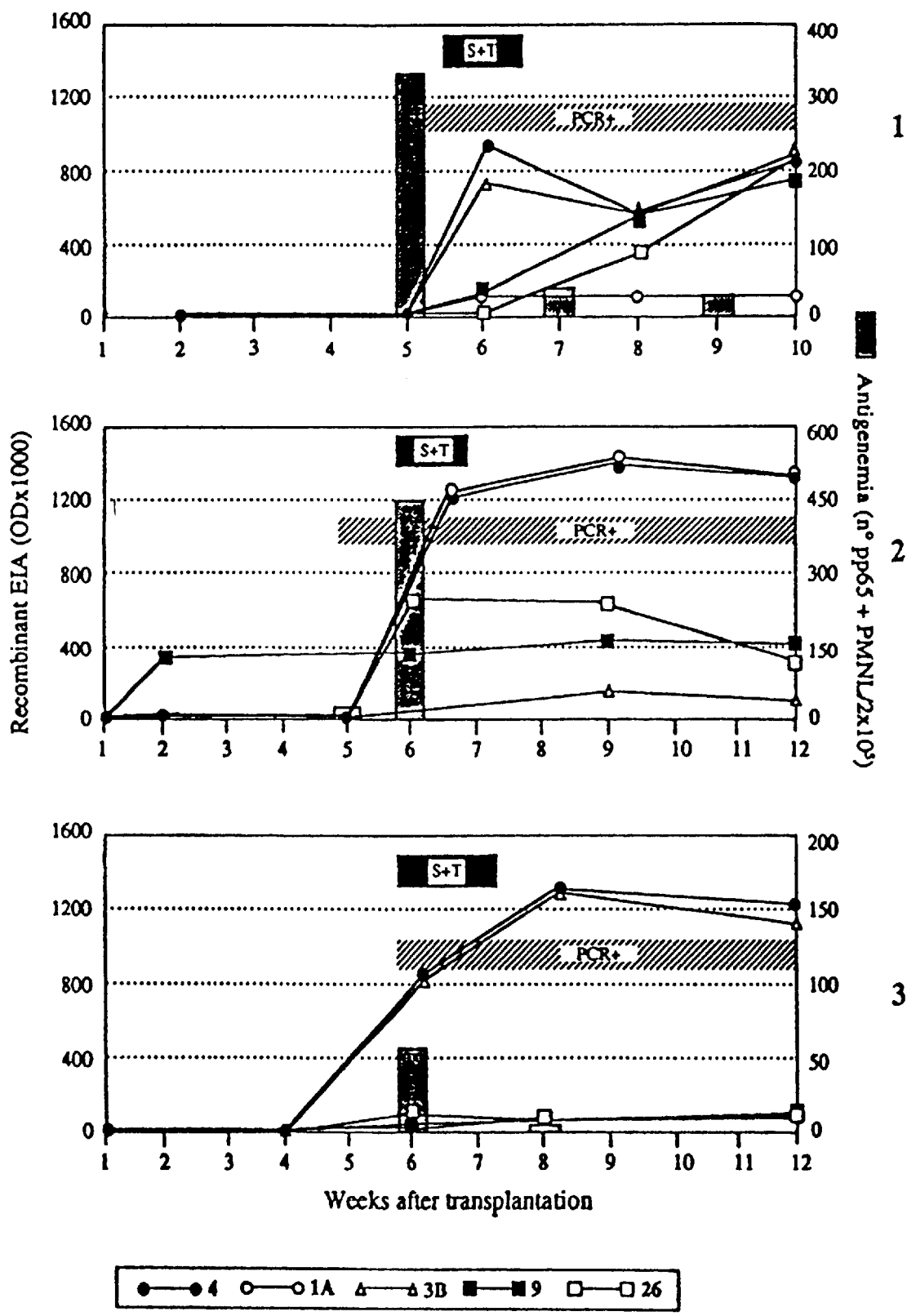
FIGS. 17A and 17B shows the follow up in six transplanted patients undergoing primary and, respectively, secondary, HCMV infection, wherein graphs A1 and A2 relate to kidney transplant recipients and graphs A3, B1, B2 and B3 relate to heart transplant recipients.
Figure 17B:
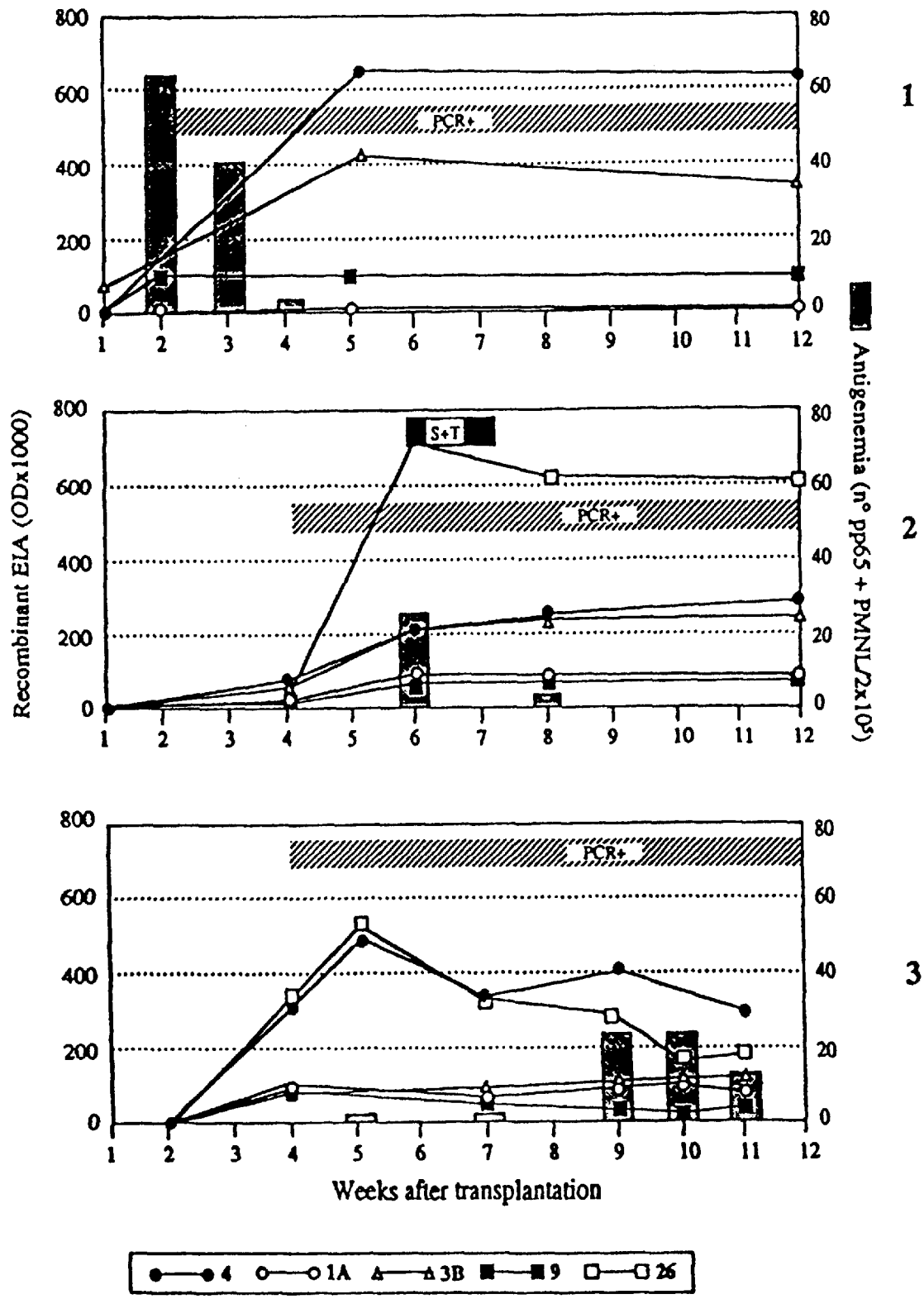

Representative examples of the virological and serological monitoring of HCMV infection in transplant recipients are shown in FIGS. 17A and 17B. In FIG. 17A three primary and in FIG. 17B three cases of secondary HCMV infections are shown. A1 and A2 are follow up of kidney, A3, B1,2 and B3 of heart transplant recipients. S+T means Symptoms and gancyclovir treatment; PCR+ means positive detection of HCMV genome in polymorphonuclear cells.

From the data presented, fusion protein rpCMV-4 was the one giving the highest reactivity with IgM antibodies presented in sera from healthy adults, pregnant women, infected newborns, and transplant recipients. However, fusion protein rpCMV-4 alone could not represent the entire complex of viral antigen reacting with anti-HCMV IgM. On the contrary, the combination of fusion proteins rpCMV-4, rpCMV-9, rpCMV-26 can efficiently replace the virus in IgM detection. In fact, as shown in Tables 9 and 10, 99.6% of IgM-positive sera gave a positive IgM reaction with one or more of these fusion proteins. When the rec-EIA with the three clones was compared with conv-EIA and WB, recEIA and WB gave the same results, and both procedures were more sensitive than conv-EIA. This means that the sensitivity and specificity of the rec-EIA according to the present invention is very similar to that of WB, which is a very sensitive and specific procedure for HCMV-IgM detection [30,31].

LIST OF THE REFERENCES

1. Landini M. P. New approaches and perspectives in cytomegalovinus diagnosis. Prog. Med Mirol 1993; 4, 157–177.
2. Nielsen St, Sorensen I, Andersen E L K. Kinetics of specific immunoglobulins M,E,A and G in congenital, primary, and secondary cytomegalovirus infection studied by antibody-capture enzyme-linked immunosorbent assay. J din Microbiol 1988; 26: 654–661.
3. Basson J, Tardy J C, Aymard M. Pattern of anti-cytomegalovirus IgM antibodies determined by immuno-blotting. A study of kidney graft recipients developing a primary or recurrent CMV infection. Arch Virol 1989; 108: 259–270.
4. Drew W L. Nonpulmonary manifestations of cytomegalovirus infection in immuno-compromized patients. Clin Microphiol Rev 1992; 5: 204–210.
5. Lazzarotto T, Dalla Casa B, Campisi B, Landini N I P. Enzyme-linked immunoadsorbent assay for the detection of cytomegalovirus-IgM: Comparison between eight commercial kits, immunofluorescence and immunoblotting. J Clin Lab Anal 1992; 6: 216–218.
6. Jahn O, Scholl B C, Traupe B, Fleckenstein B. The two major phosphoproteins (pp65 and pp150) of human cytomegalovirus and their antigenic properties. J Gen Virol 1987; 68, 1327–1337.
7. Landini M P., Lazzarotto T, Ripalti A, Guan M X, La Placa M. Antibody response to recombinant Lambda gt11 fusion proteins in Cytomegalovirus infection. J Clin Microbiol 1989; 27: 2324–2327.
8. Landini M P, Guan M X, Jahn G, Lindenmeier W, Mach M, Ripalti A, Necker A, Lazzarotto T, Plachter B. Large scale screening of human sera with Cytomegalovirus recombinant antigens. J Clin Microbiology 1990; 28:1375–1379.
9. Landini M P, Ripalti A, Sra K , Pouletty P. Human cytomegalovirus structural proteins: immune reaction against pp150 synthetic peptides. J Clin Microbiol 1991; 29: 1868–1872.
10. Plachter B, Wieczorek L, Scholl B -C, Ziegelmaler R and Jahn G. Detection of Cytomegalovirus antibodies by an enzyme linked immunosorbent assay using recombinant polypeptides of the large phosphorylated tegument protein pp150. J Clin Microbiol 1992; 30:201–206.
11. Ripalti A, Landini M P, Mocarski E S and La Placa M. identification and preliminary use of recombinant lambda gt11 fusion proteins in Cytomegalovirus diagnosis. J Gen Virol 1989; 70:1247–1251.
12. Ripalti A, Ruan Q, Boccuni M C, Campanini F, Bergamini G and Landini M P. Construction of a polyepitope fusion antigens of human cytomegalovirus ppUL32: reactivity with human antibodies J Clin Microbiol 1994 ; 32: 358–363.
13. Scholl B C, Von Hintzestein B, Borisch B, Traupe B, Broker M, Jahn G. Procaryotic expression of immunogenic polypeptides of the large phosphoprotein (pp150) of human cytomegalovirus J Gen Virol 1988; 69:1195–1204.
14. Vornhagen R, Plachter B, Hinderer W, The T H, Van Zanten J, Matter L, Schmidt C A, Sonneborn H H, Jahn G. Early serodiagnosis of acute cytomegalovirus infection by Enzyme-linked immunosorbent assay using recombinant antigens. J Clin Microbiol 1994; 32: 981–986.
15. Jahn G, Kouzarides T, Mach M, Scholl B C, Plachter B, Traupe B, Preddie E, SatchweilSC, Fleckenstein B, Barrell B O. Map position and nucleotide sequence of the gene for the large structural phosphoprotein of human cytomegalovirus . J Virol 1987; 61:1358–1367.
16. Landini M P, Mirolo G, Baldassarri B, La Placa M. Human immune response to Cytomegalovirus structural polypeptides studied by immunoblotting. J Med Virol 1985; 17:303–311.
17. Novak I, Sova P, Krchnak V, Hamsikova E, Zavadova H E Mapping of serologicallyrelevant regions of human cytomegalovirus phosphoprotein pp150 using synthetic peptides. J Gen Virol 1991; 72:1409–1413.
18. Mocarski E S, Pereira L, Michael N. Precise localisation of genes on large animal genomes: use of lamba gt11 and monoclonal antibodies to map the gene for a Cytomegalovirus protein family. Proceedings of the National Academy of Science (USA) 1985; 82:1266–1270
19. Karlin 5, Mocarski E S, Schachtel G A. Molecular evolution of herpes viruses: genomic and protein sequence comparisons. Journal of Virology 1994; 68: 1886–1902.
20. Bolling T Y, Mandecki M. An *Escherichia coli* expression vector for high-level production of heterologous proteins in fusion with CVP-KDO synthetase. Bio/Techniques 1990; 8: 488–490.
21. Ripalti A, Dal Monte P, Boccuni, M C, Campanini, F, Lazzarotto T, Campisi B, Ruan Q, Landini M P. Prokaryotic expression of a large fragment of the most antigenic cytomegalovirusDNA-binding protein (ppUL44) and its reactivity with human antibodies. J Virol Methods 1994;46: 39–50.
22. Robinson I M, Pilot-Matias T I, Pratt S D, Patel C B, Bevirt T S, Hunt I C. Analysis of the humoral response to the flagellin protein of *Borrelia burgdorferi*: cloning of regions capable of differentiating lyme disease from syphilis. J Clin Microbiol 1993; 3 1: 629–635.
23. Gleaves C A, Smith T F, Shuster E A, Pearson &R. Rapid detection of cytomegalovirus in MRC5 cells inoculated with urine specimens by use of low speed centrifugation and monoclonal antibody to an early antigen. J Clin Microbiol 1984; 19: 917–919.
24. Van der Biji, Torensma R, Son W J, Schirm J, Tegzess A M, The T H. Rapid immunodiagnosis of active cytomegalovirus infection by monoclonal antibody staining of blood leukocytes. J Med Virol 1988; 25:179–188.
25. Revello M G, Zavattoni M, Percivalle E, Grossi P, Gerna G. Correlation between immunofluorescent detection of human cytomegalovirus immediate early antigens in polymorphonuclear leukocytes and viremia. J inf Dis 1989; 160:159–160.
27. Lazzarotto T, Furlini 6, Re M C, Ramazzotti E, Campisi B, Landini M P. Human cytomegalovirus replication correlates with differentiation in a hematopoletic progenitor cell line and can be modulated by HtV. Arch Virol 1994135:13–28.
30. Gold D, Ashley R, Handsfield H H, Verdon M, Leach L, Mills I, Drew L, Corey L. Immunoblot analysis of the humoral immune response in primary cytomegalovirus infection. J Inf Dis 1988157: 3t9–325.
31. Re M C, Landini M P. IgM to human cytomegalovirus: Comparison of two enzyme immunoassays and IgM reactivity to viral polypeptides detected byimmunoblotting. J Clin LabAnal 1989; 3:169–173.

---

We claim:

1. A recombinant proteic material, capable of binding with antibodies against human Cytomegalovirus (HCMV), comprising a fusion protein, at least part of the amino acids thereof being encoded either by the nucleotide sequence SEQ ID NO: 1, read from nucleotides 001 to 900, or by the nucleotide sequence SEQ ID NO: 3, read from nucleotides 001 to 906.

2. A recombinant proteic material as claimed in claim 1, wherein said fusion protein comprises at least a portion of β-Galactosidase.

3. A diagnostic reagent for detecting HCMV infection by serological methods comprising a fusion protein as claimed in claim 1.

4. A diagnostic kit for detecting, by serological methods, the presence of antibodies to human Cytomegalovirus (HCMV), comprising a diagnostic reagent as claimed in claim 3, wherein said diagnostic reagent is adsorbed on a solid medium.

5. A mixture of recombinant antigens to detect Cytomegalovirus-specific IgM in human sera by enzyme immunoassay, said mixture comprising, in combination:

(i)—a first fusion protein comprising: a first region, carrying an amino acid sequence (H10) corresponding to at least one epitope that binds HCMV-specific IgM, between aa 202 and aa 434, inclusive, of viral protein pp52; a second region, carrying an amino acid sequence (F3) corresponding to at least one epitope that binds HCMV-specific IgM, between aa 1006 to aa 1048, inclusive, of viral protein pp150; and a third region, carrying an amino acid sequence (A1C2) corresponding to at least one epitope that binds HCMV-specific IgM, between aa 595 and aa 614, inclusive, of the same viral protein pp150; at least part of the amino acids thereof being encoded either by the nucleotide sequence SEQ ID NO: 1, read from nucleotides 001 to 900, or by the nucleotide sequence SEQ ID NO: 3, read from nucleotides 001 to 906;

(ii)—a second fusion protein comprising an immunogen region comprising a sequence of amino acids corresponding to at least one epitope that binds HCMV-specific IgM, between aa 297 to aa 510, inclusive, of the viral major matrix protein pp65 encoded by the viral gene UL83; and (iii)—a third fusion protein comprising an immunogen region comprising a sequence of amino acids corresponding to at least one epitope that binds HCMV-specific IgM, between aa 117 to aa 373, of the viral assembly protein pp38 encoded by the viral gene UL80a.

6. A mixture of recombinant antigens as claimed in claim 5, wherein said regions include the entire amino acid sequence for each of said first region H10, said second region F3, said third region A1C2, protein pp65, and protein pp38.

7. A mixture of recombinant antigens as claimed in claim 5, wherein said fusion protein comprises at least a portion of protein CKS.

8. A diagnostic reagent for detecting Cytomegalovirus-specific IgM in human sera by enzyme immunoassay comprising the mixture of fusion proteins as claimed in claim 5.

9. A diagnostic reagent suitable for detecting Cytomegalovirus-specific IgM in human sera by enzyme immunoassay comprising a first fusion protein as claimed in claim 5.

10. A diagnostic kit for detecting Cytomegalovirus-specific IgM in human sera by enzyme immunoassay comprising a plurality of microparticles, each of said microparticles being coated with at least one of the fusion proteins of the mixture as claimed in claim 5.

11. A diagnostic kit for detecting Cytomegalovirus-specific IgM in human sera by enzyme immunoassay comprising a plurality of microparticles, each of said microparticles being coated with the mixture comprising the three fusion proteins as claimed in claim 5.

12. A plasmid, capable of being inserted into either prokaryote or eukaryote host organism, comprising an expression vector pROS, wherein DNA sequence SEQ ID NO: 1 has been inserted at site SmaI, from nucleotide 002 to 907.

13. A recombinant host organism comprising a plasmid as claimed in claim 12, capable of producing a fusion protein comprising a first region, carrying an amino acid sequence (H10) corresponding to at least one epitope that binds HCMV-specific IgM, between aa 202 and aa 434, inclusive, of viral protein pp52; a second region, carrying an amino acid sequence (F3) corresponding to at least one epitope that binds HCMV-specific IgM, between aa 1006 to aa 1048, inclusive, of viral protein pp150; and a third region, carrying an amino acid sequence (A1C2) corresponding to at least one epitope that binds HCMV-specific IgM, between aa 595 and aa 614, inclusive, of the same viral protein pp150.

14. A recombinant proteic material, capable of binding with human Cytomegalovirus (HCMV)-specific antibodies, comprising a mixture of fusion proteins expressed in host organism wherein there has been inserted at least one of the following plasmids: a plasmid as claimed in claim 12; a plasmid capable of being inserted into a prokaryote or eukaryote host organism, comprising a DNA sequence encoding at least one epitope that binds HCMV-specific IgM, between aa 297 to aa 510, inclusive, of the HCMV major matrix protein pp65 encoded by the viral gene UL83, said sequence being linked at the 3' end of a second sequence corresponding to the sequence from amino acid 1 to amino acid 240, inclusive, encoding for protein CKS; a plasmid capable of being inserted into a prokaryotes or eukaryotes host organism, comprising a DNA sequence encoding at least one epitope that binds HCMV-specific IgM, between aa 117 to aa 373, inclusive, of the HCMV assembly protein pp38 encoded by the viral gene UL80a, said sequence being linked at the 3' end of a second sequence corresponding to the sequence from amino acid 1 to amino acid 240, inclusive, encoding for protein CKS.

15. A plasmid according to claim 12, wherein said host organism is *E. coli*.

16. A plasmid capable of being inserted into a prokaryote or eukaryote host organism comprising, combined together, a first DNA sequence encoding at least one epitope that binds HCMV-specific IgM, between aa 202 to aa 434, inclusive, of protein pp52 of HCMV, a second DNA sequence encoding at least one epitope that binds HCMV-specific IgM, between aa 1006 and aa 1048, inclusive, of protein pp150, and a third DNA sequence encoding the amino acid sequence between aa 595 and 614, inclusive, of protein pp 150, wherein DNA sequence SEQ ID NO: 3 or SEQ ID NO: 1 is included in full.

17. A plasmid, capable of being inserted into either prokaryote or eukaryote host organism, comprising an expression vector pJ0200, wherein DNA sequence SEQ ID NO:3 has been inserted between the corresponding sites SacI and BamH-I, from nucleotide 001 to 906.

18. A diagnostic reagent for detecting HCMV infection by serological methods comprising a fusion protein comprising sequence SEQ ID NO: 2.

19. A diagnostic reagent for detecting HCMV infection by serological methods, comprising a fusion protein comprising sequence SEQ ID NO: 4.

20. A method for detecting Cytomegalovirus-specific IgM in human sera by enzyme immunoassay, said method comprising the steps of:

providing a mixture of fusion proteins, the mixture comprising, in combination:
(i)—a first fusion protein comprising: a first region, carrying an amino acid sequence (H10) corresponding to at least one epitope that binds HCMV-specific IgM, between aa 202 and aa 434, inclusive, of viral protein pp52; a second region, carrying an amino acid sequence (F3) corresponding to at one epitope that binds HCMV-specific IgM, between aa 1006 to aa 1048, inclusive, of viral protein pp150; and a third region, carrying an amino acid sequence (A1C2) corresponding to at least one epitope that binds HCMV-specific IgM, between aa 595 and 614, inclusive, of the same viral protein pp150; at least part of the amino acids thereof being encoded either by the nucleotide sequence SEQ ID NO: 1, read from nucleotides 001 to 900, or by the nucleotide sequence SEQ ID NO: 3, read from nucleotides 001 to 906;
(ii)—a second fusion protein comprising an immunogen region consisting in a sequence of amino acids corresponding to at least one epitope that binds HCMV-specific IgM, between aa 297 to aa 510, inclusive, of the viral major matrix protein pp65 encoded by the viral gene UL83; and
(iii)—a third fusion protein comprising an immunogen region consisting in a sequence of amino acids corresponding to at least one epitope that binds HCMV-specific IgM, between aa 117 to aa 373, of the viral assembly protein pp38 encoded by the viral gene UL80a, contacting a sample of human serum with said mixture to form a reaction mixture, contacting said reaction mixture with a conjugate, said conjugate comprising an antibody and an enzyme, adding a substrate for the enzyme, and monitoring the reaction between the conjugate and the substrate to determine the concentration of Cytomegalovirus-specific IgM in the serum.

21. A method for preparing a solid medium comprising a mixture of fusion proteins to prepare a diagnostic kit to detect Cytomegalovirus-specific IgM in human sera by enzyme immunoassay, said method comprising:

providing a mixture comprising in combination: (i)—a first fusion protein comprising: a first region, carrying an amino acid sequence (H10) corresponding to at least one epitope that binds HCMV-specific IgM, between aa 202 and aa 434, inclusive, of viral protein pp52; a second region, carrying an amino acid sequence (F3) corresponding to at least one epitope that binds HCMV-specific IgM, between aa 1006 to aa 1048, inclusive, of viral protein pp150; and a third region, carrying an amino acid sequence (A1C2) corresponding to at least one epitope that binds HCMV-specific IgM, between aa 595 and 614, inclusive, of the same viral protein pp150; at least part of the amino acids thereof being encoded either by the nucleotide sequence SEQ ID NO: 1, read from nucleotides 001 to 900, or by the nucleotide sequence SEQ ID NO: 3, read from nucleotides 001 to 906; (ii)—a second fusion protein comprising an immunogen region consisting in a sequence of amino acids corresponding to at least one epitope that binds HCMV-specific IgM, between aa 297 to aa 510, inclusive, of the viral major matrix protein pp65 encoded by the viral gene UL83; and (iii)—a third fusion protein comprising an immunogen region consisting in a sequence of amino acids corresponding to at least one epitope that binds HCMV-specific IgM, between aa 117 to aa 373, of the viral assembly protein pp38 encoded by the viral gene UL80a; and allowing said mixture to be adsorbed onto at least one solid medium.

22. A method according to claim 21, wherein each of said fusion proteins of said mixture is separately adsorbed onto different solid media, one protein per medium.

* * * * *